(12) United States Patent
Parnes et al.

(10) Patent No.: US 10,828,365 B2
(45) Date of Patent: Nov. 10, 2020

(54) TREATMENT OF ASTHMA WITH ANTI-TSLP ANTIBODY

(71) Applicants: Amgen Inc., Thousand Oaks, CA (US); MedImmune, LLC, Gaithersburg, MD (US)

(72) Inventors: Jane R. Parnes, Agoura Hills, CA (US); Janet Griffiths, Gaithersburg, MD (US)

(73) Assignee: AMGEN INC., Thousand Oaks, CA (US)

(*) Notice: Subject to any disclaimer, the term of this patent is extended or adjusted under 35 U.S.C. 154(b) by 133 days.

(21) Appl. No.: 15/951,602

(22) Filed: Apr. 12, 2018

(65) Prior Publication Data

US 2018/0296669 A1  Oct. 18, 2018

Related U.S. Application Data

(60) Provisional application No. 62/553,477, filed on Sep. 1, 2017, provisional application No. 62/553,575, filed on Sep. 1, 2017, provisional application No. 62/484,864, filed on Apr. 12, 2017.

(51) Int. Cl.
*A61K 39/395* (2006.01)
*A61P 11/06* (2006.01)
*C07K 16/24* (2006.01)
*A61K 39/00* (2006.01)

(52) U.S. Cl.
CPC ............ *A61K 39/395* (2013.01); *A61P 11/06* (2018.01); *C07K 16/24* (2013.01); *C07K 16/244* (2013.01); *A61K 2039/505* (2013.01); *A61K 2039/545* (2013.01); *A61K 2039/55* (2013.01); *C07K 2317/21* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,585,089 A | 12/1996 | Queen et al. | |
| 5,693,762 A | 12/1997 | Queen et al. | |
| 7,982,016 B2 | 7/2011 | Comeau et al. | |
| 8,163,284 B2* | 4/2012 | Comeau ............. | C07K 16/24 424/133.1 |
| 8,637,019 B2 | 1/2014 | Presta | |
| 2012/0020988 A1 | 1/2012 | Auer et al. | |
| 2016/0264658 A1* | 9/2016 | Ahmed ............. | C07K 16/244 |
| 2017/0066823 A1 | 3/2017 | Edwards et al. | |

FOREIGN PATENT DOCUMENTS

| | | | |
|---|---|---|---|
| EP | 0546073 B1 | 9/1997 | |
| WO | WO-90/04036 A1 | 4/1990 | |
| WO | WO-91/10741 A1 | 7/1991 | |
| WO | WO-94/02602 A1 | 2/1994 | |
| WO | WO-96/33735 A1 | 10/1996 | |
| WO | WO-2010/017468 A1 | 2/2010 | |
| WO | WO-2016/142426 A1 | 9/2016 | |
| WO | WO-2017/042701 A1 | 3/2017 | |

OTHER PUBLICATIONS

Allakhverdi et al., Thymic stromal lymphopoietin as a mediator of crosstalk between bronchial smooth muscles and mast cells, J. Allergy Clin. Immunol., 123(4):958-60 (2009).
Allakhverdi et al., Thymic stromal lymphopoietin is released by human epithelial cells in response to microbes, trauma, or inflammation and potently activates mast cells, J. Exp. Med., 204(2):253-8 (Feb. 2007).
American Thoracic Society et al., ATS/ERS recommendations for standardized procedures for the online and offline measurement of exhaled lower respiratory nitric oxide and nasal nitric oxide, 2005, Am. J. Respir. Critr. Care Med., 171(8):912-30 (Apr. 2005).
Antonicelli et al., Asthma severity and medical resource utilisation, Eur. Respir. J., 23(5):723-9 (May 2004).
Barnes et al., Risk of severe life threatening asthma, Thorax, 51(11):1073 (Nov. 1996).
Bateman et al., Can guideline-defined asthma control be achieved? The Gaining Optimal Asthma ControL study, Am. J. Respir. Crit. Care Med., 170(8):836-44 (2004).
Bates et al., Animal models of asthma, Am. J. Physiol. Lung Cell Mol. Physiol., 297(3):L401-10 (Sep. 2009).
Bel et al., Moving upstream: Anti-TSLP in persistent uncontrolled asthma, N. Engl. J. Med., 377(10):989-91 (Sep. 2017).
Bel et al., Oral glucocorticoid-sparing effect of mepolizumab in eosinophilic asthma, N. Engl. J. Med., 371(13):1189-97 (Sep. 2014).
Bleck et al., Diesel exhaust particle-exposed human bronchial epithelial cells induce dendritic cell maturation and polarization via thymic stromal lymphopoietin, J. Clin. Immunol., 28(2):147-56 (Mar. 2008).
Bleecker et al., Efficacy and safety of benralizumab for patients with severe asthma uncontrolled with high-dosage inhaled corticosteroids and long-acting β2-agonists (SIROCCO): a randomised, multicentre, placebo-controlled phase 3 trial, The Lancet, 388(10056):2115-27 (2016).
Brightling et al., Efficacy and safety of tralokinumab in patients with severe uncontrolled asthma: a randomised, double-blind, placebo-controlled, phase 2b trial, Lancet Repsir. Med., 3(9):692-701 (Sep. 2015).

(Continued)

*Primary Examiner* — Daniel C Gamett
(74) *Attorney, Agent, or Firm* — Marshall, Gerstein & Borun LLP

(57) ABSTRACT

The present disclosure, relates, in general, to methods of treating asthma, including severe asthma and eosinophilic asthma, using an antibody specific for thymic stromal lymphopoietin (TSLP).

48 Claims, 53 Drawing Sheets

Specification includes a Sequence Listing.

(56) References Cited

OTHER PUBLICATIONS

Brightling et al., Targeting TNF-alpha: a novel therapeutic approach for asthma, J. Allergy Clin. Immunol., 121(1):5-10, quiz 11-2 (Jan. 2008).

Bruggermann et al., Designer mice: the production of human antibody repertoires in transgenic animals, Year in Immunol., 7:33 (1993).

Calvén et al., Viral stimuli trigger exaggerated thymic stromal lymphopoietin expression by chronic obstructive pulmonary disease epithelium: role of endosomal TLR3 and cytosolic RIG-I-like helicases, J. Innate Immun., 4(1):86-99 (2012).

Castro et al., Reslizumab for inadequately controlled asthma with elevated blood eosinophil counts: results from two multicentre, parallel, double-blind, randomised, placebo-controlled, phase 3 trials, Lancet Respir. Med., 3(5):355-66 (May 2015).

Chung et al., International ERS/ATS guidelines on definition, evaluation and treatment of severe asthma, Eur. Respir. J., 43(2):343-73 (2014).

Corren et al., Lebrikizumab treatment in adults with asthma, N. Engl. J. Med., 365(12):1088-98 (Sep. 2011).

Corren et al., Tezepelumab demonstrates clinically meaningful improvements in asthma control (ACQ-6) in patients with uncontrolled asthma: results from a phase 2b clinical trial, J. Allergy Clin. Immunol., 141(2):AB80 (Feb. 2018).

Corren et al., Tezepelumab in Adults with Uncontrolled Asthma, N. Engl. J. Med., 377(1):936-46 (Sep. 2017).

Cukic et al., Asthma and Chronic Obstructive Pulmonary Disease (COPD)—Differences and Similarities, Mater Sociomed., 24(2):100-5 (2012).

Diamant et al., Inhaled allergen bronchoprovocation tests, J. Allergy Clin. Immunol., 132(5):1045-1055.e6 (Nov. 2013).

Dweik et al., An official ATS clinical practice guideline: interpretation of exhaled nitric oxide levels (FENO) for clinical applications, Am. J. Respir. Crit. Care Med., 184(5):602-15 (Sep. 2011).

FitzGerald et al., Benralizumab, an anti-interleukin-5 receptor a monoclonal antibody, as add-on treatment for patients with severe, uncontrolled, eosinophilic asthma (CALIMA): a randomised, double-blind, placebo-controlled phase 3 trial, Lancet, 388(10056):2128-41 (Oct. 2016).

Froidure et al., Asthma phenotypes and IgE responses, Eur. Respir. J., 47(1):304-19 (2016).

Gauvreau et al., Effects of an anti-TSLP antibody on allergen-induced asthmatic responses, N. Engl. J. Med., 370(22):2102-10 (May 2014).

Gavala et al., Virus/allergen interactions in asthma, Curr. Allergy Asthma Rep., 13(3):298-307 (Jun. 2013).

Gilliet et al., Human dendritic cells activated by TSLP and CD40L induce proallergic cytotoxic T cells, J. Exp. Med., 197(8):1059-63 (Apr. 2003).

Hanania et al., Exploring the effects of omalizumab in allergic asthma: an analysis of biomarkers in the EXTRA study, Am. J. Respir. Crit Care Med., 187(8):804-11 (Apr. 2013).

International Application No. PCT/US2018/027271, International Search Report and Written Opinion dated Aug. 14, 2018.

International Application No. PCT/US2018/027271, Invitation to Pay Additional Fees, dated Jun. 22, 2018.

Jakobovits et al., Analysis of homozygous mutant chimeric mice: deletion of the immunoglobulin heavy-chain joining region blocks B-cell development and antibody production, Proc. Natl. Acad. Sci. 90:2551-5 (1993).

Jakobovits et al., Germ-line transmission and expression of a human-derived yeast artificial chromosome, Nature, 362:255-8 (1993).

Jia et al., Periostin is a systemic biomarker of eosinophilic airway inflammation in asthmatic patients, J. Allergy Clin. Immunol., 130(3):647-54.e10 (Sep. 2012).

Johansson et al., Revised nomenclature for allergy for global use: Report of the Nomenclature Review Committee of the World Allergy Organization, Oct. 2003, J. Allergy Clin. Immunol., 113(5):832-6 (May 2004).

Jones et al., Replacing the complementarity-determining regions in a human antibody with those from a mouse, Nature, 321(6069):522-5 (1986).

Juniper et al., Determining a minimal important change in a disease-specific Quality of Life Questionnaire, J. Clin. Epidemiol., 47(1):81-7 (Jan. 1994).

Juniper et al., Development and validation of a questionnaire to measure asthma control, Eur. Respir. J., 14(4):902-7 (Oct. 1999).

Juniper et al., Identifying 'well-controlled' and 'not well-controlled' asthma using the Asthma Control Questionnaire, Respir. Med., 100(4):616-21 (Apr. 2006).

Juniper et al., Measurement properties and interpretation of three shortened versions of the asthma control questionnaire, Respir. Med., 99(5):553-8 (May 2005).

Juniper et al., Validation of a standardized version of the Asthma Quality of Life Questionnaire, Chest, 115(5):1265-70 (May 1999).

Keene et al., Analysis of exacerbation rates in asthma and chronic obstructive pulmonary disease: example from the TRISTAN study, Pharm. Stat., 6(2):89-97 (Apr. 2007).

Kemp et al., Epinephrine: the drug of choice for anaphylaxis. A statement of the World Allergy Organization, Allergy, 63(8):1061-70 (Aug. 2008).

Kim et al., TSLP elicits IL-33-independent innate lymphoid cell responses to promote skin inflammation, Sci. Transl. Med., 5(170):170ra16 (2013).

Lane et al., An international observational prospective study to determine the cost of asthma exacerbations (COAX), Respir. Med., 100(3):434-50 (Mar. 2006).

Lee et al., Thymic stromal lymphopoietin is induced by respiratory syncytial virus-infected airway epithelial cells and promotes a type 2 response to infection, J. Allergy Clin. Immunol., 130(5):1187-96. e5 (Nov. 2012).

Li et al., Periostin: its role in asthma and its potential as a diagnostic or therapeutic target, Respir. Res., 16:57 (May 2015).

Miller et al., General considerations for lung function testing, Eur. Respir. J., 26(1):153-61 (2005).

Mishra et al., From bedside to bench to clinic trials: identifying new treatments for severe asthma, Dis. Model Mech., 6(4):877-88 (Jul. 2013).

Moore et al., Identification of asthma phenotypes using cluster analysis in the Severe Asthma Research Program, Am. J. Respir. Crit. Care Med., 181(4):315-23 (2010).

Morrison et al., Chimeric human antibody molecules: mouse antigen-binding domains with human constant region domains, Proc. Natl. Acad. Sci. USA, 81(21):6851-5 (1984).

Nagata et al., Differential role of thymic stromal lymphopoietin in the induction of airway hyperreactivity and Th2 immune response in antigen-induced asthma with respect to natural killer T cell function, Int. Arch. Allergy Immunol., 144(4):305-14 (2007).

Nakamura et al., Cigarette smoke extract induces thymic stromal lymphopoietin expression, leading to T(H)2-type immune responses and airway inflammation, J. Allergy Clin. Immunol., 122(6):1208-14 (Dec. 2008).

Ortega et al., Mepolizumab treatment in patients with severe eosinophilic asthma, N. Engl. J. Med., 371(13):1198-207 (2014).

Pandey et al., Cloning of a receptor subunit required for signaling by thymic stromal lymphopoietin, Nat. Immunol., 1(1):59-64 (2000).

Park et al., Cloning of the murine thymic stromal lymphopoietin (TSLP) receptor: Formation of a functional heteromeric complex requires interleukin 7 receptor, J. Exp. Med., 192(5):659-70 (2000).

Partridge, Examining the unmet need in adults with severe asthma, Eur. Resp. Rev., 16:67-72 (2007).

Paul et al., How are T(H)2-type immune responses initiated and amplified?, Nat. Rev. Immunol., 10(4):225-35 (Apr. 2010).

Pavord et al., Mepolizumab for severe eosinophilic asthma (DREAM): a multicentre, double-blind, placebo-controlled trial, Lancet, 380(9842):651-9 (Aug. 2012).

Pavord et al., The impact of poor asthma control among asthma patients treated with inhaled corticosteroids plus long-acting β2-agonists in the United Kingdom: a cross-sectional analysis, NPJ Prim. Care Respir. Med., 27(1):17 (2017).

(56) References Cited

OTHER PUBLICATIONS

Rabe et al., Worldwide severity and control of asthma in children and adults: the global asthma insights and reality surveys, J. Allergy Clin. Immunol., 114(1):40-7 (2004).

Reche et al., Human thymic stromal lymphopoietin preferentially stimulates myeloid cells, J. Immunol., 167(1):336-43 (Jul. 2001).

Riechmann et al., Reshaping human antibodies for therapy, Nature, 332:323-27 (1988).

Sampson et al., Second symposium on the definition and management of anaphylaxis: summary report—Second National Institute of Allergy and Infectious Disease/Food Allergy and Anaphylaxis Network symposium, J. Allergy Clin. Immunol., 117(2):391-7 (Feb. 2006).

Serra-Bathes et al., Costs of asthma according to the degree of severity, Eur. Respir. J., 12(6):1322-6 (Dec. 1998).

Shikotra et al., Increased expression of immunoreactive thymic stromal lymphopoietin in patients with severe asthma, J. Allergy Clin. Immunol., 129(1):104-11.e1-9 (Jan. 2012).

Sorkness et al., Lung function in adults with stable but severe asthma: air trapping and incomplete reversal of obstruction with bronchodilation, J. Appl. Physiol (1985), 104(2):394-403 (Feb. 2008).

Soumelis et al., Human epithelial cells trigger dendritic cell mediated allergic inflammation by producing TSLP, Nat. Immunol., 3(7):673-80 (Jul. 2002).

Tabrizi et al., Biodistribution mechanisms of therapeutic monoclonal antibodies in health and disease, AAPS J., 12(1):33-43 (Mar. 2010).

Tanaka et al., Human TSLP and TLR3 ligands promote differentiation of Th17 cells with a central memory phenotype under Th2-polarizing conditions, Clin. Exp. Allergy, 39(1):89-100 (Jan. 2009).

To et al., Global asthma prevalence in adults: findings from the cross-sectional world health survey, BMC Public Health, 12:204 (2012).

Tough et al., Features that distinguish those who die from asthma from community controls with asthma, J. Asthma, 35(8):657-65 (1998).

Turner et al., Risk factors for near-fatal asthma. A case-control study in hospitalized patients with asthma, Am. J. Respir. Crit. Care Med., 157(6 Pt. 1):1804-9 (Jun. 1998).

Verhoeyen et al., Reshaping human antibodies: grafting an antilysozyme activity, Science, 239:1534-36 (1988).

Wenzel et al., Dupilumab efficacy and safety in adults with uncontrolled persistent asthma despite use of medium-to-high-dose inhaled corticosteroids plus a long-acting β2 agonist: a randomised double-blind placebo-controlled pivotal phase 2b dose-ranging trial, Lancet, 388(10039):31-44 (Jul. 2016).

Wenzel, Emergence of Biomolecular Pathways to Define Novel Asthma Phenotypes. Type-2 Immunity and Beyond, Am. J. Repir. Cell Mol. Biol., 55(1):1-4 (2016).

Woodruff et al., T-helper type 2-driven inflammation defines major subphenotypes of asthma, Am. J. Respir. Crit. Care Med., 180(5):388-95 (2009).

XOLAIR® (omalizumab): Highlights of Prescribing Information (2016).

Ying et al., Expression and cellular provenance of thymic stromal lymphopoietin and chemokines in patients with severe asthma and chronic obstructive pulmonary disease, J. Immunol., 181(4):2790-8 (Aug. 2008).

Ying et al., Thymic stromal lymphopoietin expression is increased in asthmatic airways and correlates with expression of Th2-attracting chemokines and disease severity, J. Immunol., 174(12):8183-90 (Jun. 2005).

Ziegler et al., The biology of thymic stromal lymphopoietin (TSLP), Adv. Pharmacol., 66:129-55 (2013).

\* cited by examiner

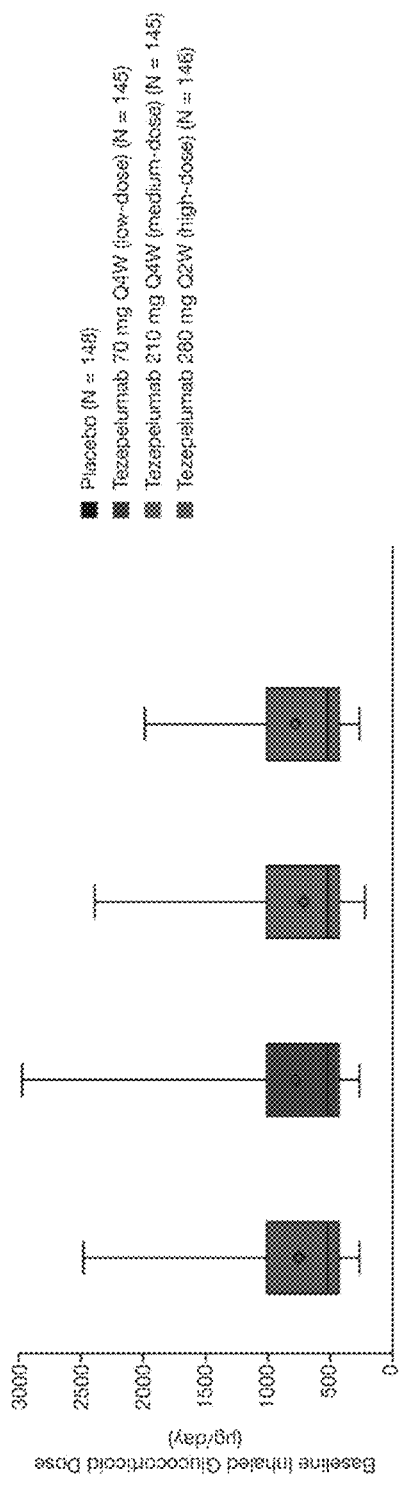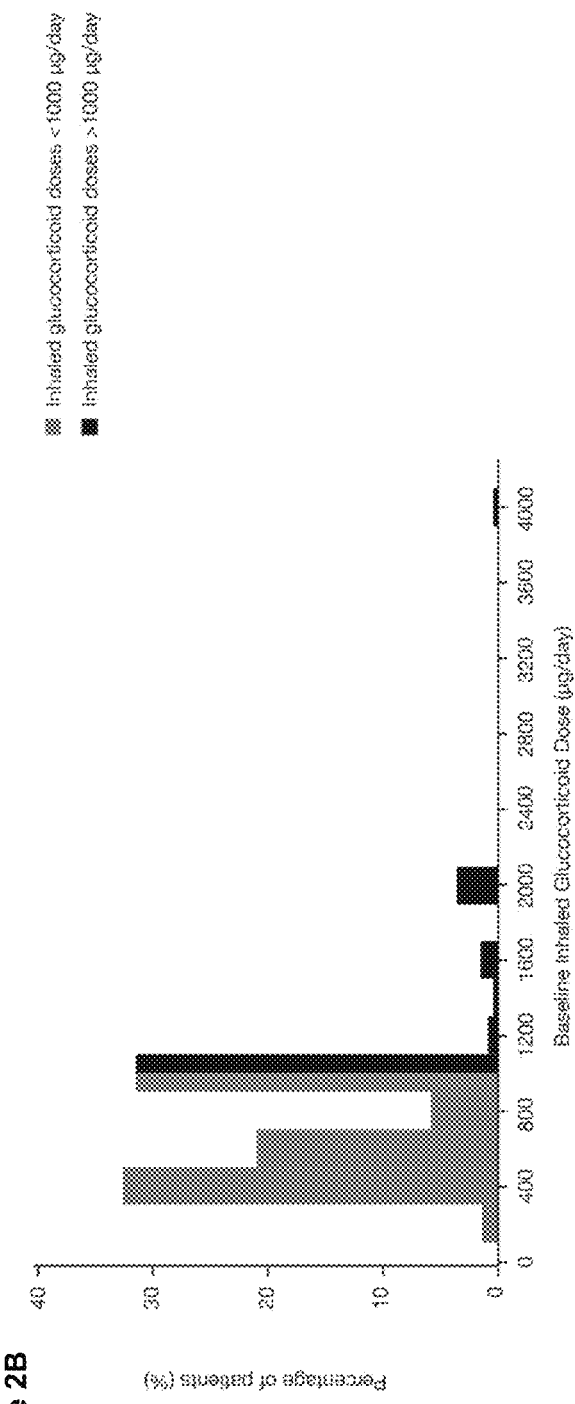
Figure 2A
Figure 2B

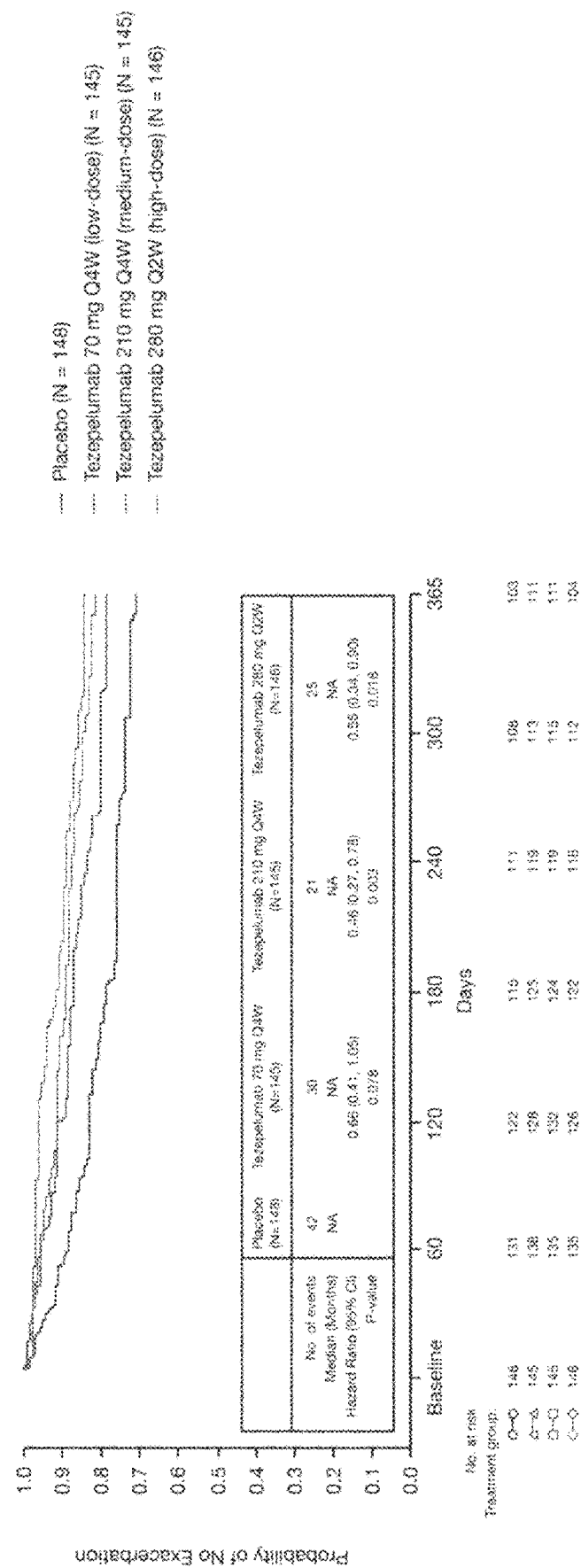
Figure 3  Kaplan-Meier Curve for Time to First Asthma Exacerbation through Week 52 in the Intention-to-Treat Population.
*P-values are nominal and without multiplicity adjustment. CI, confidence intervals; NA, not applicable; Q2W, every 2 weeks; Q4W, every 4 weeks.

Figure 4A Change from Baseline in Peripheral Blood Eosinophils (cell/μl) over Time in the Intention-to-Treat Population
Error bars are representative of standard errors. IgE, immunoglobulin E; Th2, Q2W, every 2 weeks; Q4W, every 4 weeks
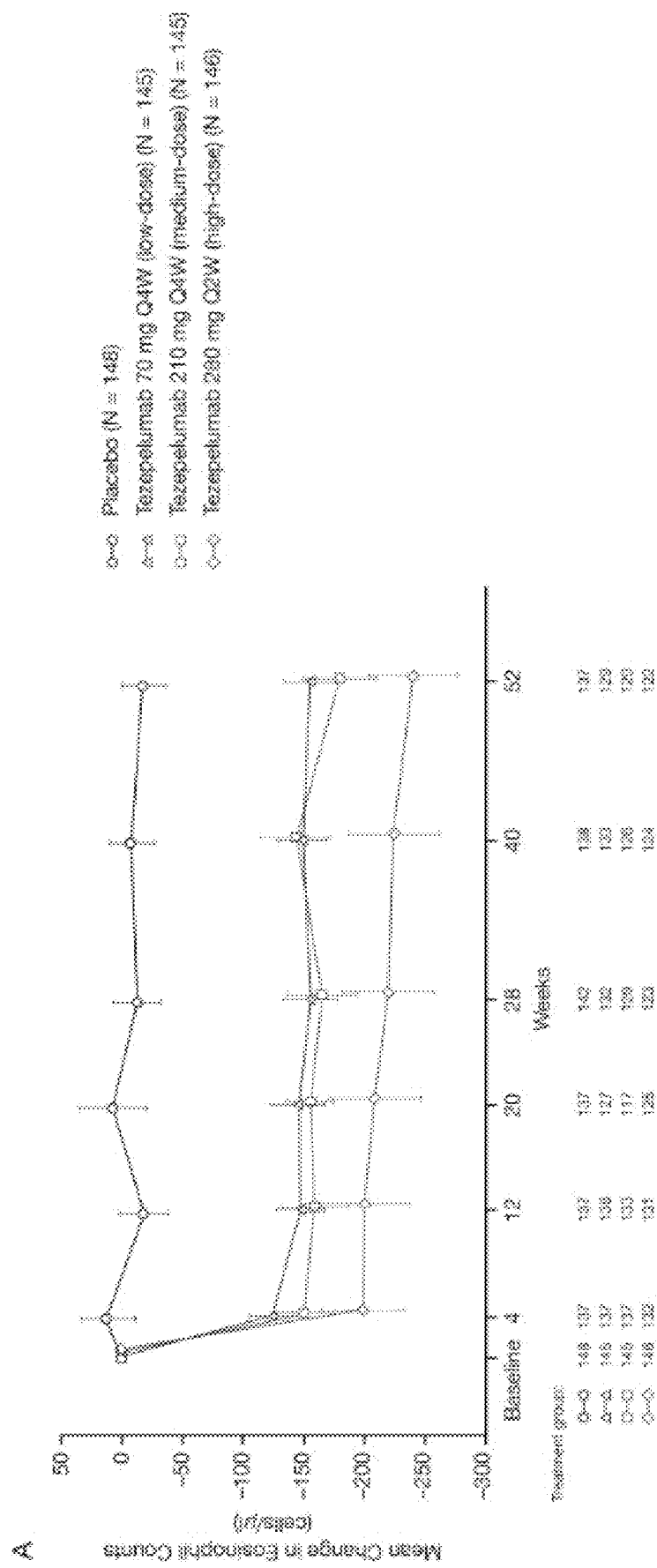

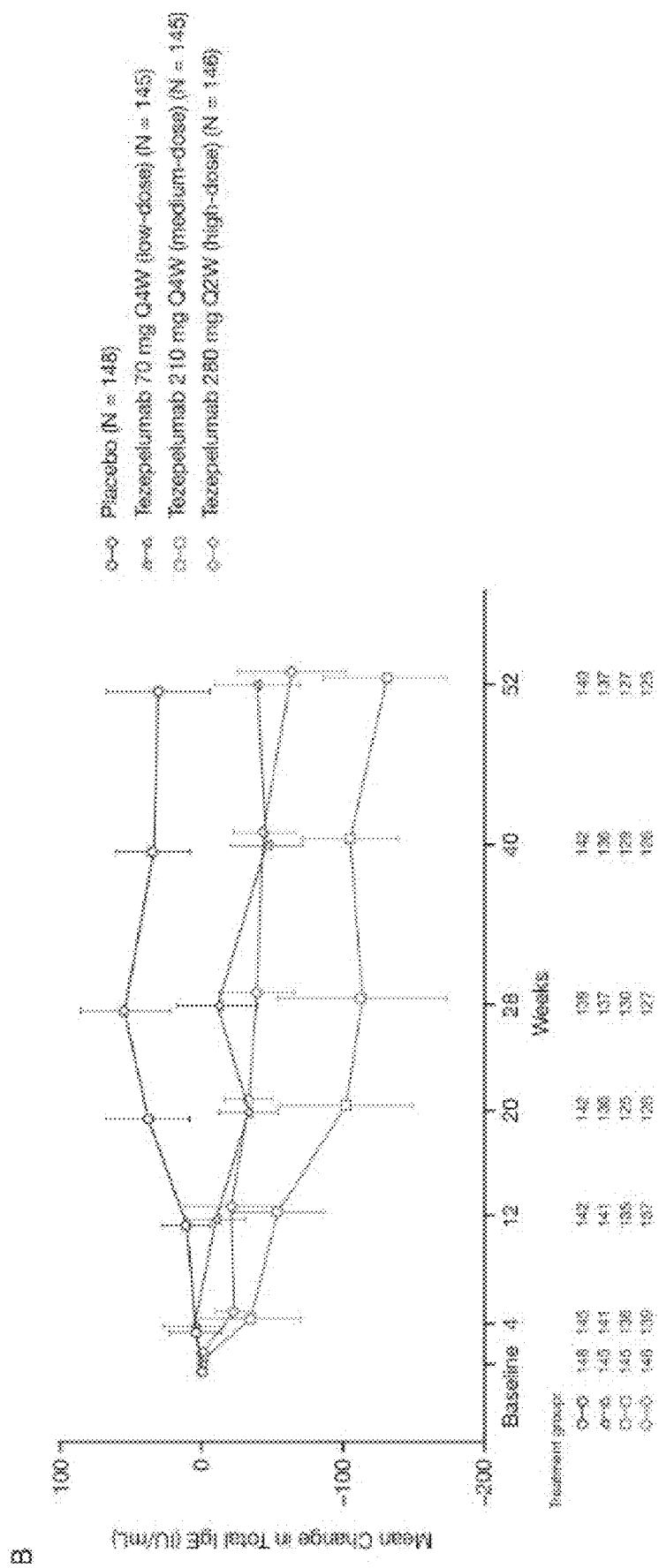

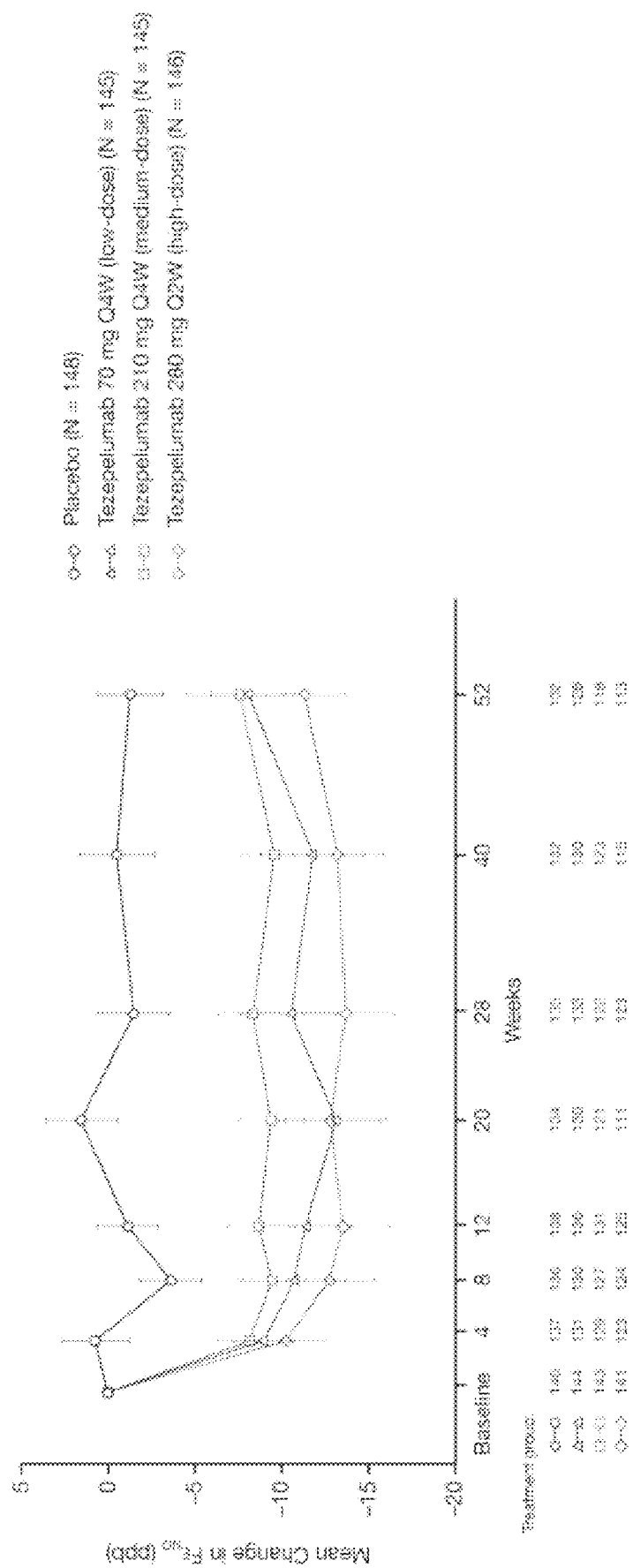

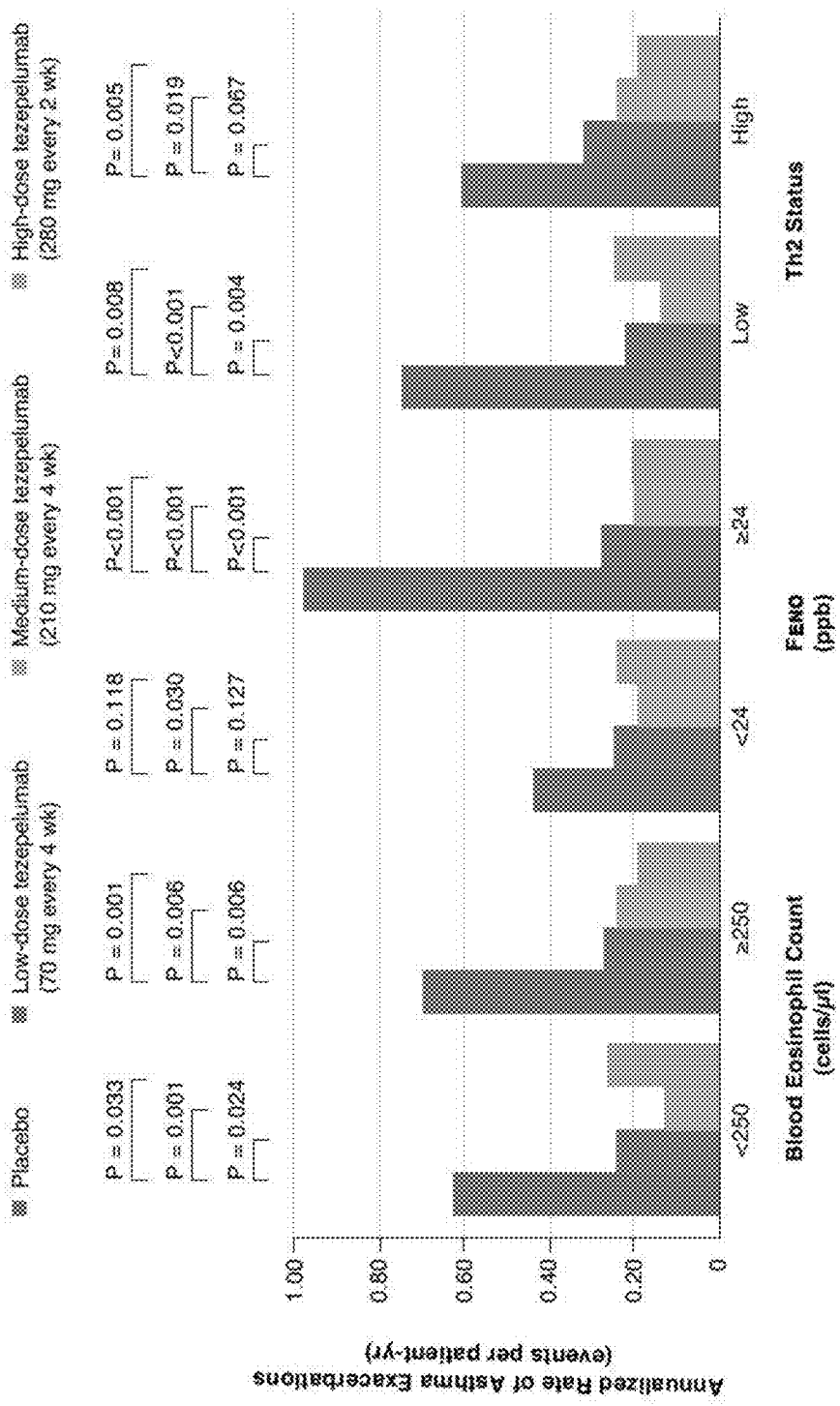
Figure 6A. Subpopulation analysis

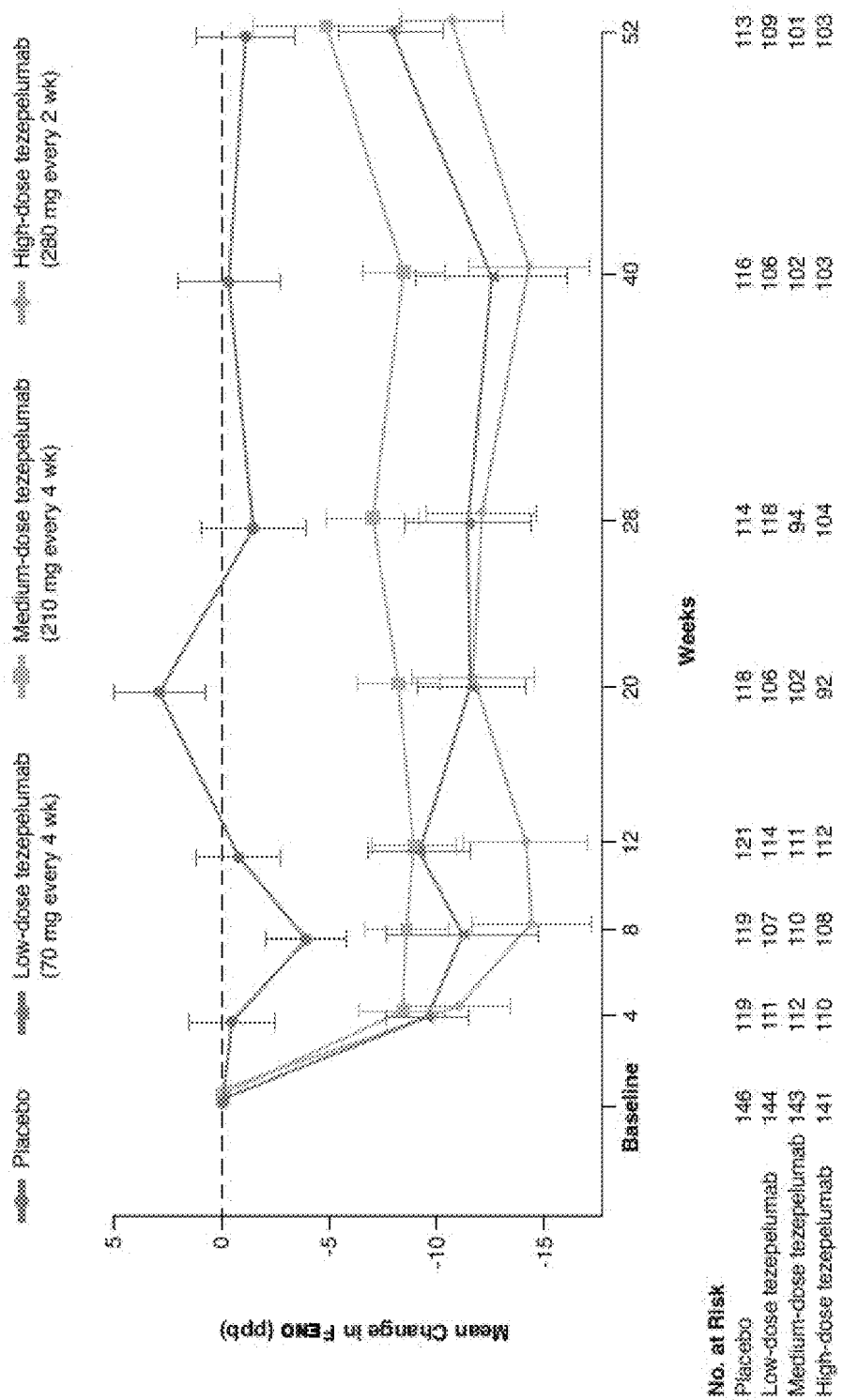
Figure 6B. Change FENO

Figure 7

Table 1A. Inclusion and Exclusion Criteria.

Inclusion criteria

Age 18-75 years, inclusive at the time of visit 1 (week −5).

Written informed consent and any locally required authorization (e.g., Health Insurance Portability and Accountability Act [HIPAA] in the USA, European Union [EU] Data Privacy Directive in the EU) obtained from the patient/legal representative prior to performing any protocol-related procedures, including screening evaluations.

Body mass index between 18-40 $kg/m^2$, inclusive, and weight ≥40 kg at visit 1 (week −5).

Documented physician-diagnosed asthma for at least 12 months prior to visit 1 (week −5) and post-BD reversibility of $FEV_1$ ≥12% and ≥200 ml during screening. Documented history of post-BD $FEV_1$ reversibility in the past 12 months will be accepted in place of reversibility during screening.

For patients 65 years or older at visit 1 (week −5), a chest radiograph or chest computed tomography scan within 12 months prior to visit 1 (week −5) that, according to the investigator, is normal for an asthmatic patient and excludes significant alternative respiratory disease, is required.

Patients must have received a physician-prescribed asthma controller regimen with medium-dose plus LABA or high-dose inhaled glucocorticoid plus LABA for at least 6 months prior to visit 1 (week −5), and the dose of inhaled glucocorticoid must be stable for at least 15 days prior to visit 1 (week −5) and throughout the screening/run-in period.

- To be classified as being on high-dose inhaled glucocorticoid, the patients will be on a total daily dose of >500 μg fluticasone dry powder inhaler, or a total daily dose of >440 μg fluticasone MDI or equivalent.
- To be classified as being on medium-dose inhaled glucocorticoid, the patients will be on a total daily dose (sum of all inhaled glucocorticoid) of 250 to 500 μg fluticasone dry powder inhaler or a total daily dose of 220 to 440 μg fluticasone MDI or equivalent.
- Equivalent inhaled glucocorticoid doses will be based upon the GINA guidelines (GINA, 2012).

If on asthma controller medications in addition to inhaled glucocorticoid plus LABA, the dose of the other asthma controller medications (leukotriene receptor inhibitors, theophylline, secondary inhaled glucocorticoid, LAMA, cromones, or maintenance oral prednisone or equivalent, up to a maximum of 10 mg daily or 20 mg every other day for the maintenance treatment of asthma) must be stable for at least 15 days prior to visit 1 (week −5).

Patients must have a morning pre-BD $FEV_1$ value of ≥40% and ≤80% predicted at two screening visits. The first time must be at either visit 1 (week −5) or visit 2 (week −4), and the second time must be at visit 3 (week −1).

Patients must have an ACQ-6 score of ≥1.5 twice during screening. The first time must be at visit 1 (week −5). The second time may be at either week −2 (taken from home

Figure 7 cont'd recording on the ePRO device) or at visit 3 (week −1).

At visit 4 (week 0, day 1), patients must have at least one of the following over the previous seven days from the ePRO device:
- Two days with a daytime or night-time symptoms score ≥1 (ASMA); or
- ≥1 awakening due to asthma leading to rescue medication use; or
- Rescue/reliever SABA use >2 days.

Patients must have a documented history of at least 2 asthma exacerbation events OR at least 1 severe asthma exacerbation resulting in hospitalization (admission to the hospital for at least 24 hours) within the 12 months prior to visit 1 (week −5). To qualify as an asthma exacerbation event, administration of a burst of systemic glucocorticoids for at least 3 consecutive days must have been required for the treatment of the asthma exacerbation, or the asthma exacerbation resulted in an emergency department visit which led to systemic glucocorticoids for at least 3 consecutive days or hospitalization. For patients receiving maintenance oral glucocorticoids, a temporary doubling of the stable existing maintenance dose for at least three days qualifies.

If on allergen-specific immunotherapy, patients must be on a maintenance dose and schedule for at least two months prior to visit 1 (week −5).

Patients must meet the all of following criteria at visit 4 (week 0, day 1) prior to randomization:
- Patients must demonstrate acceptable inhaler, peak flow meter, and spirometry techniques during screening/run-in period (from visit 2 to visit 4).
- Patients must demonstrate ≥70% compliance with usual asthma controller inhaled glucocorticoid/LABA during the screening/run-in period (from visit 2 to visit 4) based on ASMA.
- Patients must demonstrate ≥80% compliance with required use of the ePRO device; 80% compliance is defined as completing the ASMA for any eight mornings and any eight evenings in the previous ten days of the screening/run-in period.

Females of childbearing potential who are sexually active with a nonsterilized male partner must use a highly effective method of contraception from the time informed consent is obtained and must agree to continue using such precautions through week 64 of the study; cessation of contraception after this point should be discussed with a responsible physician. Periodic abstinence, the rhythm method, and the withdrawal method are not acceptable methods of contraception.
- Females of childbearing potential are defined as those who are not surgically sterile (i.e., bilateral tubal ligation, bilateral oophorectomy, or complete hysterectomy) or postmenopausal (defined as 12 months with no menses without an alternative medical cause).
- A highly effective method of contraception is defined as one that results in a low failure rate (i.e., less than 1% per year) when used consistently and correctly. Acceptable methods of contraception include: Male condom plus spermicide, copper T intrauterine device, levonorgestrel-releasing intrauterine device, implants, hormone shot or injection, combined pill, mini pill, and patch.

Exclusion criteria

Diagnosis of vocal cord dysfunction, reactive airways dysfunction syndrome, hyperventilation and panic attacks, or other mimics of asthma.

An established diagnosis of occupational asthma.

Current smokers or patients with a smoking history of ≥10 pack years (number of pack years = number of cigarettes per day/20 × number of years smoked). Former smokers with

Figure 7 cont'd

<10 pack years must have stopped for at least 6 months to be eligible.

Previous medical history or evidence of an uncontrolled intercurrent illness that in the opinion of the investigator and/or medical monitor may compromise the safety of the patient in the study or interfere with evaluation of the investigational product or reduce the patient's ability to participate in the study. Patients with well-controlled comorbid disease (e.g., hypertension, hyperlipidemia, gastroesophageal reflux disease) on a stable treatment regimen for 15 days prior to visit 1 (week −5) are eligible.

Any concomitant respiratory disease that, in the opinion of the investigator and/or medical monitor, will interfere with the evaluation of the investigational product or interpretation of patient safety or study results (e.g., chronic obstructive pulmonary disease, cystic fibrosis, pulmonary fibrosis, bronchiectasis, allergic bronchopulmonary aspergillosis, Churg-Strauss syndrome).

Any clinically relevant abnormal findings in hematology, clinical chemistry, or urinalysis (laboratory results from visit 1 (week −5) and visit 3 (week −1)), physical examination, vital signs during the screening/run-in period which, in the opinion of the investigator, may put the patient at risk because of his/her participation in the study, or may influence the results of the study, or the patient's ability to participate in the study.

Evidence of active liver disease, including jaundice or aspartate transaminase, alanine transaminase, or alkaline phosphatase greater than twice the upper limit of normal (laboratory results from visit 1 (week −5) and visit 3 (week −1)).

History of cancer:
- Patients who have had basal cell carcinoma or in situ carcinoma of the cervix are eligible to participate in the study provided that curative therapy was completed at least 12 months prior to visit 1 (week −5)
- Patients who have had other malignancies are eligible provided that curative therapy was completed at least five years prior to visit 1 (week −5).

Acute upper or lower respiratory infections leading to antibiotics or antiviral medications within 15 days prior to visit 1 (week −5), during the screening/run-in period, or at visit 4 (week 0, day 1).

Evidence of a clinically significant infection, or receiving treatment with antibiotics or antiviral medications at visit 4 (week 0, day 1).

A helminth parasitic infection diagnosed within 24 weeks of visit 1 (week −5) that has not been treated, or has not responded to standard of care therapy.

Known history of active TB or a positive QFT-G test for TB during screening. Patients with a positive or indeterminate QFT-G result may be enrolled if they have ALL of the following:
- No symptoms of TB: productive, prolonged cough (>3 weeks); coughing up blood; fever; night sweats; unexplained appetite loss; unintentional weight loss
- No known exposure to a case of active TB after most recent prophylaxis (prophylaxis required only if positive)
- No evidence of active TB on chest radiograph within three months prior to the first dose of investigational product.

Patients with an indeterminate QFT-G result will have repeat QFT-G testing during the study (weeks 12, 28, 40, and 52).

Positive hepatitis B surface antigen, or hepatitis C virus antibody serology at screening, or a positive medical history for hepatitis B or C. Patients with a history of hepatitis B vaccination without history of hepatitis B are allowed to enrol.

Figure 7 cont'd

A positive human immunodeficiency virus test at screening or patient taking antiretroviral medications, as determined by medical history and/or patient's verbal report.

History of sensitivity to any component of the investigational product formulation or a history of drug or other allergy that, in the opinion of the investigator or medical monitor contraindicates their participation.

History of anaphylaxis to any biologic therapy.

History of documented immune complex disease (type 3 hypersensitivity reactions) to monoclonal antibody administration.

History of any known primary immunodeficiency disorder excluding asymptomatic selective immunoglobulin A or immunoglobulin G subclass deficiency.

Systemic glucocorticoid burst including taper within 15 days prior to visit 1 (week −5) or during the screening/run-in period.

Use of 5-lipoxygenase inhibitors (e.g., zileuton) within 15 days prior to visit 1 (week −5).

Use of immunosuppressive medication (e.g., methotrexate, troleandomycin, oral gold, cyclosporine, azathioprine, intramuscular long-acting depot glucocorticoid, or any experimental anti-inflammatory therapy) within three months prior to visit 1 (week −5). Chronic oral prednisone or equivalent up to a maximum of 10 mg daily or 20 mg every other day for the maintenance treatment of asthma is permitted.

Receipt of any of the following within 30 days prior to visit 1 (week −5)
 • Immunoglobulin or blood products.

Receipt of any investigational non-biologic agent within 30 days or 5 half-lives prior visit 1 (week −5), whichever is longer.

Receipt of any marketed (including omalizumab) or investigational biologic agent within 4 months or 5 half-lives prior to visit 1 (week −5), whichever is longer.

Pregnant, breastfeeding or lactating females.

History of chronic alcohol or drug abuse within 12 months prior to visit 1 (week −5).

Planned surgical procedures requiring general anesthesia or in-patient status for >1 day during the conduct of the study.

Unwillingness or inability to follow the procedures outlined in the protocol to week 64.

Concurrent enrollment in another clinical study involving an investigational treatment.

Receipt of any oral or ophthalmic β-adrenergic antagonists (e.g., propranolol) within 15 days prior to visit 1 (week −5).

Receipt of the Th2 cytokine inhibitor suplatast within 15 days prior to visit 1 (week −5).

Receipt of any live or attenuated vaccines within 15 days prior to visit 1 (week −5).

Figure 8

*Figure 8 (Table 1B). Baseline Demographics and Clinical Characteristics in the Intention-To-Treat Population.*

| Demographics | | Placebo (N = 148) | Low-dose tezepelumab (70 mg Q4W) (N = 145) | Medium-dose tezepelumab (210 mg Q4W) (N = 145) | High-dose tezepelumab (280 mg Q2W) (N = 146) | Tezepelumab Total (N = 436) |
|---|---|---|---|---|---|---|
| Age (years) | Mean (SD) | 52.2 (11.5) | 50.6 (12.4) | 52.6 (12.5) | 50.1 (12.2) | 51.1 (12.4) |
| Male sex | no. (%) | 48 (32.4) | 50 (34.5) | 54 (37.2) | 53 (36.3) | 157 (36.0) |
| Race | no. (%) | | | | | |
| Asian | | 6 (4.1) | 3 (2.1) | 5 (3.4) | 5 (3.4) | 13 (3.0) |
| Black | | 6 (4.1) | 4 (2.8) | 3 (2.1) | 8 (5.5) | 15 (3.4) |
| White | | 133 (89.9) | 138 (95.2) | 136 (93.8) | 129 (88.4) | 403 (92.4) |
| Other | | 2 (1.4) | 0 | 0 | 2 (1.4) | 2 (0.5) |
| BMI (kg/m$^2$) | Mean (SD) | 28.5 (5.5) | 28.3 (5.1) | 28.4 (4.9) | 27.7 (5.0) | 28.1 (5.0) |
| Former smoker | Yes/no, n | 16/132 | 25/120 | 35/110 | 28/118 | 88/348 |
| Clinical characteristics | | Placebo (N = 148) | Low-dose tezepelumab (N = 145) | Medium-dose tezepelumab (N = 145) | High-dose tezepelumab (N = 146) | Tezepelumab Total |

Figure 8 cont'd

| | | | | | | (N = 436) |
|---|---|---|---|---|---|---|
| Pre-BD FEV1 (L) | Mean (SD) | 1.83 (0.58) | 1.91 (0.66) | 1.83 (0.58) | 1.87 (0.60) | 1.87 (0.61) |
| FEV1 % predicted/ reversibility | Mean (SD) | 60.4 (13.6)/ 21.5 (18.9) | 60.7 (13.5)/ 23.7 (18.9) | 59.2 (12.4)/ 20.6 (18.6) | 59.3 (11.8)/ 23.1 (23.0) | 59.7 (12.6)/ 22.5 (20.3) |
| Mean ACQ-6* | Mean (SD) | 2.66 (0.67) | 2.76 (0.80) | 2.71 (0.81) | 2.63 (0.75) | 2.70 (0.78) |
| Overall AQLQ(S)+12† | Mean (SD) | 4.06 (0.86) | 4.14 (0.94) | 4.19 (0.90) | 4.09 (0.90) | 4.14 (0.91) |
| Asthma symptom score‡ | Mean (SD) | 1.72 (0.58) | 1.70 (0.63) | 1.76 (0.57) | 1.68 (0.61) | 1.72 (0.60) |
| Inhaled glucocorticoid dose level | Medium (%)/High (%) | 73 (49.3)/75 (50.7) | 71 (49.0)/74 (51.0) | 70 (48.3)/75 (51.7) | 72 (49.3)/74 (50.7) | 213 (48.9)/223 (51.1) |
| FEIA IgE | Positive (%)/Negative (%) | 83 (61.5)/52 (38.5) | 71 (53.0)/63 (47.0) | 80 (60.2)/53 (39.8) | 74 (55.2)/60 (44.8) | 225 (56.1)/176 (43.9) |
| Eosinophil count (cells/µl) | Mean (SD) | 366 (323) | 345 (284) | 359 (347) | 378 (423) | 361 (356) |
| | Median (min, max) | 270.0 (0, 1870) | 270.0 (10, 1600) | 275.0 (0, 3180) | 255.0 (0, 3990) | 270.0 (0, 3990) |
| | ≥250, no. (%) | 86 (58.1) | 85 (58.6) | 83 (57.2) | 85 (58.2) | 253 (58.0) |
| | <250, no. (%) | 62 (41.9) | 60 (41.4) | 62 (42.8) | 61 (41.8) | 183 (42.0) |
| Total serum IgE | Mean (SD) | 447 (1232) | 314 (870) | 464 (1366) | 344 (579) | 374 (992) |

Figure 8 cont'd

| | | | | | | |
|---|---|---|---|---|---|---|
| (IU/ml) | Median (min, max) | 135.0 (4, 11860) | 109.3 (2, 7423) | 135.4 (2, 11430) | 138.1 (2, 3814) | 126.8 (2, 11430) |
| Th2 status^ | Low, no. (%) | 71 (48.3) | 81 (56.3) | 76 (53.1) | 78 (53.8) | 235 (54.4) |
| | High, no. (%) | 76 (51.7) | 63 (43.8) | 67 (46.9) | 67 (46.2) | 197 (45.6) |
| F<sub>E</sub>NO (ppb) | (n) Mean (SD) | (146) 36.3 (38.9) | (144) 34.5 (46.9) | (143) 30.4 (29.4) | (141) 32.6 (33.9) | (428) 32.5 (37.5) |
| | Median (min, max) | 21.5 (3.5, 276.3) | 22.0 (2.5, 349.0) | 20.5 (4.0, 152.5) | 19.7 (2.0, 217.5) | 21.0 (2.0, 349.0) |
| | <24 ppb, no. (%) | 80 (54.8) | 77 (53.5) | 83 (58.0) | 79 (56.0) | 239 (55.8) |
| | ≥24 ppb, no. (%) | 66 (45.2) | 67 (46.5) | 60 (42.0) | 62 (44.0) | 189 (44.2) |
| Number of asthma exacerbations in the past 12 months | 1 or 2(%)/ ≥3(%) | 120 (81.1)/28 (18.9) | 116 (80.0)/29 (20.0) | 113 (77.9)/32 (22.1) | 126 (86.3)/20 (13.7) | 355 (81.4)/81 (18.6) |

*Mean ACQ-6 score: ≤0.75 = well-controlled; >0.75 and <1.5 = partly controlled; ≥1.5 = uncontrolled.

†Mean AQLQ(S) score: 7 = no impairment; 1 = severe impairment.

‡Asthma symptom score ranges from zero (no symptom) to 4 (worst possible symptom) and includes daytime severity, daytime frequency, and night time severity.

^Th2-high: IgE > 100 IU/ml and blood eosinophil count ≥140 cells/μl.

§A clinically meaningful cutoff of 24 ppb was used for the $F_{E_{NO}}$ sub-population analysis.[2,3]

ACQ, Asthma Control Questionnaire; AQLQ(S)+12, asthma quality of life questionnaire; BD, bronchodilator; BMI, body mass index; $F_{E_{NO}}$, fractional exhaled nitric oxide; FEIA, fluorescent immunoassay; $FEV_1$, forced expiratory volume in 1 second; IgE, immunoglobulin E; Th2, T helper 2; Q4W, every 4 weeks; Q2W, every 2 weeks; SD, standard deviation.

Figure 9

*Figure 9 (Table 2) - Annualized Asthma Exacerbation Rate Reduction, and Change from Baseline in FEV₁, ACQ and AQLQ in the Eosinophil Sub-Populations <250 cells/μl and ≥250 cells/μl.*

| | Placebo (N = 148) | Low-dose tezepelumab (70 mg Q4W) (N = 145) | Medium-dose tezepelumab (210 mg Q4W) (N = 145) | High-dose tezepelumab (280 mg Q2W) (N = 146) |
|---|---|---|---|---|
| ≥250 Eosinophils per μl | | | | |
| n | 86 | 85 | 83 | 85 |
| Annualized AER (95% CI) | 0.70 (0.54, 0.91) | 0.27 (0.17, 0.41) | 0.24 (0.14, 0.38) | 0.19 (0.11, 0.31) |
| Reduction vs placebo (95% CI) | - | 62% (24%, 81%) | 65% (26%, 84%) | 73% (41%, 88%) |
| P-value* | - | 0.006 | 0.006 | 0.001 |
| n | 84 | 82 | 72 | 72 |
| LS mean percentage change from baseline at week 52 in Pre-BD FEV₁ (L) | 0.67 | 10.88 | 10.27 | 14.57 |
| Difference vs placebo (95% CI) P-value* | - | 10.21 (2.74, 17.69) 0.008 | 9.60 (1.91, 17.29) 0.015 | 13.91 (6.28, 21.53) <0.001 |
| LS mean change from baseline at week 52 in Pre-BD FEV₁ (L) | -0.03 | 0.12 | 0.10 | 0.17 |
| Difference vs placebo (95% CI) P-value* | - | 0.15 (0.03, 0.27) 0.017 | 0.13 (0.01, 0.26) 0.041 | 0.20 (0.07, 0.32) 0.002 |
| n | 68 | 70 | 60 | 56 |
| LS mean ACQ-6 change from baseline at week 50 | -0.86 | -1.07 | -1.29 | -1.15 |
| Difference vs placebo (95% CI) P-value* | - | -0.22 (-0.51, 0.08) 0.152 | -0.43 (-0.74, -0.13) 0.005 | -0.29 (-0.59, 0.01) 0.062 |

Figure 9 cont'd

| | | | | |
|---|---|---|---|---|
| n | 62 | 69 | 54 | 55 |
| LS mean AQLQ(S)+12 change from baseline at week 48[†] | 0.87 | 1.04 | 1.23 | 1.18 |
| Difference vs placebo (95% CI) P-value[*] | - | 0.17 (−0.16, 0.49) 0.312 | 0.36 (0.02, 0.70) 0.036 | 0.31 (−0.03, 0.64) 0.071 |
| <250 Eosinophils per μl | | | | |
| n | 62 | 60 | 62 | 61 |
| Annualized AER (95% CI) | 0.63 (0.45, 0.87) | 0.24 (0.13, 0.41) | 0.13 (0.06, 0.26) | 0.26 (0.14, 0.43) |
| Reduction vs placebo (95% CI) | - | 59% (11%, 81%) | 79% (46%, 91%) | 56% (7%, 80%) |
| P-value[*] | - | 0.024 | 0.001 | 0.033 |
| n | 57 | 55 | 56 | 53 |
| LS mean percentage change from baseline at week 52 in Pre-BD FEV$_1$ (L) | −3.20 | 1.04 | 2.94 | 2.09 |
| Difference vs placebo (95% CI) P-value[*] | - | 4.25 (−4.71, 13.21) 0.351 | 6.14 (−2.69, 14.97) 0.172 | 5.30 (−3.64, 14.24) 0.244 |
| LS mean change from baseline at week 52 in Pre-BD FEV$_1$ (L) | −0.08 | −0.02 | 0.01 | 0.02 |
| Difference vs placebo (95% CI) P-value[*] | - | 0.06 (−0.09, 0.20) 0.464 | 0.08 (−0.06, 0.23) 0.268 | 0.09 (−0.06, 0.24) 0.231 |
| n | 44 | 47 | 50 | 47 |
| LS mean ACQ-6 change from baseline at week 50 | −0.91 | −1.09 | −1.16 | −1.29 |
| Difference vs placebo (95% CI) P-value[*] | - | −0.18 (−0.52, 0.15) 0.284 | −0.25 (−0.58, 0.09) 0.147 | −0.38 (−0.72, −0.04) 0.028 |
| n | 43 | 42 | 43 | 45 |
| LS mean AQLQ(S)+12 change from baseline at week 48[†] | 0.92 | 1.00 | 1.18 | 1.43 |

Figure 9 cont'd

| Difference vs placebo (95% CI) P-value* | 0.07 (-0.26, 0.41) 0.667 | 0.26 (-0.08, 0.60) 0.131 | 0.51 (0.17, 0.85) 0.003 |

*P-values are nominal and without multiplicity adjustment.

†A substantially lower proportion of patients completed the eDiary at week 52 than at weeks 48 and 50 due to a programming flaw within the eDiary which prevented patients from completing all of the questionnaires at week 52.

$FEV_1$: increase in value indicates improvement. MCID: 100 ml to 200 ml.

ACQ-6: range: 0–6. Decrease in value indicates improvement. MCID: 0.5.

AQLQ: range: 1–7. Increase in value indicates improvement. MCID: 0.5.

AER, asthma exacerbation rate; ACQ, Asthma Control Questionnaire; AQLQ(S)+12, asthma quality of life questionnaire; BD, bronchodilator; CI, confidence interval; $FEV_1$, forced expiratory volume in 1 second; LS mean, least squares mean; Q4W, every 4 weeks; Q2W, every 2 weeks.

Figure 10

Figure 10 (Table 3) - Change from Baseline in ACQ-6 (week 50) and AQLQ(S)+12 (week 48) in the Intention-to-Treat Population

| | Placebo (N = 148) | Low-dose tezepelumab (70 mg Q4W) (N = 145) | Medium-dose tezepelumab (210 mg Q4W) (N = 145) | High-dose tezepelumab (280 mg Q2W) (N = 146) |
|---|---|---|---|---|
| n | 112 | 117 | 110 | 103 |
| LS mean ACQ-6 change from baseline at week 50 | −0.88 | −1.08 | −1.23 | −1.21 |
| Difference vs placebo (95% CI) | - | −0.20 (−0.42, 0.02) | −0.34 (−0.57, −0.12) | −0.33 (−0.56, −0.10) |
| P-value* | - | 0.077 | 0.003 | 0.004 |
| n | 105 | 111 | 97 | 100 |
| LS mean AQLQ(S)+12 change from baseline at week 48 | 0.89 | 1.02 | 1.21 | 1.29 |
| Difference vs placebo (95% CI) | - | 0.13 (−0.10, 0.37) | 0.32 (0.08, 0.56) | 0.40 (0.16, 0.64) |
| P-value* | - | 0.268 | 0.009 | 0.001 |

Figure 11

*Figure 11 (Table 4) - Annualized Asthma Exacerbation Rate Reduction and Change from Baseline in $FEV_1$ (week 52), ACQ-6 (week 50), and AQLQ(S)+12 (week 48) in Patient Sub-populations: Th2 status, Serum Periostin.*

| | Placebo (N = 148) | | Low-dose tezepelumab (70 mg Q4W) (N = 145) | | Medium-dose tezepelumab (210 mg Q4W) (N = 145) | | High-dose tezepelumab (280 mg Q2W) (N = 146) | |
|---|---|---|---|---|---|---|---|---|
| Th2 status (High = IgE >100 IU/ml and eosinophil count ≥140 cells/µl; Low = IgE ≤100 IU/ml or eosinophil count <140 cells/µl) | | | | | | | | |
| | High | Low | High | Low | High | Low | High | Low |
| Annualized AER | | | | | | | | |
| n | 76 | 71 | 63 | 81 | 67 | 76 | 67 | 78 |
| AER | 0.61 | 0.75 | 0.32 | 0.22 | 0.24 | 0.14 | 0.19 | 0.25 |
| (95% CI) | (0.45, 0.81) | (0.56, 0.98) | (0.20, 0.50) | (0.13, 0.35) | (0.13, 0.40) | (0.07, 0.26) | (0.10, 0.34) | (0.15, 0.39) |
| AER reduction vs placebo (95% CI) | - | - | 51% (-5%, 78%) | 65% (29%, 83%) | 63% (15%, 83%) | 82% (58%, 92%) | 71% (31%, 87%) | 63% (22%, 82%) |
| P-value* | - | - | 0.067 | 0.004 | 0.019 | <0.001 | 0.005 | 0.008 |
| Pre-BD $FEV_1$ (L) | | | | | | | | |
| n | 74 | 66 | 60 | 76 | 59 | 67 | 58 | 66 |

Figure 11 cont'd

| | | | | | | | | |
|---|---|---|---|---|---|---|---|---|
| percent change from baseline (week 52) | LS mean | 1.85 | -2.04 | 8.79 | 7.52 | 9.55 | 6.61 | 16.25 | 6.44 |
| | Difference vs placebo | - | - | 6.93 | 9.56 | 7.70 | 8.66 | 14.40 | 8.48 |
| | (95% CI) | | | (-1.96, 15.83) | (2.05, 17.07) | (-1.11, 16.50) | (0.97, 16.34) | (5.54, 23.25) | (0.80, 16.17) |
| | P-value* | | | 0.126 | 0.013 | 0.087 | 0.027 | 0.002 | 0.031 |
| Pre-BD FEV$_1$ (L) change from baseline (week 52) | LS mean | -0.05 | -0.03 | 0.04 | 0.12 | 0.04 | 0.09 | 0.18 | 0.08 |
| | Difference vs placebo | - | - | 0.09 | 0.15 | 0.09 | 0.13 | 0.23 | 0.11 |
| | (95% CI) | | | (-0.06, 0.23) | (0.03, 0.27) | (-0.05, 0.24) | (0.00, 0.25) | (0.09, 0.38) | (-0.01, 0.24) |
| | P-value* | | | 0.231 | 0.018 | 0.207 | 0.053 | 0.002 | 0.076 |
| ACQ-6 (week 50)† | n | 64 | 47 | 54 | 62 | 52 | 56 | 46 | 56 |
| | LS mean | -1.00 | -0.69 | -1.06 | -1.08 | -1.29 | -1.13 | -1.20 | -1.18 |
| | Difference vs placebo | - | - | -0.06 | -0.38 | -0.30 | -0.43 | -0.20 | -0.49 |
| | (95% CI) | | | (-0.37, 0.26) | (-0.70, -0.06) | (-0.61, 0.02) | (-0.76, -0.11) | (-0.52, 0.12) | (-0.81, -0.16) |
| | P-value* | | | 0.725 | 0.019 | 0.065 | 0.009 | 0.224 | 0.003 |
| AQLQ(S)+12 (week | n | 60 | 44 | 52 | 58 | 45 | 51 | 45 | 54 |

Figure 11 cont'd

| 48† | | High | Low | High | Low | High | Low | High | Low |
|---|---|---|---|---|---|---|---|---|---|
| | LS mean | 1.08 | 0.61 | 1.17 | 0.89 | 1.18 | 1.19 | 1.19 | 1.33 |
| | Difference vs placebo | - | - | 0.08 | 0.28 | 0.09 | 0.58 | 0.10 | 0.72 |
| | (95% CI) | - | - | (-0.26, 0.42) | (-0.06, 0.61) | (-0.25, 0.44) | (0.23, 0.92) | (-0.24, 0.45) | (0.38, 1.07) |
| | P-value* | - | - | 0.632 | 0.104 | 0.595 | 0.001 | 0.556 | <0.001 |
| Serum periostin (High => Median, Low =< Median) | | | | | | | | | |
| | | High | Low | High | Low | High | Low | High | Low |
| Annualized AER | n | 72 | 76 | 65 | 79 | 79 | 65 | 74 | 69 |
| | AER | 0.75 | 0.60 | 0.28 | 0.25 | 0.18 | 0.22 | 0.20 | 0.25 |
| | (95% CI) | (0.56, 0.98) | (0.43, 0.80) | (0.16, 0.44) | (0.15, 0.39) | (0.09, 0.30) | (0.11, 0.37) | (0.11, 0.33) | (0.14, 0.41) |
| | AER reduction vs placebo (95% CI) | - | - | 68% (29%, 85%) | 55% (9%, 78%) | 78% (53%, 90%) | 60% (2%, 84%) | 73% (43%, 88%) | 56% (3%, 80%) |
| | P-value* | - | - | 0.005 | 0.027 | <0.001 | 0.045 | <0.001 | 0.041 |
| Pre-BD FEV₁ (L) percent change from baseline (week 52) | n | 70 | 71 | 63 | 73 | 71 | 56 | 67 | 55 |
| | LS mean | -0.46 | 1.40 | 11.69 | 6.82 | 14.03 | 2.48 | 14.34 | 6.33 |
| | Difference vs placebo | - | - | 12.15 | 5.42 | 14.49 | 1.09 | 14.80 | 4.93 |

Figure 11 cont'd

| | | | | | | | | |
|---|---|---|---|---|---|---|---|---|
| (95% CI) | - | - | (2.84, 21.46) | (-1.10, 11.93) | (5.58, 23.40) | (-5.83, 8.00) | (5.78, 23.82) | (-1.91, 11.77) |
| P-value* | - | - | 0.011 | 0.103 | 0.002 | 0.758 | 0.001 | 0.157 |
| Pre-BD FEV$_1$ (L) change from baseline (week 52) | | | | | | | | |
| LS mean | -0.01 | -0.03 | 0.15 | 0.06 | 0.17 | -0.01 | 0.19 | 0.08 |
| Difference vs. placebo | - | - | 0.16 | 0.09 | 0.18 | 0.02 | 0.20 | 0.10 |
| (95% CI) | - | - | (0.02, 0.30) | (-0.03, 0.22) | (0.05, 0.32) | (-0.11, 0.15) | (0.06, 0.34) | (-0.02, 0.23) |
| P-value* | - | - | 0.029 | 0.128 | 0.008 | 0.755 | 0.005 | 0.108 |
| ACQ-6 (week 50)† | | | | | | | | |
| n | 60 | 52 | 56 | 60 | 58 | 51 | 55 | 46 |
| LS mean | -0.89 | -0.87 | -1.01 | -1.13 | -1.46 | -0.94 | -1.18 | -1.26 |
| Difference vs. placebo | - | - | -0.12 | -0.25 | -0.57 | -0.06 | -0.29 | -0.39 |
| (95% CI) | - | - | (-0.44, 0.21) | (-0.56, 0.05) | (-0.89, -0.26) | (-0.38, 0.26) | (-0.61, 0.03) | (-0.71, -0.06) |
| P-value* | - | - | 0.475 | 0.101 | <0.001 | 0.694 | 0.076 | 0.019 |
| AQLQ(S)+12 (week 48)† | | | | | | | | |
| n | 59 | 46 | 53 | 57 | 47 | 49 | 55 | 43 |
| LS mean | 0.89 | 0.90 | 1.01 | 1.01 | 1.40 | 0.99 | 1.29 | 1.28 |
| Difference vs. placebo | - | - | 0.13 | 0.10 | 0.52 | 0.09 | 0.40 | 0.38 |

| (95% CI) | (-0.22, 0.48) | (-0.22, 0.43) | (0.17, 0.86) | (-0.25, 0.42) | (0.06, 0.74) | (0.04, 0.72) |
|---|---|---|---|---|---|---|
| P-value* | 0.470 | 0.524 | 0.004 | 0.621 | 0.020 | 0.028 |

Figure 12 (Table 5) *Annualized Asthma Exacerbation Rate Reduction and Change from Baseline in FEV₁ (week 52), ACQ-6 (week 50), and AQLQ(S)+12 (week 48) in Patient Sub-populations: FE$_{NO}$, Allergic status, Current post-BD reversibility*

| FE$_{NO}$ <24 ppb and ≥24 ppb | | Placebo (N = 148) | | Low-dose tezepelumab (70 mg Q4W) (N = 145) | | Medium-dose tezepelumab (210 mg Q4W) (N = 145) | | High-dose tezepelumab (280 mg Q2W) (N = 146) | |
|---|---|---|---|---|---|---|---|---|---|
| | | ≥24 ppb | <24 ppb | ≥24 ppb | <24 ppb | ≥24 ppb | <24 ppb | ≥24 ppb | <24 ppb |
| Annualized AER | n | 66 | 80 | 67 | 77 | 60 | 83 | 62 | 79 |
| | AER | 0.98 | 0.44 | 0.28 | 0.25 | 0.20 | 0.19 | 0.21 | 0.24 |
| | (95% CI) | (0.75, 1.25) | (0.31, 0.61) | (0.17, 0.44) | (0.15, 0.39) | (0.10, 0.35) | (0.11, 0.32) | (0.11, 0.36) | (0.14, 0.38) |
| | AER reduction vs placebo (95% CI) | - | - | 72% (43%, 86%) | 43% (-18%, 73%) | 77% (50%, 90%) | 62% (9%, 84%) | 78% (53%, 90%) | 46% (-17%, 75%) |
| | p-value* | - | - | <0.001 | 0.127 | <0.001 | 0.030 | <0.001 | 0.118 |
| Pre-BD FEV₁ (L) percent | n | 61 | 78 | 61 | 75 | 52 | 74 | 52 | 69 |

Figure 12 cont'd

| | | | | | | | | | |
|---|---|---|---|---|---|---|---|---|---|
| change from baseline (week 52) | LS mean | −1.55 | 1.93 | 8.51 | 7.99 | 12.09 | 6.47 | 11.18 | 10.51 |
| | Difference vs placebo | − | − | 10.06 | 6.06 | 13.64 | 4.55 | 12.73 | 8.59 |
| | (95% CI) | − | − | (0.72, 19.40) | (−1.08, 13.21) | (3.95, 23.33) | (−2.55, 11.64) | (3.09, 22.37) | (1.37, 15.80) |
| | P-value* | − | − | 0.035 | 0.096 | 0.006 | 0.208 | 0.010 | 0.020 |
| Pre-BD FEV$_1$ (L) change from baseline (week 52) | LS mean | −0.05 | 0.05 | 0.10 | 0.13 | 0.15 | 0.09 | 0.14 | 0.17 |
| | Difference vs placebo | − | − | 0.15 | 0.08 | 0.21 | 0.04 | 0.20 | 0.12 |
| | (95% CI) | − | − | (0.00, 0.31) | (−0.03, 0.20) | (0.05, 0.37) | (−0.07, 0.16) | (0.04, 0.36) | (0.00, 0.23) |
| | P-value* | − | − | 0.050 | 0.164 | 0.011 | 0.449 | 0.015 | 0.046 |
| ACQ-6 (week 50) | n | 50 | 62 | 52 | 64 | 48 | 60 | 48 | 60 |
| | LS mean | −0.83 | −0.89 | −1.18 | −1.03 | −1.50 | −0.99 | −1.27 | −1.15 |
| | Difference vs placebo | − | − | −0.35 | −0.14 | −0.67 | −0.10 | −0.44 | −0.26 |
| | (95% CI) | − | − | (−0.69, −0.01) | (−0.43, 0.15) | (−1.02, −0.32) | (−0.39, 0.19) | (−0.79, −0.08) | (−0.55, 0.04) |
| | P-value* | − | − | 0.046 | 0.348 | <0.001 | 0.507 | 0.016 | 0.086 |
| AQLQ(S)+12 (week | n | 49 | 56 | 49 | 62 | 44 | 51 | 39 | 58 |

Figure 12 cont'd

| 48)† | | Allergic | Non-allergic | Allergic | Non-allergic | Allergic | Non-allergic | Allergic | Non-allergic |
|---|---|---|---|---|---|---|---|---|---|
| | LS mean | 0.83 | 0.96 | 1.06 | 0.99 | 1.48 | 0.97 | 1.21 | 1.33 |
| | Difference vs placebo | - | - | 0.24 | 0.04 | 0.65 | 0.02 | 0.39 | 0.38 |
| | (95% CI) | - | - | (-0.13, 0.60) | (-0.27, 0.35) | (0.27, 1.03) | (-0.30, 0.33) | (0.01, 0.77) | (0.07, 0.69) |
| | P-value* | - | - | 0.204 | 0.805 | <0.001 | 0.911 | 0.047 | 0.017 |

Allergic status (allergic/non-allergic)

| | | Allergic | Non-allergic | Allergic | Non-allergic | Allergic | Non-allergic | Allergic | Non-allergic |
|---|---|---|---|---|---|---|---|---|---|
| Annualized AER | n | 83 | 52 | 71 | 63 | 80 | 53 | 74 | 60 |
| | AER | 0.73 | 0.62 | 0.24 | 0.21 | 0.13 | 0.24 | 0.22 | 0.21 |
| | (95% CI) | (0.55, 0.94) | (0.43, 0.88) | (0.14, 0.38) | (0.11, 0.37) | (0.06, 0.25) | (0.13, 0.42) | (0.12, 0.36) | (0.11, 0.37) |
| | AER reduction vs placebo (95% CI) | - | - | 66% (25%, 85%) | 67% (29%, 84%) | 82% (56%, 93%) | 57% (3%, 81%) | 66% (26%, 85%) | 64% (17%, 84%) |
| | P-value* | - | - | 0.008 | 0.004 | <0.001 | 0.043 | 0.007 | 0.017 |
| Pre-BD FEV₁ (L) Percent change from baseline | n | 78 | 50 | 68 | 59 | 73 | 44 | 60 | 54 |
| | LS mean | -0.52 | -3.38 | 11.61 | 3.00 | 8.35 | 8.15 | 6.52 | 8.55 |

Figure 12 cont'd

| | | | | | | | | |
|---|---|---|---|---|---|---|---|---|
| (week 52) | Difference vs placebo | - | - | 12.13 | 6.38 | 8.87 | 11.54 | 7.04 | 11.93 |
| | (95% CI) | - | - | (4.07, 20.18) | (-2.49, 15.25) | (0.99, 16.75) | (2.20, 20.87) | (-1.04, 15.11) | (2.86, 21.00) |
| | P-value* | - | - | 0.003 | 0.157 | 0.028 | 0.016 | 0.087 | 0.010 |
| Pre-BD $FEV_1$ (L) change from baseline (week 52) | LS mean | -0.04 | -0.04 | 0.14 | 0.06 | 0.08 | 0.13 | 0.07 | 0.17 |
| | Difference vs placebo | - | - | 0.18 | 0.09 | 0.12 | 0.17 | 0.11 | 0.20 |
| | (95% CI) | - | - | (0.05, 0.31) | (-0.06, 0.25) | (-0.01, 0.25) | (0.01, 0.33) | (-0.03, 0.24) | (0.05, 0.36) |
| | P-value* | - | - | 0.008 | 0.230 | 0.071 | 0.040 | 0.110 | 0.011 |
| ACQ-6 (week 50)† | n | 66 | 39 | 60 | 50 | 62 | 40 | 50 | 45 |
| | LS Mean | -0.99 | -0.76 | -1.18 | -0.96 | -1.24 | -1.18 | -1.31 | -1.25 |
| | Difference vs placebo | - | - | -0.19 | -0.21 | -0.25 | -0.42 | -0.32 | -0.49 |
| | (95% CI) | - | - | (-0.49, 0.12) | (-0.56, 0.15) | (-0.54, 0.05) | (-0.80, -0.05) | (-0.63, -0.01) | (-0.85, -0.12) |
| | P-value* | - | - | 0.227 | 0.253 | 0.106 | 0.027 | 0.041 | 0.009 |
| AQLQ(S)+12 (week 48)† | n | 63 | 35 | 57 | 47 | 57 | 34 | 49 | 43 |
| | LS mean | 1.05 | 0.53 | 1.15 | 0.88 | 1.18 | 1.20 | 1.20 | 1.44 |

Figure 12 cont'd

|  |  | Yes | No | Yes | No | Yes | No | Yes | No |
|---|---|---|---|---|---|---|---|---|---|
|  | Difference vs placebo | 0.09 | - | - | 0.35 | 0.13 | 0.66 | 0.15 | 0.91 |
|  | (95% CI) | - | - | (-0.22, 0.41) | (-0.04, 0.73) | (-0.19, 0.44) | (0.25, 1.08) | (-0.17, 0.47) | (0.51, 1.30) |
|  | P-value* | - | - | 0.555 | 0.078 | 0.427 | 0.002 | 0.367 | <0.001 |

Current post-BD reversibility (Yes [≥12% and ≥200 ml] or No [<12% and <200 ml])

|  |  | Yes | No | Yes | No | Yes | No | Yes | No |
|---|---|---|---|---|---|---|---|---|---|
| Annualized AER | n | 135 | 13 | 129 | 16 | 121 | 24 | 134 | 12 |
|  | AER | 0.56 | 1.85 | 0.25 | 0.38 | 0.16 | 0.37 | 0.20 | 0.44 |
|  | (95% CI) | (0.44, 0.70) | (1.18, 2.75) | (0.17, 0.35) | (0.14, 0.83) | (0.09, 0.25) | (0.16, 0.73) | (0.13, 0.29) | (0.14, 1.03) |
|  | AER reduction vs placebo (95% CI) | - | - | 57% (24%, 75%) | 83% (57%, 93%) | 72% (46%, 85%) | 79% (45%, 92%) | 65% (37%, 80%) | 74% (13%, 92%) |
|  | P-value* | - | - | 0.003 | <0.001 | <0.001 | 0.001 | <0.001 | 0.029 |
| Pre-BD FEV$_1$ (L) percent change from baseline (week 52) | n | 129 | 12 | 123 | 14 | 108 | 20 | 114 | 11 |
|  | LS mean | -1.08 | -4.44 | 7.60 | 4.35 | 6.98 | 11.70 | 8.97 | 13.15 |
|  | Difference vs placebo | - | - | 8.68 | 8.79 | 8.06 | 16.14 | 10.05 | 17.59 |

Figure 12 cont'd

| | Col1 | Col2 | Col3 | Col4 | Col5 | Col6 | Col7 | Col8 |
|---|---|---|---|---|---|---|---|---|
| (95% CI) | - | - | (2.48, 14.88) | (-2.75, 20.32) | (1.69, 14.43) | (4.75, 27.53) | (3.79, 16.30) | (4.97, 30.22) |
| P-value* | | | 0.006 | 0.133 | 0.013 | 0.006 | 0.002 | 0.007 |
| Pre-BD FEV$_1$ (L) change from baseline (week 52) | | | | | | | | |
| LS mean | -0.07 | -0.10 | 0.06 | 0.02 | 0.03 | 0.16 | 0.08 | 0.21 |
| Difference vs placebo | - | - | 0.13 | 0.12 | 0.11 | 0.26 | 0.15 | 0.31 |
| (95% CI) | - | - | (0.03, 0.23) | (-0.08, 0.33) | (0.00, 0.21) | (0.06, 0.46) | (0.05, 0.25) | (0.08, 0.53) |
| P-value* | - | - | 0.013 | 0.226 | 0.045 | 0.013 | 0.005 | 0.008 |
| ACQ-6 (week 50)† | | | | | | | | |
| n | 104 | 8 | 103 | 14 | 91 | 19 | 92 | 11 |
| LS mean | -0.87 | -1.11 | -1.08 | -1.10 | -1.13 | -1.73 | -1.21 | -1.33 |
| Difference vs placebo | - | - | -0.21 | 0.01 | -0.26 | -0.62 | -0.34 | -0.22 |
| (95% CI) | - | - | (-0.44, 0.03) | (-0.66, 0.68) | (-0.50, -0.02) | (-1.26, 0.02) | (-0.57, -0.10) | (-0.93, 0.50) |
| P-value* | - | - | 0.085 | 0.980 | 0.034 | 0.057 | 0.006 | 0.555 |
| AQLQ(S)+12 (week 48)† | | | | | | | | |
| n | 98 | 7 | 98 | 13 | 79 | 18 | 89 | 11 |
| LS mean | 0.89 | 0.98 | 1.00 | 1.22 | 1.19 | 1.38 | 1.28 | 1.39 |
| Difference vs placebo | - | - | 0.11 | 0.24 | 0.30 | 0.40 | 0.39 | 0.41 |

Figure 12 cont'd

| (95% CI) | - | (−0.14, 0.35) | (−0.50, 0.98) | (0.04, 0.56) | (−0.29, 1.10) | (0.14, 0.64) | (−0.36, 1.18) |
|---|---|---|---|---|---|---|---|
| P-value* | - | 0.405 | 0.520 | 0.026 | 0.256 | 0.003 | 0.296 |

Figure 13

Figure 13 (Table 6) *Change from Baseline in Post-BD FEV₁ and Pre- and Post-BD Forced Vital Capacity at Week 52 in the Intention-To-Treat population*

| | | Placebo (N = 148) | Low-dose tezepelumab (70 mg Q4W) (N = 145) | Medium-dose tezepelumab (210 mg Q4W) (N = 145) | High-dose tezepelumab (280 mg Q2W) (N = 146) |
|---|---|---|---|---|---|
| Post-BD FEV₁ (L) | | | | | |
| Change from baseline | n | 140 | 137 | 128 | 124 |
| | Mean | −0.05 | 0.11 | 0.08 | 0.11 |
| | SD | 0.35 | 0.39 | 0.45 | 0.42 |
| | Median | −0.02 | 0.04 | 0.04 | 0.04 |
| | (Min, max) | (−1.31, 0.94) | (−0.76, 2.31) | (−1.04, 2.68) | (−1.10, 1.37) |
| Percentage change from baseline | n | 140 | 137 | 128 | 124 |
| | Mean | −1.35 | 6.14 | 6.69 | 7.43 |

Figure 13 cont'd

|  |  |  |  |  |  |
|---|---|---|---|---|---|
| SD | 16.33 | 20.19 | 27.35 | 22.52 |  |
| Median | -1.07 | 1.46 | 1.32 | 2.11 |  |
| (Min, max) | (-45.92, 51.16) | (-26.77, 126.23) | (-30.54, 188.73) | (-37.50, 118.35) |  |
| Pre-BD FVC (L) |  |  |  |  |  |
| Change from baseline |  |  |  |  |  |
| n | 141 | 137 | 128 | 125 |  |
| Mean | 0.08 | 0.24 | 0.19 | 0.20 |  |
| SD | 0.47 | 0.55 | 0.60 | 0.48 |  |
| Median | 0.03 | 0.12 | 0.09 | 0.08 |  |
| (Min, max) | (-1.25, 2.03) | (-0.85, 2.39) | (-2.22, 2.58) | (-0.91, 2.14) |  |
| Percentage change from baseline |  |  |  |  |  |
| n | 141 | 137 | 128 | 125 |  |
| Mean | 3.81 | 10.14 | 8.95 | 8.34 |  |
| SD | 18.02 | 23.25 | 25.45 | 19.88 |  |

Figure 13 cont'd

|  |  |  |  |  |  |
|---|---|---|---|---|---|
| Median | 1.22 | 4.35 | 3.65 | 3.36 |
| (Min, max) | (−32.76, 84.62) | (−30.83, 134.52) | (−49.12, 133.73) | (−22.81, 110.88) |
| Post-BD FVC (L) | | | | |
| Change from baseline n | 140 | 137 | 128 | 124 |
| Mean | −0.07 | 0.08 | 0.09 | 0.07 |
| SD | 0.36 | 0.43 | 0.50 | 0.43 |
| Median | −0.05 | 0.05 | 0.03 | 0.01 |
| (Min, max) | (−1.69, 1.03) | (−0.76, 2.23) | (−1.32, 2.28) | (−0.94, 1.81) |
| Percentage change from baseline n | 140 | 137 | 128 | 124 |
| Mean | −1.57 | 3.43 | 4.26 | 2.93 |
| SD | 11.73 | 17.45 | 19.14 | 14.49 |
| Median | −1.30 | 1.29 | 0.90 | 0.13 |
| (Min, max) | (−50.60, 47.69) | (−22.44, 117.99) | (−29.91, 125.97) | (−26.22, 85.38) |

Figure 14

*Figure 14 (Table 7) Annualized Rate of Severe Asthma Exacerbations, Time to First Asthma Exacerbation/Severe Asthma Exacerbation, and Proportion of Patients With One or More Asthma Exacerbation at Week 52 in the Intention-To-Treat population*

| | Placebo (N = 148) | Low-dose tezepelumab (70 mg Q4W) (N = 145) | Medium-dose tezepelumab (210 mg Q4W) (N = 145) | High-dose tezepelumab (280 mg Q2W) (N = 146) |
|---|---|---|---|---|
| Annualized rate of severe asthma exacerbations | | | | |
| Severe asthma exacerbation rate | 0.13 | 0.04 | 0.02 | 0.03 |
| (95% CI) | (0.08, 0.20) | (0.01, 0.08) | (0.00, 0.06) | (0.01, 0.07) |
| Reduction vs placebo | - | 72% | 85% | 74% |
| (95% CI) | - | (-6%, 93%) | (27%, 97%) | (-10%, 94%) |
| P-value | | 0.060 | 0.019 | 0.067 |
| Time to asthma exacerbations | | | | |
| Event | 43 | 30 | 21 | 25 |
| Censored | 105 | 115 | 124 | 121 |

Figure 14 cont'd

| | | | | |
|---|---|---|---|---|
| Hazard ratio | | 0.66 | 0.46 | 0.55 |
| 95% CI | | 0.41, 1.05 | 0.27, 0.78 | 0.34, 0.90 |
| P-value* | | 0.078 | 0.003 | 0.018 |

Time to severe exacerbations

| | | | | |
|---|---|---|---|---|
| Event | | 9 | 5 | 3 | 4 |
| Censored | | 139 | 140 | 142 | 142 |
| Hazard ratio | | - | 0.55 | 0.34 | 0.45 |
| 95% CI | | - | 0.18, 1.64 | 0.09, 1.24 | 0.14, 1.47 |
| P-value* | | - | 0.284 | 0.085 | 0.168 |

Patients with asthma exacerbations/severe asthma exacerbations

| Patients with ≥1 asthma exacerbation, n (%) | | | | |
|---|---|---|---|---|
| Yes | 43 (29.1) | 30 (20.7) | 21 (14.5) | 25 (17.1) |
| No | 105 (70.9) | 115 (79.3) | 124 (85.5) | 121 (82.9) |
| P-value* | - | 0.098 | 0.003 | 0.015 |

Figure 14 cont'd

| Patients with ≥1 severe asthma exacerbation, n (%) | Yes | 9 (6.1) | 5 (3.4) | 3 (2.1) | 4 (2.7) |
|---|---|---|---|---|---|
| | No | 139 (93.9) | 140 (96.6) | 142 (97.9) | 142 (97.3) |
| | P-value* | - | 0.291 | 0.083 | 0.163 |

Figure 15

Figure 15 (Table 8) *Post-hoc Analysis of Annualized Asthma Exacerbation Rate Reduction Stratified by Blood Eosinophil Count <400 cells/μL vs ≥400 cells/μL Through Week 52*

| | | Placebo (N = 148) | | Low-dose tezepelumab (70 mg Q4W) (N = 145) | | Medium-dose tezepelumab (210 mg Q4W) (N = 145) | | High-dose tezepelumab (280 mg Q2W) (N = 146) | |
|---|---|---|---|---|---|---|---|---|---|
| Eosinophils per μL | | <400 | ≥400 | <400 | ≥400 | <400 | ≥400 | <400 | ≥400 |
| Annualized AER | n | 98 | 50 | 100 | 45 | 100 | 45 | 96 | 50 |
| | AER | 0.59 | 0.84 | 0.24 | 0.32 | 0.19 | 0.19 | 0.27 | 0.13 |
| | (95% CI) | (0.44, 0.76) | (0.61, 1.14) | (0.15, 0.35) | (0.17, 0.53) | (0.11, 0.30) | (0.08, 0.37) | (0.17, 0.40) | (0.05, 0.27) |
| | AER reduction vs placebo (95% CI) | - | - | 60% (24%, 79%) | 58% (0%, 82%) | 68% (34%, 84%) | 75% (31%, 91%) | 53% (11%, 75%) | 84% (53%, 95%) |
| | P-value* | - | - | 0.005 | 0.050 | 0.002 | 0.007 | 0.021 | <0.001 |

*P-values are nominal and without multiplicity adjustment.

AER, asthma exacerbation rate; CI, confidence interval; Q4W, every 4 weeks; Q2W, every 2 weeks

Figure 16

Figure 16 [Table 9] *Annualized Asthma Exacerbation Rate Reduction Stratified by Patients on a Medium- or High-Dose of Inhaled Glucocorticoid and by Patients on Maintenance Oral Glucocorticoids Through Week 52*

| Inhaled glucocorticoid dose | | Placebo (N = 148) | | Low-dose tezepelumab (70 mg Q4W) (N = 145) | | Medium-dose tezepelumab (210 mg Q4W) (N = 145) | | High-dose tezepelumab (280 mg Q2W) (N = 146) | |
|---|---|---|---|---|---|---|---|---|---|
| | | Medium inhaled glucocorticoid | High inhaled glucocorticoid | Medium inhaled glucocorticoid | High inhaled glucocorticoid | Medium inhaled glucocorticoid | High inhaled glucocorticoid | Medium inhaled glucocorticoid | High inhaled glucocorticoid |
| Annualized AER | n | 73 | 75 | 71 | 74 | 70 | 75 | 72 | 74 |
| | AER | 0.38 | 0.96 | 0.19 | 0.33 | 0.15 | 0.23 | 0.20 | 0.24 |
| | (95% CI) | (0.26, 0.55) | (0.75, 1.22) | (0.10, 0.32) | (0.21, 0.49) | (0.07, 0.28) | (0.13, 0.37) | (0.10, 0.34) | (0.14, 0.39) |
| | AER reduction vs placebo (95% CI) | - | - | 51% (-8%, 78%) | 66% (33%, 83%) | 60% (5%, 83%) | 76% (49%, 89%) | 49% (-13%, 77%) | 75% (47%, 88%) |
| | P-value* | - | - | 0.076 | 0.002 | 0.038 | <0.001 | 0.096 | <0.001 |
| Maintenance oral glucocorticoid use | | Yes | No | Yes | No | Yes | No | Yes | No |

Figure 16 cont'd

| Annualized AER | | | | | | | | |
|---|---|---|---|---|---|---|---|---|
| n | 14 | 134 | 15 | 130 | 9 | 136 | 13 | 133 |
| AER | 2.08 | 0.54 | 0.61 | 0.22 | 0.51 | 0.17 | 0.24 | 0.22 |
| (95% CI) | (1.37, 3.03) | (0.42, 0.68) | (0.28, 1.16) | (0.15, 0.32) | (0.14, 1.32) | (0.11, 0.26) | (0.05, 0.70) | (0.14, 0.32) |
| AER reduction vs placebo (95% CI) | - | - | 72% (31%, 89%) | 59% (25%, 77%) | 75% (11%, 93%) | 68% (40%, 83%) | 88% (49%, 97%) | 59% (27%, 77%) |
| P-value* | - | - | 0.006 | 0.003 | 0.033 | <0.001 | 0.004 | 0.003 |

Figure 17

*Figure 17 (Table 10) Annualized Asthma Exacerbation Rate Reduction Stratified by Number of Prior Asthma Exacerbations and by Smoking History* Through Week 52*

| | Placebo (N = 148) | | Low-dose tezepelumab (70 mg Q4W) (N = 145) | | Medium-dose tezepelumab (210 mg Q4W) (N = 145) | | High-dose tezepelumab (280 mg Q2W) (N = 146) | |
|---|---|---|---|---|---|---|---|---|
| Number of prior asthma exacerbations in the previous 12 months | 1 or 2 | ≥3 | 1 or 2 | ≥3 | 1 or 2 | ≥3 | 1 or 2 | ≥3 |
| Annualized AER | | | | | | | | |
| n | 120 | 28 | 116 | 29 | 113 | 32 | 126 | 20 |
| AER | 0.34 | 2.13 | 0.18 | 0.60 | 0.10 | 0.52 | 0.18 | 0.48 |

Figure 17 cont'd

|  | Former smoker | Non-smoker | Former smoker | Non-smoker | Former smoker | Non-smoker | Former smoker | Non-smoker |
|---|---|---|---|---|---|---|---|---|
| (95% CI) | (0.24, 0.46) | (1.62, 2.75) | (0.11, 0.27) | (0.35, 0.95) | (0.05, 0.18) | (0.29, 0.85) | (0.11, 0.27) | (0.22, 0.91) |
| AER reduction vs placebo (95% CI) | - | - | 49% (-1%, 74%) | 70% (45%, 84%) | 70% (34%, 87%) | 75% (51%, 87%) | 50% (3%, 75%) | 74% (43%, 88%) |
| P-value† |  |  | 0.052 | <0.001 | 0.003 | <0.001 | 0.040 | <0.001 |
| Smoking history | Former smoker | Non-smoker | Former smoker | Non-smoker | Former smoker | Non-smoker | Former smoker | Non-smoker |
| Annualized AER  n | 16 | 132 | 25 | 120 | 35 | 110 | 28 | 118 |
| AER | 0.72 | 0.67 | 0.53 | 0.20 | 0.18 | 0.19 | 0.25 | 0.21 |
| (95% CI) | (0.36, 1.29) | (0.53, 0.82) | (0.28, 0.90) | (0.13, 0.30) | (0.07, 0.40) | (0.12, 0.30) | (0.09, 0.53) | (0.14, 0.32) |
| AER reduction vs placebo (95% CI) | - | - | 28% (-72%, 70%) | 69% (42%, 83%) | 72% (19%, 90%) | 70% (41%, 85%) | 61% (-13%, 87%) | 67% (39%, 83%) |
| P-value† |  |  | 0.455 | <0.001 | 0.018 | <0.001 | 0.083 | <0.001 |

Figure 18

*Figure 18 (Table 11) Change from Baseline in MedImmune ASMA Score at week 52*

| | Placebo (N = 148) | Low-dose tezepelumab (70 mg Q4W) (N = 145) | Medium-dose tezepelumab (210 mg Q4W) (N = 145) | High-dose tezepelumab (280 mg Q2W) (N = 146) |
|---|---|---|---|---|
| Overall intention-to-treat population | | | | |
| n | 128 | 125 | 113 | 112 |
| LS mean | −0.53 | −0.60 | −0.67 | −0.74 |
| Difference vs placebo | - | −0.07 | −0.13 | −0.21 |
| 95% CI | - | (−0.21, 0.07) | (−0.28, 0.01) | (−0.35, −0.06) |
| P-value* | - | 0.329 | 0.067 | 0.005 |
| Eosinophils (per μl) | ≥250 | ≥250 | ≥250 | ≥250 |
| | <250 | <250 | <250 | <250 |
| n | 78 | 77 | 65 | 63 |
| | 50 | 48 | 48 | 49 |
| LS mean | −0.56 | −0.61 | −0.74 | −0.75 |
| | −0.51 | −0.60 | −0.58 | −0.73 |

Figure 18 cont'd

| | | | | | | | | |
|---|---|---|---|---|---|---|---|---|
| Difference vs placebo | - | - | -0.06 | -0.09 | -0.18 | -0.08 | -0.20 | -0.22 |
| (95% CI) | | | (-0.25, 0.13) | (-0.30, 0.13) | (-0.38, 0.01) | (-0.29, 0.14) | (-0.39, 0.00) | (-0.44, 0.00) |
| P-value* | | | 0.539 | 0.431 | 0.068 | 0.493 | 0.047 | 0.045 |

Th2 Status (High = IgE >100 IU/ml and eosinophil count ≥140 cells/ul; Low = IgE ≤100 IU/ml or eosinophil count <140 cells/ul)

| | High | Low | High | Low | High | Low | High | Low |
|---|---|---|---|---|---|---|---|---|
| n | 66 | 61 | 55 | 69 | 53 | 58 | 53 | 58 |
| LS mean | -0.55 | -0.50 | -0.67 | -0.55 | -0.59 | -0.72 | -0.76 | -0.73 |
| Difference vs placebo | - | - | -0.12 | -0.05 | -0.05 | -0.23 | -0.21 | -0.23 |
| (95% CI) | | | (-0.32, 0.08) | (-0.26, 0.16) | (-0.25, 0.15) | (-0.44, -0.02) | (-0.41, -0.02) | (-0.44, -0.02) |
| P-value* | | | 0.229 | 0.639 | 0.631 | 0.036 | 0.035 | 0.032 |

FE$_{NO}$ <24 ppb and ≥24 ppb

| | ≥24 ppb | <24 ppb | ≥24 ppb | <24 ppb | ≥24 ppb | <24 ppb | ≥24 ppb | <24 ppb |
|---|---|---|---|---|---|---|---|---|
| n | 57 | 70 | 55 | 69 | 44 | 67 | 42 | 66 |
| LS mean | -0.49 | -0.53 | -0.68 | -0.54 | -0.76 | -0.59 | -0.74 | -0.71 |

Figure 18 cont'd

| | | | | | | | | |
|---|---|---|---|---|---|---|---|---|
| Difference vs placebo | | | −0.19 | −0.01 | −0.27 | −0.06 | −0.25 | −0.18 |
| (95% CI) | | | (−0.40, 0.02) | (−0.21, 0.18) | (−0.50, −0.05) | (−0.26, 0.13) | (−0.47, −0.03) | (−0.37, 0.02) |
| P-value* | | | 0.082 | 0.915 | 0.016 | 0.511 | 0.027 | 0.074 |
| Serum periostin (High => Median, Low =< Median) | | | | | | | | |
| | High | Low | High | Low | High | Low | High | Low |
| n | 66 | 62 | 59 | 65 | 62 | 50 | 58 | 51 |
| LS mean | −0.51 | −0.55 | −0.57 | −0.60 | −0.82 | −0.47 | −0.74 | −0.74 |
| Difference vs placebo | | | −0.05 | −0.06 | −0.31 | 0.08 | −0.23 | −0.19 |
| (95% CI) | | | (−0.26, 0.16) | (−0.25, 0.14) | (−0.51, −0.10) | (−0.13, 0.28) | (−0.43, −0.02) | (−0.39, 0.01) |
| P-value* | | | 0.619 | 0.569 | 0.003 | 0.464 | 0.030 | 0.058 |
| Allergic status (allergic/non-allergic) | | | | | | | | |
| | Allergic | Non-allergic | Allergic | Non-allergic | Allergic | Non-allergic | Allergic | Non-allergic |
| n | 69 | 48 | 59 | 57 | 63 | 39 | 51 | 49 |

Figure 18 cont'd

| | Yes | No | Yes | No | Yes | No | Yes | No |
|---|---|---|---|---|---|---|---|---|
| LS mean | -0.53 | -0.51 | -0.59 | -0.59 | -0.63 | -0.68 | -0.67 | -0.86 |
| Difference vs placebo | - | - | -0.07 | -0.09 | -0.10 | -0.17 | -0.15 | -0.36 |
| (95% CI) | - | - | (-0.26, 0.13) | (-0.31, 0.14) | (-0.29, 0.09) | (-0.41, 0.07) | (-0.34, 0.05) | (-0.59, -0.13) |
| P-value* | - | - | 0.500 | 0.453 | 0.300 | 0.162 | 0.144 | 0.002 |

Current post-BD reversibility (Yes [≥12% and ≥200 ml] or no [<12% and <200 ml])

| | Yes | No | Yes | No | Yes | No | Yes | No |
|---|---|---|---|---|---|---|---|---|
| n | 117 | 11 | 112 | 13 | 94 | 19 | 101 | 11 |
| LS mean | -0.55 | -0.35 | -0.59 | -0.63 | -0.63 | -0.87 | -0.73 | -0.84 |
| Difference vs placebo | - | - | -0.04 | -0.28 | -0.07 | -0.52 | -0.18 | -0.49 |
| (95% CI) | - | - | (-0.19, 0.11) | (-0.69, 0.13) | (-0.23, 0.08) | (-0.91, -0.14) | (-0.33, -0.03) | (-0.93, -0.05) |
| P-value* | - | - | 0.580 | 0.183 | 0.348 | 0.008 | 0.022 | 0.030 |

Figure 19

*Figure 19 (Table 12). All Treatment-Emergent Serious Adverse Events in the As-Treated Population*

| Patients* with at least one serious adverse event | Placebo (N = 148) | Low-dose tezepelumab (70 mg Q4W) (N = 145) | Medium-dose tezepelumab (210 mg Q4W) (N = 145) | High-dose tezepelumab (280 mg Q2W) (N = 146) | Tezepelumab Total (N = 436) |
|---|---|---|---|---|---|
| Cardiac disorders | 2 (1.4%) | 2 (1.4%) | 1 (0.7%) | 0 | 3 (0.7%) |
| Atrial fibrillation | 1 (0.7%) | 0 | 0 | 0 | 0 |
| Atrial flutter | 0 | 1 (0.7%) | 0 | 0 | 1 (0.2%) |
| Cardiac failure | 1 (0.7%) | 0 | 1 (0.7%) | 0 | 1 (0.2%) |
| Myocardial infarction | 0 | 1 (0.7%) | 0 | 0 | 1 (0.2%) |
| Gastrointestinal disorders | 1 (0.7%) | 1 (0.7%) | 0 | 3 (2.1%) | 4 (0.9%) |
| Abdominal pain | 0 | 1 (0.7%) | 0 | 0 | 1 (0.2%) |
| Abdominal pain lower | 1 (0.7%) | 0 | 0 | 0 | 0 |
| Hiatus hernia | 0 | 0 | 0 | 1 (0.7%) | 1 (0.2%) |
| Large intestinal polyp | 0 | 0 | 0 | 1 (0.7%) | 1 (0.2%) |
| Pancreatitis acute | 0 | 0 | 0 | 1 (0.7%) | 1 (0.2%) |
| General disorders and administration site | 1 (0.7%) | 0 | 1 (0.7%) | 0 | 1 (0.2%) |

Figure 19 cont'd

| conditions | | | | | |
|---|---|---|---|---|---|
| Non-cardiac chest pain | 1 (0.7%) | 0 | 1 (0.7%) | 0 | 1 (0.2%) |
| Hepatobiliary disorders | 0 | 0 | 0 | 1 (0.7%) | 1 (0.2%) |
| Cholelithiasis | 0 | 0 | 0 | 1 (0.7%) | 1 (0.2%) |
| Immune system disorders | 0 | 0 | 0 | 1 (0.7%) | 1 (0.2%) |
| Anaphylactic shock | 0 | 0 | 0 | 1 (0.7%) | 1 (0.2%) |
| Infections and infestations | 4 (2.7%) | 6 (4.1%) | 1 (0.7%) | 4 (2.7%) | 11 (2.5%) |
| Bronchitis | 0 | 1 (0.7%) | 0 | 0 | 1 (0.2%) |
| Cellulitis | 1 (0.7%) | 0 | 0 | 0 | 0 |
| Chronic sinusitis | 1 (0.7%) | 1 (0.7%) | 0 | 0 | 1 (0.2%) |
| Erysipelas | 0 | 0 | 0 | 1 (0.7%) | 1 (0.2%) |
| Genitourinary tract infection | 0 | 0 | 0 | 1 (0.7%) | 1 (0.2%) |
| Influenza | 0 | 1 (0.7%) | 0 | 0 | 1 (0.2%) |
| Pneumonia | 1 (0.7%) | 3 (2.1%) | 0 | 2 (1.4%) | 5 (1.1%) |
| Pyelonephritis chronic | 0 | 1 (0.7%) | 0 | 0 | 1 (0.2%) |
| Sinusitis | 1 (0.7%) | 0 | 0 | 0 | 0 |
| Staphylococcal infection | 0 | 0 | 1 (0.7%) | 0 | 1 (0.2%) |

Figure 19 cont'd

| | | | | |
|---|---|---|---|---|
| Tooth abscess | 1 (0.7%) | | | 0 |
| Urinary tract infection | 0 | 1 (0.7%) | 0 | 1 (0.2%) |
| Viral infection | 0 | 0 | 1 (0.7%) | 1 (0.2%) |
| Injury, poisoning and procedural complications | 0 | 2 (1.4%) | 2 (1.4%) | 6 (1.4%) |
| Cartilage injury | 0 | 0 | 1 (0.7%) | 1 (0.2%) |
| Concussion | 0 | 0 | 0 | 1 (0.2%) |
| Foreign body aspiration | 0 | 0 | 1 (0.7%) | 1 (0.2%) |
| Ligament sprain | 0 | 0 | 1 (0.7%) | 1 (0.2%) |
| Lower limb fracture | 0 | 1 (0.7%) | 0 | 1 (0.2%) |
| Lumbar vertebral fracture | 0 | 0 | 1 (0.7%) | 1 (0.2%) |
| Post procedural complication | 0 | 1 (0.7%) | 0 | 1 (0.2%) |
| Upper limb fracture | 0 | 1 (0.7%) | 0 | 1 (0.2%) |
| Musculoskeletal and connective tissue disorders | 1 (0.7%) | 0 | 3 (2.1%) | 4 (0.9%) |
| Intervertebral disc protrusion | 0 | 0 | 1 (0.7%) | 1 (0.2%) |
| Osteoarthritis | 1 (0.7%) | 0 | 1 (0.7%) | 1 (0.2%) |
| Osteochondrosis | 0 | 0 | 0 | 1 (0.2%) |
| Rhabdomyolysis | 0 | 0 | 1 (0.7%) | 1 (0.2%) |

Figure 19 cont'd

| | | | | |
|---|---|---|---|---|
| Neoplasms benign, malignant and unspecified (including cysts and polyps) | 1 (0.7%) | 0 | 3 (2.1%) | 5 (1.1%) |
| Adenocarcinoma of colon | 0 | 0 | 0 | 1 (0.2%) |
| Basal cell carcinoma | 0 | 0 | 1 (0.7%) | 1 (0.2%) |
| Lipoma | 0 | 0 | 0 | 1 (0.2%) |
| Pancreatic carcinoma metastatic | 0 | 0 | 1 (0.7%) | 1 (0.2%) |
| Prostate cancer | 1 (0.7%) | 0 | 1 (0.7%) | 1 (0.2%) |
| Nervous system disorders | 0 | 2 (1.4%) | 2 (1.4%) | 4 (0.9%) |
| Cerebrovascular accident ("stroke") | 0 | 1 (0.7%) | 0 | 1 (0.2%) |
| Cervicobrachial syndrome | 0 | 0 | 1 (0.7%) | 1 (0.2%) |
| Guillain-Barré syndrome | 0 | 0 | 1 (0.7%) | 1 (0.2%) |
| Sciatica | 0 | 1 (0.7%) | 0 | 1 (0.2%) |
| Pregnancy, puerperium and perinatal conditions | 0 | 0 | 1 (0.7%) | 2 (0.5%) |
| Abortion threatened | 0 | 0 | 1 (0.7%) | 2 (0.5%) |
| Hyperemesis gravidarum | 0 | 0 | 1 (0.7%) | 1 (0.2%) |
| Renal and urinary disorders | 0 | 1 (0.7%) | 0 | 1 (0.2%) |
| Calculus urinary | 0 | 1 (0.7%) | 0 | 1 (0.2%) |

Figure 19 cont'd

| Reproductive system and breast disorders | 0 | 1 (0.7%) | 0 | 2 (1.4%) | 3 (0.7%) |
|---|---|---|---|---|---|
| Cervical leukoplakia | 0 | 0 | 0 | 1 (0.7%) | 1 (0.2%) |
| Ovarian cyst | 0 | 0 | 0 | 1 (0.7%) | 1 (0.2%) |
| Testicular pain | 0 | 1 (0.7%) | 0 | 0 | 1 (0.2%) |
| Respiratory, thoracic and mediastinal disorders | 10 (6.8%) | 6 (4.1%) | 4 (2.8%) | 6 (4.1%) | 16 (3.7%) |
| Asthma | 10 (6.8%) | 5 (3.4%) | 4 (2.8%) | 6 (4.1%) | 15 (3.4%) |
| Pulmonary embolism | 0 | 1 (0.7%) | 0 | 0 | 1 (0.2%) |
| Skin and subcutaneous tissue disorders | 1 (0.7%) | 1 (0.7%) | 0 | 0 | 1 (0.2%) |
| Dermatitis atopic | 1 (0.7%) | 0 | 0 | 0 | 0 |
| Dermatitis contact | 0 | 1 (0.7%) | 0 | 0 | 1 (0.2%) |
| Vascular disorders | 0 | 1 (0.7%) | 1 (0.7%) | 1 (0.7%) | 3 (0.7%) |
| Deep vein thrombosis | 0 | 1 (0.7%) | 1 (0.7%) | 0 | 2 (0.5%) |
| Hypertensive crisis | 0 | 0 | 0 | 1 (0.7%) | 1 (0.2%) |

SEQUENCE LISTING

```
<160> NUMBER OF SEQ ID NOS: 106

<210> SEQ ID NO 1
<211> LENGTH: 743
<212> TYPE: DNA
<213> ORGANISM: Homo Sapiens
<220> FEATURE:
<221> NAME/KEY: misc_feature
<223> OTHER INFORMATION: TSLP
<220> FEATURE:
<221> NAME/KEY: CDS
<222> LOCATION: (200)..(676)

<400> SEQUENCE: 1
gcagccagaa agctctggag catcagggag actccaactt aaggcaacag catgggtgaa      60
taagggcttc ctgtggactg gcaatgagag gcaaaacctg gtgcttgagc actggcccct     120
aaggcaggcc ttacagatct cttacactcg tggtgggaag agtttagtgt gaaactgggg     180
tggaattggg tgtccacgt atg ttc cct ttt gcc tta cta tat gtt ctg tca     232
                       Met Phe Pro Phe Ala Leu Leu Tyr Val Leu Ser
                         1               5                  10 gtt tct ttc agg aaa atc ttc atc tta caa ctt gta ggg ctg gtg tta      280
Val Ser Phe Arg Lys Ile Phe Ile Leu Gln Leu Val Gly Leu Val Leu
         15                  20                  25 act tac gac ttc act aac tgt gac ttt gag aag att aaa gca gcc tat      328
Thr Tyr Asp Phe Thr Asn Cys Asp Phe Glu Lys Ile Lys Ala Ala Tyr
     30                  35                  40 ctc agt act att tct aaa gac ctg att aca tat atg agt ggg acc aaa      376
Leu Ser Thr Ile Ser Lys Asp Leu Ile Thr Tyr Met Ser Gly Thr Lys
 45                  50                  55 agt acc gag ttc aac aac acc gtc tct tgt agc aat cgg cca cat tgc      424
Ser Thr Glu Phe Asn Asn Thr Val Ser Cys Ser Asn Arg Pro His Cys
60                  65                  70                  75 ctt act gaa atc cag agc cta acc ttc aat ccc acc gcc ggc tgc gcg      472
Leu Thr Glu Ile Gln Ser Leu Thr Phe Asn Pro Thr Ala Gly Cys Ala
                 80                  85                  90 tcg ctc gcc aaa gaa atg ttc gcc atg aaa act aag gct gcc tta gct      520
Ser Leu Ala Lys Glu Met Phe Ala Met Lys Thr Lys Ala Ala Leu Ala
             95                 100                 105
```

```
atc tgg tgc cca ggc tat tcg gaa act cag ata aat gct act cag gca    568
Ile Trp Cys Pro Gly Tyr Ser Glu Thr Gln Ile Asn Ala Thr Gln Ala
        110             115             120 atg aag aag agg aga aaa agg aaa gtc aca acc aat aaa tgt ctg gaa    616
Met Lys Lys Arg Arg Lys Arg Lys Val Thr Thr Asn Lys Cys Leu Glu
125             130             135 caa gtg tca caa tta caa gga ttg tgg cgt cgc ttc aat cga cct tta    664
Gln Val Ser Gln Leu Gln Gly Leu Trp Arg Arg Phe Asn Arg Pro Leu
140             145             150             155 ctg aaa caa cag taaaccatct ttattatggt catatttcac agcccaaaat        716
Leu Lys Gln Gln aaatcatctt tattaagtaa aaaaaaa                                      743

<210> SEQ ID NO 2
<211> LENGTH: 159
<212> TYPE: PRT
<213> ORGANISM: Homo Sapiens

<400> SEQUENCE: 2

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln
145                 150                 155

<210> SEQ ID NO 3
<211> LENGTH: 11
<212> TYPE: PRT
<213> ORGANISM: Homo Sapiens
<220> FEATURE:
<221> NAME/KEY: MISC_FEATURE
<223> OTHER INFORMATION: LCDR1

<400> SEQUENCE: 3

Gly Gly Asn Asn Leu Gly Ser Lys Ser Val His
1               5                   10

<210> SEQ ID NO 4
<211> LENGTH: 7
<212> TYPE: PRT
<213> ORGANISM: Homo Sapiens
<220> FEATURE:
<221> NAME/KEY: MISC_FEATURE
<223> OTHER INFORMATION: LCDR2

<400> SEQUENCE: 4
```

Asp Asp Ser Asp Arg Pro Ser
1               5

<210> SEQ ID NO 5
<211> LENGTH: 11
<212> TYPE: PRT
<213> ORGANISM: Homo Sapiens
<220> FEATURE:
<221> NAME/KEY: MISC_FEATURE
<223> OTHER INFORMATION: LCDR3

<400> SEQUENCE: 5

Gln Val Trp Asp Ser Ser Ser Asp His Val Val
1               5                   10

<210> SEQ ID NO 6
<211> LENGTH: 5
<212> TYPE: PRT
<213> ORGANISM: Homo Sapiens
<220> FEATURE:
<221> NAME/KEY: MISC_FEATURE
<223> OTHER INFORMATION: HCDR1

<400> SEQUENCE: 6

Thr Tyr Gly Met His
1               5

<210> SEQ ID NO 7
<211> LENGTH: 17
<212> TYPE: PRT
<213> ORGANISM: Homo Sapiens
<220> FEATURE:
<221> NAME/KEY: MISC_FEATURE
<223> OTHER INFORMATION: HCDR2

<400> SEQUENCE: 7

Val Ile Trp Tyr Asp Gly Ser Asn Lys His Tyr Ala Asp Ser Val Lys
1               5                   10                  15

Gly

<210> SEQ ID NO 8
<211> LENGTH: 13
<212> TYPE: PRT
<213> ORGANISM: Homo Sapiens
<220> FEATURE:
<221> NAME/KEY: MISC_FEATURE
<223> OTHER INFORMATION: HCDR3

<400> SEQUENCE: 8

Ala Pro Gln Trp Glu Leu Val His Glu Ala Phe Asp Ile
1               5                   10

<210> SEQ ID NO 9
<211> LENGTH: 366
<212> TYPE: DNA
<213> ORGANISM: Homo Sapiens
<220> FEATURE:
<221> NAME/KEY: misc_feature
<223> OTHER INFORMATION: Heavy Chain VH

<400> SEQUENCE: 9
cagatgcagc tggtggagtc tgggggaggc gtggtccagc ctggggaggtc cctgagactc      60 tcctgtgcag cgtctggatt caccttcaga acctatggca tgcactgggt ccgccaggct     120
ccaggcaagg gactggagtg ggtggcagtt atatggtatg atggaagtaa taaacactat     180

```
gcagactccg tgaagggccg attcaccatc accagagaca attccaagaa cactctgaat    240
ctgcaaatga acagcctgag agccgaggac acggctgtgt attactgtgc gagagcccct    300
cagtgggagc tagttcatga agcttttgat atctggggcc aagggacaat ggtcaccgtc    360
tcttca                                                               366
```

<210> SEQ ID NO 10
<211> LENGTH: 122
<212> TYPE: PRT
<213> ORGANISM: Homo Sapiens
<220> FEATURE:
<221> NAME/KEY: MISC_FEATURE
<223> OTHER INFORMATION: Heavy Chain VH

<400> SEQUENCE: 10

```
Gln Met Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Thr Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Ala Pro Gln Trp Glu Leu Val His Glu Ala Phe Asp Ile Trp
            100                 105                 110

Gly Gln Gly Thr Met Val Thr Val Ser Ser
        115                 120
```

<210> SEQ ID NO 11
<211> LENGTH: 325
<212> TYPE: DNA
<213> ORGANISM: Homo Sapiens
<220> FEATURE:
<221> NAME/KEY: misc_feature
<223> OTHER INFORMATION: Light Chain VL

<400> SEQUENCE: 11

```
tcctatgtgc tgactcagcc accctcggtg tcagtggccc caggacagac ggccaggatt    60
acctgtgggg gaaacaacct tggaagtaaa agtgtgcact ggtaccagca gaagccaggc    120
caggcccctg tgctggtcgt ctatgatgat agcgaccggc cctcatggat ccctgagcga    180
ttctctggct ccaactctgg gaacacggcc accctgacca tcagcagggg cgaagccggg    240
gatgaggccg actattactg tcaggtgtgg gatagtagta gtgatcatgt ggtatttcgg    300
cggagggacc aagctgaccg tccta                                          325
```

<210> SEQ ID NO 12
<211> LENGTH: 108
<212> TYPE: PRT
<213> ORGANISM: Homo Sapiens
<220> FEATURE:
<221> NAME/KEY: MISC_FEATURE
<223> OTHER INFORMATION: Light Chain VL

<400> SEQUENCE: 12

```
Ser Tyr Val Leu Thr Gln Pro Pro Ser Val Ser Val Ala Pro Gly Gln
1               5                   10                  15
```

```
Thr Ala Arg Ile Thr Cys Gly Gly Asn Asn Leu Gly Ser Lys Ser Val
            20                  25                  30

His Trp Tyr Gln Gln Lys Pro Gly Gln Ala Pro Val Leu Val Val Tyr
                35                  40                  45

Asp Asp Ser Asp Arg Pro Ser Trp Ile Pro Glu Arg Phe Ser Gly Ser
 50                  55                  60

Asn Ser Gly Asn Thr Ala Thr Leu Thr Ile Ser Arg Gly Glu Ala Gly
 65                  70                  75                  80

Asp Glu Ala Asp Tyr Tyr Cys Gln Val Trp Asp Ser Ser Ser Asp His
                 85                  90                  95

Val Val Phe Gly Gly Thr Lys Leu Thr Val Leu
            100                 105
```

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

```
Asp Tyr Trp Met His
 1               5
```

<210> SEQ ID NO 14
<211> LENGTH: 19
<212> TYPE: PRT
<213> ORGANISM: Artificial Sequence
<220> FEATURE:
<223> OTHER INFORMATION: Synthetic peptide

<400> SEQUENCE: 14

```
His Ile Lys Ser Lys Thr Asp Ala Gly Thr Thr Asp Tyr Ala Ala Pro
 1               5                  10                  15

Val Lys Gly
```

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

```
Glu Ile Tyr Tyr Tyr Ala Phe Asp Ser
 1               5
```

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

```
Ser Gly Asp Asn Ile Gly Ser Lys Tyr Val His
 1               5                  10
```

<210> SEQ ID NO 17
<211> LENGTH: 7
<212> TYPE: PRT
<213> ORGANISM: Artificial Sequence
<220> FEATURE:

<223> OTHER INFORMATION: Synthetic peptide

<400> SEQUENCE: 17

Gly Asp Asn Glu Arg Pro Ser
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

Gln Ala Ala Asp Trp Val Asp Phe Tyr Val
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Gly Phe Thr Phe Ser Asp Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

<400> SEQUENCE: 20

Lys Ser Lys Thr Asp Ala Gly Thr
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Asp Asn Ile Gly Ser Lys Tyr
1               5

<210> SEQ ID NO 22
<211> LENGTH: 3
<212> TYPE: PRT
<213> ORGANISM: Artificial Sequence
<220> FEATURE:
<223> OTHER INFORMATION: Synthetic peptide

<400> SEQUENCE: 22

Gly Asp Asn
1

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 23

Ala Asp Trp Val Asp Phe Tyr
1               5

<210> SEQ ID NO 24
<211> LENGTH: 120
<212> TYPE: PRT
<213> ORGANISM: Artificial Sequence
<220> FEATURE:
<223> OTHER INFORMATION: Synthetic peptide

<400> SEQUENCE: 24

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Gly His Ile Lys Ser Lys Thr Asp Ala Gly Thr Thr Asp Tyr Ala Ala
    50                  55                  60

Pro Val Lys Gly Arg Phe Thr Ile Ser Arg Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Ile Tyr Tyr Ala Phe Asp Ser Trp Gly Gln
            100                 105                 110

Gly Thr Leu Val Thr Val Ser Ser
        115                 120

<210> SEQ ID NO 25
<211> LENGTH: 107
<212> TYPE: PRT
<213> ORGANISM: Artificial Sequence
<220> FEATURE:
<223> OTHER INFORMATION: Synthetic peptide

<400> SEQUENCE: 25

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser Lys Tyr Val
            20                  25                  30

His Trp Tyr Gln Gln Lys Pro Gly Gln Ala Pro Val Leu Val Ile Tyr
        35                  40                  45

Gly Asp Asn Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ala Ala Asp Trp Val Asp Phe Tyr
                85                  90                  95

Val Phe Gly Gly Gly Thr Lys Leu Thr Val Leu
            100                 105

<210> SEQ ID NO 26
<211> LENGTH: 223
<212> TYPE: PRT
<213> ORGANISM: Artificial Sequence
<220> FEATURE:
<223> OTHER INFORMATION: Synthetic peptide
```

<400> SEQUENCE: 26

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Trp Met His Trp Val Arg Gln Ala Pro Gly Lys Gly Leu Glu Trp Val
        35                  40                  45

Gly His Ile Lys Ser Lys Thr Asp Ala Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Ile Tyr Tyr Ala Phe Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys
    210                 215                 220

<210> SEQ ID NO 27
<211> LENGTH: 213
<212> TYPE: PRT
<213> ORGANISM: Artificial Sequence
<220> FEATURE:
<223> OTHER INFORMATION: Synthetic peptide

<400> SEQUENCE: 27

Ser Tyr Glu Leu Thr Gln Pro Leu Ser Val Ser Val Ala Leu Gly Gln
1               5                   10                  15

Thr Ala Arg Ile Thr Cys Ser Gly Asp Asn Ile Gly Ser Lys Tyr Val
            20                  25                  30

His Trp Tyr Gln Gln Lys Pro Gly Gln Ala Pro Val Leu Val Ile Tyr
        35                  40                  45

Gly Asp Asn Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Ala Ala Asp Trp Val Asp Phe Tyr
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala

```
                130             135             140
Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
                180                 185                 190

Ser Cys Gln Val Thr His Glu Gly Ser Thr Val Glu Lys Thr Val Ala
            195                 200                 205

Pro Thr Glu Cys Ser
        210

<210> SEQ ID NO 28
<211> LENGTH: 450
<212> TYPE: PRT
<213> ORGANISM: Artificial Sequence
<220> FEATURE:
<223> OTHER INFORMATION: Synthetic peptide

<400> SEQUENCE: 28

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Trp Met His Trp Val Arg Gln Ala Pro Gly Lys Gly Leu Glu Trp Val
            35                  40                  45

Gly His Ile Lys Ser Lys Thr Asp Ala Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Glu Ile Tyr Tyr Ala Phe Asp Ser Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

```
                275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 29
<211> LENGTH: 213
<212> TYPE: PRT
<213> ORGANISM: Artificial Sequence
<220> FEATURE:
<223> OTHER INFORMATION: Synthetic peptide

<400> SEQUENCE: 29

Ser Tyr Glu Leu Thr Gln Pro Leu Ser Val Ser Val Ala Leu Gly Gln
1               5                   10                  15
Thr Ala Arg Ile Thr Cys Ser Gly Asp Asn Ile Gly Ser Lys Tyr Val
            20                  25                  30
His Trp Tyr Gln Gln Lys Pro Gly Gln Ala Pro Val Leu Val Ile Tyr
        35                  40                  45
Gly Asp Asn Glu Arg Pro Ser Gly Ile Pro Glu Arg Phe Ser Gly Ser
    50                  55                  60
Asn Ser Gly Asn Thr Ala Thr Leu Thr Ile Ser Arg Ala Gln Ala Gly
65                  70                  75                  80
Asp Glu Ala Asp Tyr Tyr Cys Gln Ala Ala Asp Trp Val Asp Phe Tyr
                85                  90                  95
Val Phe Gly Gly Gly Thr Lys Leu Thr Val Leu Gly Gln Pro Lys Ala
            100                 105                 110
Ala Pro Ser Val Thr Leu Phe Pro Pro Ser Ser Glu Glu Leu Gln Ala
        115                 120                 125
Asn Lys Ala Thr Leu Val Cys Leu Ile Ser Asp Phe Tyr Pro Gly Ala
    130                 135                 140
Val Thr Val Ala Trp Lys Ala Asp Ser Ser Pro Val Lys Ala Gly Val
145                 150                 155                 160
Glu Thr Thr Thr Pro Ser Lys Gln Ser Asn Asn Lys Tyr Ala Ala Ser
                165                 170                 175
Ser Tyr Leu Ser Leu Thr Pro Glu Gln Trp Lys Ser His Arg Ser Tyr
```

```
                    180                 185                 190
Ser Cys Gln Val Thr His Glu Gly Ser Thr Val Glu Lys Thr Val Ala
            195                 200                 205

Pro Thr Glu Cys Ser
        210

<210> SEQ ID NO 30
<211> LENGTH: 149
<212> TYPE: PRT
<213> ORGANISM: Artificial Sequence
<220> FEATURE:
<223> OTHER INFORMATION: Synthetic peptide

<400> SEQUENCE: 30

Met Gly Ser Ser His His His His His His Leu Glu Val Leu Phe Gln
1               5                   10                  15

Gly Pro Tyr Asp Phe Thr Asn Cys Asp Phe Glu Lys Ile Lys Ala Ala
            20                  25                  30

Tyr Leu Ser Thr Ile Ser Lys Asp Leu Ile Thr Tyr Met Ser Gly Thr
        35                  40                  45

Lys Ser Thr Glu Phe Asn Asn Thr Val Ser Cys Ser Asn Arg Pro His
50                  55                  60

Cys Leu Thr Glu Ile Gln Ser Leu Thr Phe Asn Pro Thr Ala Gly Cys
65                  70                  75                  80

Ala Ser Leu Ala Lys Glu Met Phe Ala Met Lys Thr Lys Ala Ala Leu
            85                  90                  95

Ala Ile Trp Cys Pro Gly Tyr Ser Glu Thr Gln Ile Asn Ala Thr Gln
        100                 105                 110

Ala Met Lys Lys Arg Arg Lys Arg Lys Val Thr Thr Asn Lys Cys Leu
    115                 120                 125

Glu Gln Val Ser Gln Leu Gln Gly Leu Trp Arg Arg Phe Asn Arg Pro
130                 135                 140

Leu Leu Lys Gln Gln
145

<210> SEQ ID NO 31
<211> LENGTH: 107
<212> TYPE: PRT
<213> ORGANISM: Artificial
<220> FEATURE:
<223> OTHER INFORMATION: Dom30h-440-81/86 amino acid sequence

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Arg Asn Trp
            20                  25                  30

Leu Asp Trp Tyr Gln Gln Lys Pro Gly Lys Ala Pro Lys Leu Leu Ile
        35                  40                  45

Trp Gly Ala Ser His Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Gln Ile Gly Glu Asp Pro Val
            85                  90                  95

Thr Phe Gly Gln Gly Thr Lys Val Glu Ile Lys
        100                 105
```

<210> SEQ ID NO 32
<211> LENGTH: 11
<212> TYPE: PRT
<213> ORGANISM: Artificial
<220> FEATURE:
<223> OTHER INFORMATION: CDRL1 of Dom30h-440-81/86, Dom30h-440-53,
      Dom30h-440-54, Dom30h-440-55, Dom30h-440-56, Dom30h-440-57,
      Dom30h-440-58, Dom30h-440-60, Dom30h-440-63, Dom30h-440-64 and
      Dom30h-440-65 (Kabat, Chothia and AbM CDR definition)

<400> SEQUENCE: 32

Arg Ala Ser Arg Pro Ile Arg Asn Trp Leu Asp
1               5                   10

<210> SEQ ID NO 33
<211> LENGTH: 7
<212> TYPE: PRT
<213> ORGANISM: Artificial
<220> FEATURE:
<223> OTHER INFORMATION: CDRL2 of Dom30h-440-81/86, Dom30h-440-53,
      Dom30h-440-54, Dom30h-440-55, Dom30h-440-56, Dom30h-440-57,
      Dom30h-440-58, Dom30h-440-60, Dom30h-440-63, Dom30h-440-64 and
      Dom30h-440-65 (Kabat, Chothia, AbM CDR definition)

<400> SEQUENCE: 33

Gly Ala Ser His Leu Gln Ser
1               5

<210> SEQ ID NO 34
<211> LENGTH: 9
<212> TYPE: PRT
<213> ORGANISM: Artificial
<220> FEATURE:
<223> OTHER INFORMATION: CDRL3 of Dom30h-440-81/86 and Dom30h-440-55
      (Kabat, Chothia, AbM CDR definition)

<400> SEQUENCE: 34

Val Gln Ile Gly Glu Asp Pro Val Thr
1               5

<210> SEQ ID NO 35
<211> LENGTH: 10
<212> TYPE: PRT
<213> ORGANISM: Artificial
<220> FEATURE:
<223> OTHER INFORMATION: CDRL2 of Dom30h-440-81/86 (Contact CDR
      definition)

<400> SEQUENCE: 35

Leu Leu Ile Trp Gly Ala Ser His Leu Gln
1               5                   10

<210> SEQ ID NO 36
<211> LENGTH: 5
<212> TYPE: PRT
<213> ORGANISM: Mus musculus

<400> SEQUENCE: 36

Arg Tyr Asn Val His
1               5

<210> SEQ ID NO 37
<211> LENGTH: 16
<212> TYPE: PRT
<213> ORGANISM: Mus musculus

<400> SEQUENCE: 37

Met Ile Trp Asp Gly Gly Ser Thr Asp Tyr Asn Ser Ala Leu Lys Ser
1               5                   10                  15

<210> SEQ ID NO 38
<211> LENGTH: 6
<212> TYPE: PRT
<213> ORGANISM: Mus musculus

<400> SEQUENCE: 38

Asn Arg Tyr Glu Ser Gly
1               5

<210> SEQ ID NO 39
<211> LENGTH: 17
<212> TYPE: PRT
<213> ORGANISM: Mus musculus

<400> SEQUENCE: 39

Lys Ser Ser Gln Ser Leu Leu Asn Ser Gly Asn Arg Lys Asn Tyr Leu
1               5                   10                  15

Thr

<210> SEQ ID NO 40
<211> LENGTH: 7
<212> TYPE: PRT
<213> ORGANISM: Mus musculus

<400> SEQUENCE: 40

Trp Ala Ser Thr Arg Glu Ser
1               5

<210> SEQ ID NO 41
<211> LENGTH: 12
<212> TYPE: PRT
<213> ORGANISM: Mus musculus

<400> SEQUENCE: 41

Gln Asn Asp Tyr Thr Tyr Pro Phe Thr Phe Gly Ser
1               5                   10

<210> SEQ ID NO 42
<211> LENGTH: 5
<212> TYPE: PRT
<213> ORGANISM: Mus musculus

<400> SEQUENCE: 42

Ala Tyr Trp Met Ser
1               5

<210> SEQ ID NO 43
<211> LENGTH: 17
<212> TYPE: PRT
<213> ORGANISM: Mus musculus

<400> SEQUENCE: 43

Glu Ile Asn Pro Asp Ser Ser Thr Ile Asn Cys Thr Pro Ser Leu Lys
1               5                   10                  15

Asp

<210> SEQ ID NO 44
<211> LENGTH: 11
<212> TYPE: PRT
<213> ORGANISM: Mus musculus

```
<400> SEQUENCE: 44

Arg Leu Arg Pro Phe Trp Tyr Phe Asp Val Trp
1               5                   10

<210> SEQ ID NO 45
<211> LENGTH: 16
<212> TYPE: PRT
<213> ORGANISM: Mus musculus

<400> SEQUENCE: 45

Arg Ser Ser Gln Ser Ile Val Gln Ser Asn Gly Asn Thr Tyr Leu Glu
1               5                   10                  15

<210> SEQ ID NO 46
<211> LENGTH: 7
<212> TYPE: PRT
<213> ORGANISM: Mus musculus

<400> SEQUENCE: 46

Lys Val Ser Asn Arg Phe Ser
1               5

<210> SEQ ID NO 47
<211> LENGTH: 9
<212> TYPE: PRT
<213> ORGANISM: Mus musculus

<400> SEQUENCE: 47

Phe Gln Gly Ser His Val Pro Arg Thr
1               5

<210> SEQ ID NO 48
<211> LENGTH: 6
<212> TYPE: PRT
<213> ORGANISM: Mus musculus

<400> SEQUENCE: 48

Thr Asp Tyr Ala Trp Asn
1               5

<210> SEQ ID NO 49
<211> LENGTH: 16
<212> TYPE: PRT
<213> ORGANISM: Mus musculus

<400> SEQUENCE: 49

Tyr Ile Phe Tyr Ser Gly Ser Thr Thr Tyr Thr Pro Ser Leu Lys Ser
1               5                   10                  15

<210> SEQ ID NO 50
<211> LENGTH: 8
<212> TYPE: PRT
<213> ORGANISM: Mus musculus

<400> SEQUENCE: 50

Gly Gly Tyr Asp Val Asn Tyr Phe
1               5

<210> SEQ ID NO 51
<211> LENGTH: 11
<212> TYPE: PRT
<213> ORGANISM: Mus musculus

<400> SEQUENCE: 51
```

```
Leu Ala Ser Gln Thr Ile Gly Ala Trp Leu Ala
1               5                   10
```

<210> SEQ ID NO 52
<211> LENGTH: 7
<212> TYPE: PRT
<213> ORGANISM: Mus musculus

<400> SEQUENCE: 52

```
Ala Ala Thr Arg Leu Ala Asp
1               5
```

<210> SEQ ID NO 53
<211> LENGTH: 9
<212> TYPE: PRT
<213> ORGANISM: Mus musculus

<400> SEQUENCE: 53

```
Gln Gln Phe Phe Ser Thr Pro Trp Thr
1               5
```

<210> SEQ ID NO 54
<211> LENGTH: 5
<212> TYPE: PRT
<213> ORGANISM: Mus musculus

<400> SEQUENCE: 54

```
Gly Tyr Thr Met Asn
1               5
```

<210> SEQ ID NO 55
<211> LENGTH: 16
<212> TYPE: PRT
<213> ORGANISM: Mus musculus

<400> SEQUENCE: 55

```
Leu Ile Asn Pro Tyr Asn Gly Val Thr Ser Tyr Asn Gln Lys Phe Lys
1               5                   10                  15
```

<210> SEQ ID NO 56
<211> LENGTH: 8
<212> TYPE: PRT
<213> ORGANISM: Mus musculus

<400> SEQUENCE: 56

```
Gly Asp Gly Asn Tyr Trp Tyr Phe
1               5
```

<210> SEQ ID NO 57
<211> LENGTH: 11
<212> TYPE: PRT
<213> ORGANISM: Mus musculus

<400> SEQUENCE: 57

```
Ser Ala Ser Ser Ser Val Thr Tyr Met His Trp
1               5                   10
```

<210> SEQ ID NO 58
<211> LENGTH: 7
<212> TYPE: PRT
<213> ORGANISM: Mus musculus

<400> SEQUENCE: 58

```
Glu Ile Ser Lys Leu Ala Ser
1               5
```

```
<210> SEQ ID NO 59
<211> LENGTH: 9
<212> TYPE: PRT
<213> ORGANISM: Mus musculus

<400> SEQUENCE: 59

Gln Glu Trp Asn Tyr Pro Tyr Thr Phe
1               5

<210> SEQ ID NO 60
<211> LENGTH: 117
<212> TYPE: PRT
<213> ORGANISM: Mus musculus

<400> SEQUENCE: 60

Gln Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Asn Val His Trp Val Arg Gln Pro Pro Gly Lys Gly Leu Glu Trp Leu
        35                  40                  45

Gly Met Ile Trp Asp Gly Gly Ser Thr Asp Tyr Asn Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asn Arg Tyr Glu Ser Gly Met Asp Tyr Trp Gly Gln Gly Thr Thr
            100                 105                 110

Val Thr Val Ser Ser
        115

<210> SEQ ID NO 61
<211> LENGTH: 114
<212> TYPE: PRT
<213> ORGANISM: Mus musculus

<400> SEQUENCE: 61

Asp Ile Val Met Thr Gln Thr Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Arg Lys Asn Tyr Leu Thr Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ile
65                  70                  75                  80

Ile Ser Ser Val Gln Ala Glu Asp Leu Ala Val Tyr Tyr Cys Gln Asn
                85                  90                  95

Asp Tyr Thr Tyr Pro Phe Thr Phe Gly Ser Gly Thr Lys Leu Glu Ile
            100                 105                 110

Lys Arg

<210> SEQ ID NO 62
<211> LENGTH: 119
<212> TYPE: PRT
```

<213> ORGANISM: Mus musculus

<400> SEQUENCE: 62

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Ala Phe Ser Ala Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Cys Thr Pro Ser Leu
    50                  55                  60

Lys Asp Lys Phe Ile Ile Ser Arg Asp Asn Ala Lys Asn Thr Leu Ser
65                  70                  75                  80

Leu Gln Met Asn Lys Val Arg Ser Glu Asp Thr Ala Leu Tyr Tyr Cys
                85                  90                  95

Ala Arg Arg Leu Arg Pro Phe Trp Tyr Phe Asp Val Trp Gly Ala Gly
            100                 105                 110

Thr Thr Val Thr Val Ser Ser
            115

<210> SEQ ID NO 63
<211> LENGTH: 112
<212> TYPE: PRT
<213> ORGANISM: Mus musculus

<400> SEQUENCE: 63

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Gln Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Arg Thr Phe Gly Gly Gly Thr Lys Leu Glu Ile Lys
            100                 105                 110

<210> SEQ ID NO 64
<211> LENGTH: 119
<212> TYPE: PRT
<213> ORGANISM: Mus musculus

<400> SEQUENCE: 64

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Thr Asp
            20                  25                  30

Tyr Ala Trp Asn Trp Ile Arg Gln Phe Pro Gly Asn Lys Leu Glu Trp
        35                  40                  45

Met Gly Tyr Ile Phe Tyr Ser Gly Ser Thr Tyr Thr Pro Ser Leu
    50                  55                  60

Lys Ser Arg Ile Ser Ile Thr Arg Asp Thr Ser Lys Asn Gln Phe Phe
65                  70                  75                  80

```
Leu Gln Leu Asn Ser Val Thr Glu Asp Thr Ala Thr Tyr Tyr Cys
                85                  90                  95

Ala Arg Gly Gly Tyr Asp Val Asn Tyr Phe Asp Tyr Trp Gly Gln Gly
            100                 105                 110

Thr Thr Leu Thr Val Ser Ser
        115

<210> SEQ ID NO 65
<211> LENGTH: 107
<212> TYPE: PRT
<213> ORGANISM: Mus musculus

<400> SEQUENCE: 65

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Ala Trp
            20                  25                  30

Leu Ala Trp Tyr Gln Gln Lys Pro Gly Lys Ser Pro Gln Leu Leu Ile
        35                  40                  45

Tyr Ala Ala Thr Arg Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Phe Phe Ser Thr Pro Trp
                85                  90                  95

Thr Phe Gly Gly Gly Thr Lys Leu Glu Ile Lys
            100                 105

<210> SEQ ID NO 66
<211> LENGTH: 119
<212> TYPE: PRT
<213> ORGANISM: Mus musculus

<400> SEQUENCE: 66

Glu Val Gln Leu Gln Gln Ser Gly Pro Glu Leu Leu Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Val Thr Ser Tyr Asn Gln Lys Phe
    50                  55                  60

Lys Gly Lys Ala Thr Leu Thr Val Ala Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Gly Asp Gly Asn Tyr Trp Tyr Phe Asp Val Trp Gly Ala Gly
            100                 105                 110

Thr Thr Val Thr Val Ser Ser
        115

<210> SEQ ID NO 67
<211> LENGTH: 105
<212> TYPE: PRT
<213> ORGANISM: Mus musculus

<400> SEQUENCE: 67
```

Glu Ile Val Leu Thr Gln Ser Pro Ala Ile Thr Ala Ala Ser Leu Gly
1               5                   10                  15

Gln Lys Val Thr Ile Thr Cys Ser Ala Ser Ser Val Thr Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Val Arg Phe Ser Gly Ser
    50                  55                  60

Gly Ser Gly Thr Ser Tyr Ser Leu Thr Ile Ser Met Glu Ala Glu
65                  70                  75                  80

Asp Ala Ala Ile Tyr Tyr Cys Gln Glu Trp Asn Tyr Pro Tyr Thr Phe
                85                  90                  95

Gly Gly Gly Thr Lys Leu Glu Ile Lys
            100                 105

<210> SEQ ID NO 68
<211> LENGTH: 119
<212> TYPE: PRT
<213> ORGANISM: Mus musculus

<400> SEQUENCE: 68

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Ser Gly Ile Thr Ser Tyr Asn Gln Asn Phe
    50                  55                  60

Lys Gly Lys Ala Thr Leu Thr Val Asp Lys Ser Ser Thr Ala Tyr
65                  70                  75                  80

Met Glu Leu Leu Asn Leu Thr Ser Glu Asp Ser Ala Val Tyr Tyr Cys
                85                  90                  95

Ala Arg Gly Asp Gly Asn Tyr Trp Tyr Phe Asp Val Trp Gly Ala Gly
            100                 105                 110

Thr Thr Val Thr Val Ser Ser
            115

<210> SEQ ID NO 69
<211> LENGTH: 105
<212> TYPE: PRT
<213> ORGANISM: Mus musculus

<400> SEQUENCE: 69

Glu Ile Ile Leu Thr Gln Ser Pro Ala Ile Thr Ala Ala Ser Leu Gly
1               5                   10                  15

Gln Lys Val Thr Ile Thr Cys Ser Ala Ser Ser Val Ser Tyr Met
            20                  25                  30

His Trp Tyr Gln Gln Lys Ser Gly Thr Ser Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ile Tyr Tyr Cys Gln Tyr Trp Asn Tyr Pro Tyr Thr Phe
                85                  90                  95

Gly Gly Gly Thr Lys Leu Glu Ile Lys
            100                 105

<210> SEQ ID NO 70
<211> LENGTH: 5
<212> TYPE: PRT
<213> ORGANISM: Mus musculus

<400> SEQUENCE: 70

Gly Tyr Thr Met Asn
1               5

<210> SEQ ID NO 71
<211> LENGTH: 16
<212> TYPE: PRT
<213> ORGANISM: Mus musculus

<400> SEQUENCE: 71

Leu Ile Asn Pro Tyr Ser Gly Ile Thr Ser Tyr Asn Gln Asn Phe Lys
1               5                   10                  15

<210> SEQ ID NO 72
<211> LENGTH: 8
<212> TYPE: PRT
<213> ORGANISM: Mus musculus

<400> SEQUENCE: 72

Gly Asp Gly Asn Tyr Trp Tyr Phe
1               5

<210> SEQ ID NO 73
<211> LENGTH: 11
<212> TYPE: PRT
<213> ORGANISM: Mus musculus

<400> SEQUENCE: 73

Ser Ala Ser Ser Ser Val Ser Tyr Met His Trp
1               5                   10

<210> SEQ ID NO 74
<211> LENGTH: 7
<212> TYPE: PRT
<213> ORGANISM: Mus musculus

<400> SEQUENCE: 74

Glu Ile Ser Lys Leu Ala Ser
1               5

<210> SEQ ID NO 75
<211> LENGTH: 9
<212> TYPE: PRT
<213> ORGANISM: Mus musculus

<400> SEQUENCE: 75

Gln Tyr Trp Asn Tyr Pro Tyr Thr Phe
1               5

<210> SEQ ID NO 76
<211> LENGTH: 12
<212> TYPE: PRT
<213> ORGANISM: Cricetulus migratorius

<400> SEQUENCE: 76

Gly Phe Ser Ile Thr Thr Ser Gly Tyr Tyr Trp Thr
1               5                   10

<210> SEQ ID NO 77
<211> LENGTH: 16
<212> TYPE: PRT
<213> ORGANISM: Cricetulus migratorius

<400> SEQUENCE: 77

Tyr Ile Gly Tyr Asn Ser Lys Thr Tyr Tyr Asn Pro Ser Leu Lys Ser
1               5                   10                  15

<210> SEQ ID NO 78
<211> LENGTH: 12
<212> TYPE: PRT
<213> ORGANISM: Cricetulus migratorius

<400> SEQUENCE: 78

Ser Leu Tyr Gly Gly Tyr Lys Asp Ala Phe Asp Ser
1               5                   10

<210> SEQ ID NO 79
<211> LENGTH: 11
<212> TYPE: PRT
<213> ORGANISM: Cricetulus migratorius

<400> SEQUENCE: 79

Lys Ala Ser Gln Ser Ile Gly Thr Ser Leu His
1               5                   10

<210> SEQ ID NO 80
<211> LENGTH: 7
<212> TYPE: PRT
<213> ORGANISM: Cricetulus migratorius

<400> SEQUENCE: 80

Phe Ala Ser Arg Ser Ile Thr
1               5

<210> SEQ ID NO 81
<211> LENGTH: 9
<212> TYPE: PRT
<213> ORGANISM: Cricetulus migratorius

<400> SEQUENCE: 81

Gln Gln Ser Pro Gly Phe Pro Pro Thr
1               5

<210> SEQ ID NO 82
<211> LENGTH: 122
<212> TYPE: PRT
<213> ORGANISM: Cricetulus migratorius

<400> SEQUENCE: 82

Gln Ile Gln Leu Gln Glu Ser Gly Pro Gly Leu Val Lys Pro Ser Gln
1               5                   10                  15

Ser Leu Ser Leu Thr Cys Ser Val Thr Gly Phe Ser Ile Thr Thr Ser
                20                  25                  30

Gly Tyr Tyr Trp Thr Trp Ile Arg Gln Phe Pro Gly Lys Lys Leu Glu
            35                  40                  45

Trp Met Gly Tyr Ile Gly Tyr Asn Ser Lys Thr Tyr Tyr Asn Pro Ser
        50                  55                  60

Leu Lys Ser Arg Ile Ser Ile Thr Arg Asp Thr Ser Lys Asn Gln Phe
65                  70                  75                  80

```
Leu Leu His Leu Asn Ser Val Thr Thr Glu Asp Thr Ala Thr Tyr Tyr
                85                  90                  95

Cys Ala Arg Ser Leu Tyr Gly Gly Tyr Lys Asp Ala Phe Asp Ser Trp
            100                 105                 110

Gly Gln Gly Thr Leu Val Thr Val Ser Ser
        115                 120

<210> SEQ ID NO 83
<211> LENGTH: 108
<212> TYPE: PRT
<213> ORGANISM: Cricetulus migratorius

<400> SEQUENCE: 83

Asp Val Val Leu Thr Gln Thr Pro Ala Thr Leu Ser Ala Ile Pro Gly
1               5                   10                  15

Glu Arg Val Thr Met Thr Cys Lys Ala Ser Gln Ser Ile Gly Thr Ser
            20                  25                  30

Leu His Trp Tyr Gln His Arg Pro Asn Glu Thr Pro Arg Leu Leu Ile
        35                  40                  45

Lys Phe Ala Ser Arg Ser Ile Thr Gly Ile Pro Ser Arg Phe Ser Gly
    50                  55                  60

Ser Gly Ser Gly Thr Asp Phe Thr Leu Gly Ile Asn Asn Leu Glu Ala
65                  70                  75                  80

Glu Asp Phe Ala Ile Tyr Tyr Cys Gln Gln Ser Pro Gly Phe Pro Pro
                85                  90                  95

Thr Phe Gly Ser Gly Thr Lys Leu Glu Ile Asn Arg
            100                 105

<210> SEQ ID NO 84
<211> LENGTH: 12
<212> TYPE: PRT
<213> ORGANISM: Artificial
<220> FEATURE:
<223> OTHER INFORMATION: hCDR1 TSLPR-012_166

<400> SEQUENCE: 84

Gly Phe Ser Ile Thr Thr Ser Gly Tyr Tyr Trp Ser
1               5                   10

<210> SEQ ID NO 85
<211> LENGTH: 16
<212> TYPE: PRT
<213> ORGANISM: Artificial
<220> FEATURE:
<223> OTHER INFORMATION: hCDR2 TSLPR-012_141

<400> SEQUENCE: 85

Tyr Ile Gly Tyr Asn Ser Lys Thr Tyr Tyr Asn Pro Ala Leu Lys Ser
1               5                   10                  15

<210> SEQ ID NO 86
<211> LENGTH: 11
<212> TYPE: PRT
<213> ORGANISM: Artificial
<220> FEATURE:
<223> OTHER INFORMATION: lCDR1 TSLPR-012_141

<400> SEQUENCE: 86

Arg Ala Ser Gln Ser Ile Gly Thr Ser Leu His
1               5                   10

<210> SEQ ID NO 87
```

<211> LENGTH: 7
<212> TYPE: PRT
<213> ORGANISM: Artificial
<220> FEATURE:
<223> OTHER INFORMATION: lCDR2 TSLPR-012_141

<400> SEQUENCE: 87

Phe Ala Ser Arg Leu Gln Ser
1               5

<210> SEQ ID NO 88
<211> LENGTH: 7
<212> TYPE: PRT
<213> ORGANISM: Artificial
<220> FEATURE:
<223> OTHER INFORMATION: lCDR2 TSLPR-012_75

<400> SEQUENCE: 88

Phe Ala Ser Arg Ser Ile Ser
1               5

<210> SEQ ID NO 89
<211> LENGTH: 122
<212> TYPE: PRT
<213> ORGANISM: Artificial
<220> FEATURE:
<223> OTHER INFORMATION: sequence TSLPR-012_141 (humanized) HC variable
      region

<400> SEQUENCE: 89

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Ile Thr Thr Ser
            20                  25                  30

Gly Tyr Tyr Trp Thr Trp Ile Arg Gln Phe Pro Gly Lys Gly Leu Glu
        35                  40                  45

Trp Met Gly Tyr Ile Gly Tyr Asn Ser Lys Thr Tyr Tyr Asn Pro Ala
    50                  55                  60

Leu Lys Ser Arg Ile Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Ser Leu Tyr Gly Tyr Lys Ala Phe Asp Ser Trp
            100                 105                 110

Gly Gln Gly Thr Leu Val Thr Val Ser Ser
        115                 120

<210> SEQ ID NO 90
<211> LENGTH: 108
<212> TYPE: PRT
<213> ORGANISM: Artificial
<220> FEATURE:
<223> OTHER INFORMATION: sequence TSLPR-012_141 (humanized) LC variable
      region

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Ser
            20                  25                  30

Leu His Trp Tyr Gln Gln Lys Pro Gly Lys Ala Pro Lys Leu Leu Ile
        35                  40                  45

```
Lys Phe Ala Ser Arg Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Pro Gly Phe Pro Pro
                    85                  90                  95

Thr Phe Gly Gln Gly Thr Lys Leu Glu Ile Lys Arg
                100                 105
```

<210> SEQ ID NO 91
<211> LENGTH: 108
<212> TYPE: PRT
<213> ORGANISM: Artificial
<220> FEATURE:
<223> OTHER INFORMATION: sequence TSLPR-012_75 (humanized) LC variable
      region

<400> SEQUENCE: 91

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Gly Thr Ser
                20                  25                  30

Leu His Trp Tyr Gln Gln Lys Pro Asp Gln Ser Pro Lys Leu Leu Ile
            35                  40                  45

Lys Phe Ala Ser Arg Ser Ile Ser Gly Val Pro Ser Arg Phe Ser Gly
        50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Ser Pro Gly Phe Pro Pro
                    85                  90                  95

Thr Phe Gly Gln Gly Thr Lys Leu Glu Ile Lys Arg
                100                 105
```

<210> SEQ ID NO 92
<211> LENGTH: 122
<212> TYPE: PRT
<213> ORGANISM: Artificial
<220> FEATURE:
<223> OTHER INFORMATION: sequence TSLPR-012_166 (humanized) HC variable
      region

<400> SEQUENCE: 92

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Phe Ser Ile Thr Thr Ser
                20                  25                  30

Gly Tyr Tyr Trp Ser Trp Ile Arg Gln His Pro Gly Lys Gly Leu Glu
            35                  40                  45

Trp Ile Gly Tyr Ile Gly Tyr Asn Ser Lys Tyr Tyr Ser Pro Ser
        50                  55                  60

Leu Lys Ser Arg Val Thr Ile Ser Arg Asp Thr Ser Lys Asn Gln Phe
 65                  70                  75                  80

Ser Leu Lys Leu Ser Ser Val Thr Ala Ala Asp Thr Ala Val Tyr Tyr
                    85                  90                  95

Cys Ala Arg Ser Leu Tyr Gly Gly Tyr Lys Asp Ala Phe Asp Ser Trp
                100                 105                 110

Gly Gln Gly Thr Leu Val Thr Val Ser Ser
                115                 120
```

<210> SEQ ID NO 93
<211> LENGTH: 108
<212> TYPE: PRT
<213> ORGANISM: Artificial
<220> FEATURE:
<223> OTHER INFORMATION: sequence TSLPR-012_166 (humanized) LC variable region

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Thr Ser
            20                  25                  30

Leu His Trp Tyr Gln His Arg Pro Gly Glu Thr Pro Lys Leu Leu Ile
        35                  40                  45

Lys Phe Ala Ser Arg Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Pro Gly Phe Pro Pro
                85                  90                  95

Thr Phe Gly Gln Gly Thr Lys Leu Glu Ile Lys Arg
            100                 105

<210> SEQ ID NO 94
<211> LENGTH: 108
<212> TYPE: PRT
<213> ORGANISM: Artificial
<220> FEATURE:
<223> OTHER INFORMATION: sequence TSLPR-012_189 (humanized) LC variable region

<400> SEQUENCE: 94

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Ser
            20                  25                  30

Leu His Trp Tyr Gln Gln Lys Pro Gly Gln Ala Pro Arg Leu Leu Ile
        35                  40                  45

Lys Phe Ala Ser Arg Ser Ile Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Pro Gly Phe Pro Pro
                85                  90                  95

Thr Phe Gly Gln Gly Thr Lys Leu Glu Ile Lys Arg
            100                 105

<210> SEQ ID NO 95
<211> LENGTH: 10
<212> TYPE: PRT
<213> ORGANISM: Artificial Sequence
<220> FEATURE:
<223> OTHER INFORMATION: Synthetic peptide

<400> SEQUENCE: 95

Gly Tyr Ile Phe Thr Asp Tyr Ala Met His
1               5                   10

<210> SEQ ID NO 96

```
<211> LENGTH: 17
<212> TYPE: PRT
<213> ORGANISM: Artificial Sequence
<220> FEATURE:
<223> OTHER INFORMATION: Synthetic peptide

<400> SEQUENCE: 96

Thr Phe Ile Pro Leu Leu Asp Thr Ser Asp Tyr Ala Gln Lys Phe Gln
1               5                   10                  15
Gly

<210> SEQ ID NO 97
<211> LENGTH: 11
<212> TYPE: PRT
<213> ORGANISM: Artificial Sequence
<220> FEATURE:
<223> OTHER INFORMATION: Synthetic peptide

<400> SEQUENCE: 97

Met Gly Val Thr His Ser Tyr Val Met Asp Ala
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic peptide

<400> SEQUENCE: 98

Arg Ala Ser Gln Pro Ile Ser Ile Ser Val His
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Synthetic peptide

<400> SEQUENCE: 99

Phe Ala Ser Gln Ser Ile Ser
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic peptide

<400> SEQUENCE: 100

Gln Gln Thr Phe Ser Leu Pro Tyr Thr
1               5

<210> SEQ ID NO 101
<211> LENGTH: 120
<212> TYPE: PRT
<213> ORGANISM: Artificial Sequence
<220> FEATURE:
<223> OTHER INFORMATION: Synthetic peptide

<400> SEQUENCE: 101

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ile Phe Thr Asp Tyr
```

```
            20                  25                  30
Ala Met His Trp Val Arg Gln Ala Pro Gly Gln Gly Leu Glu Trp Met
            35                  40                  45

Gly Thr Phe Ile Pro Leu Leu Asp Thr Ser Asp Tyr Ala Gln Lys Phe
        50                  55                  60

Gln Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Met Gly Val Thr His Ser Tyr Val Met Asp Ala Trp Gly Gln
                100                 105                 110

Gly Thr Leu Val Thr Val Ser Ser
                115                 120

<210> SEQ ID NO 102
<211> LENGTH: 109
<212> TYPE: PRT
<213> ORGANISM: Artificial Sequence
<220> FEATURE:
<223> OTHER INFORMATION: Synthetic peptide

<400> SEQUENCE: 102

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Pro Ile Ser Ile Ser
            20                  25                  30

Val His Trp Tyr Gln Gln Lys Pro Gly Gln Ala Pro Arg Leu Leu Ile
            35                  40                  45

Tyr Phe Ala Ser Gln Ser Ile Ser Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Thr Phe Ser Leu Pro Tyr
                85                  90                  95

Thr Phe Gly Gln Gly Thr Lys Val Glu Ile Lys Arg Thr
                100                 105

<210> SEQ ID NO 103
<211> LENGTH: 450
<212> TYPE: PRT
<213> ORGANISM: Artificial Sequence
<220> FEATURE:
<223> OTHER INFORMATION: Synthetic peptide

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Ala Met His Trp Val Arg Gln Ala Pro Gly Gln Gly Leu Glu Trp Met
            35                  40                  45

Gly Thr Phe Ile Pro Leu Leu Asp Thr Ser Asp Tyr Ala Gln Lys Phe
        50                  55                  60

Gln Gly Arg Val Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

Ala Arg Met Gly Val Thr His Ser Tyr Val Met Asp Ala Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 104
<211> LENGTH: 214
<212> TYPE: PRT
<213> ORGANISM: Artificial Sequence
<220> FEATURE:
<223> OTHER INFORMATION: Synthetic peptide

<400> SEQUENCE: 104

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Pro Ile Ser Ile Ser
            20                  25                  30

Val His Trp Tyr Gln Gln Lys Pro Gly Gln Ala Pro Arg Leu Leu Ile
        35                  40                  45

Tyr Phe Ala Ser Gln Ser Ile Ser Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Thr Phe Ser Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 105
<211> LENGTH: 448
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Heavy chain

<400> SEQUENCE: 105

Gln Met Gln Leu Val Glu Ser Gly Gly Val Val Gln Pro Gly Arg
1               5                   10                  15

Ser Leu Arg Leu Ser Cys Ala Ala Ser Gly Phe Thr Phe Arg Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Thr Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Ala Arg Ala Pro Gln Trp Glu Leu Val His Glu Ala Phe Asp Ile Trp
            100                 105                 110

Gly Gln Gly Thr Met Val Thr Val Ser Ser Ala Ser Thr Lys Gly Pro
        115                 120                 125
```

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 106
<211> LENGTH: 214
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Light Chain

<400> SEQUENCE: 106

Ser Tyr Val Leu Thr Gln Pro Pro Ser Val Ser Val Ala Pro Gly Gln
1               5                   10                  15

Thr Ala Arg Ile Thr Cys Gly Gly Asn Asn Leu Gly Ser Lys Ser Val
            20                  25                  30

```
                His Trp Tyr Gln Gln Lys Pro Gly Gln Ala Pro Val Leu Val Val Tyr
                        35                  40                  45

Asp Asp Ser Asp Arg Pro Ser Trp Ile Pro Glu Arg Phe Ser Gly Ser
                50                      55                  60

Asn Ser Gly Asn Thr Ala Thr Leu Thr Ile Ser Arg Gly Glu Ala Gly
                65                      70                  75                  80

Asp Glu Ala Asp Tyr Tyr Cys Gln Val Trp Asp Ser Ser Ser Asp His
                                85                  90                  95

Val Val Phe Gly Gly Gly Thr Lys Leu Thr Val Leu Gly Gln Pro Lys
                            100                 105                 110

Ala Ala Pro Ser Val Thr Leu Phe Pro Pro Ser Ser Glu Glu Leu Gln
                            115                 120                 125

Ala Asn Lys Ala Thr Leu Val Cys Leu Ile Ser Asp Phe Tyr Pro Gly
                            130                 135                 140

Ala Val Thr Val Ala Trp Lys Ala Asp Ser Ser Pro Val Lys Ala Gly
                145                     150                 155                 160

Val Glu Thr Thr Thr Pro Ser Lys Gln Ser Asn Asn Lys Tyr Ala Ala
                                165                 170                 175

Ser Ser Tyr Leu Ser Leu Thr Pro Glu Gln Trp Lys Ser His Arg Ser
                            180                 185                 190

Tyr Ser Cys Gln Val Thr His Glu Gly Ser Thr Val Glu Lys Thr Val
                            195                 200                 205

Ala Pro Thr Glu Cys Ser
                210
```

TREATMENT OF ASTHMA WITH ANTI-TSLP ANTIBODY

CROSS REFERENCE TO RELATED APPLICATIONS

The present application claims the priority benefit of U.S. Provisional Patent Application No. 62/484,864, filed Apr. 12, 2017, U.S. Provisional Patent Application No. 62/553,477, filed Sep. 1, 2017 and U.S. Provisional Patent Application No. 62/553,575, filed Sep. 1, 2017, hereby incorporated by reference in their entirety.

FIELD OF THE INVENTION

The present disclosure relates, in general, to methods of treating asthma, including severe asthma, eosinophilic asthma and non/low eosoniphilic asthma, using an antibody specific for thymic stromal lymphopoietin (TSLP).

BACKGROUND

Asthma affects an estimated 315 million people worldwide.[1] Of these, approximately 10 to 15% have severe asthma[2] and as many as 60% have inadequately controlled disease.[3] These patients are at risk for significantly impaired quality of life and recurrent severe exacerbations. Asthma therapies, including inhaled corticosteroids (ICS) combined with long-acting beta-2 agonists (LABA), may not provide adequate disease control, particularly in patients with severe disease.[2,4,5] The heterogeneous response to asthma treatment, in part, may be related to differences in patterns of airway inflammation and resistance to corticosteroids.[2,5,6] Alternative treatments that inhibit specific molecular targets, including immunoglobulin E (IgE), interleukin-4, interleukin-5, interleukin-13, and their respective receptors, have been shown to benefit some patients with asthma who are not fully controlled on optimal ICS/LABA therapy.[7-18]

Thymic stromal lymphopoietin (TSLP), an epithelial cell-derived cytokine produced in response to environmental and pro-inflammatory stimuli, leads to the activation of multiple inflammatory cells and downstream pathways.[19,20] TSLP is increased in the airways of patients with asthma and correlates with Th2 cytokine and chemokine expression[21] and disease severity.[22,23] While TSLP is central to the regulation of Th2 immunity, it may also play a key role in other pathways of inflammation and therefore be relevant to multiple asthma phenotypes.

Tezepelumab is an human immunoglobulin G2 (IgG2) monoclonal antibody (mAb) that binds to TSLP, preventing its interaction with the TSLP receptor complex. A proof-of-concept study in patients with mild, atopic asthma, demonstrated that tezepelumab inhibited the early and late asthmatic responses and suppressed biomarkers of Th2 inflammation following inhaled allergen challenge.[24]

The present disclosure describes a randomized, placebo-controlled, dose-ranging trial of tezepelumab in patients whose disease was inadequately controlled with medium to high doses of ICS/LABA.

SUMMARY

The anti-TSLP antibody described herein addresses an unmet need in asthma patients in which other medications may not control moderate to severe asthma. For example, the antibody therapy may improve asthma in eosinophil (EOS)-low patients and may provide a more powerful exacerbation reduction in EOS-high patients.

The disclosure provides a method for treating asthma in a subject comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises a. a light chain variable domain comprising: i. a light chain CDR1 sequence comprising the amino acid sequence set forth in SEQ ID NO:3; ii. a light chain CDR2 sequence comprising the amino acid sequence set forth in SEQ ID NO:4; iii. a light chain CDR3 sequence comprising the amino acid sequence set forth in SEQ ID NO:5; and b. a heavy chain variable domain comprising: i. a heavy chain CDR1 sequence comprising the amino acid sequence set forth in SEQ ID NO:6; ii. a heavy chain CDR2 sequence comprising the amino acid sequence set forth in SEQ ID NO:7, and iii. a heavy chain CDR3 sequence comprising the amino acid sequence set forth in SEQ ID NO:8, wherein the antibody specifically binds to a TSLP polypeptide as set forth in amino acids 29-159 of SEQ ID NO:2.

Also contemplated is a method for treating asthma in a subject comprising administering a therapeutically effective amount of an anti-TSLP antibody or antibody variant in a dose of 70 mg to 280 mg at an interval of every two weeks, wherein both binding sites of the antibody have identical binding to TSLP, and the antibody comprises a. a light chain variable domain selected from the group consisting of: i. a sequence of amino acids at least 80% identical to SEQ ID NO:12; ii. a sequence of amino acids encoded by a polynucleotide sequence that is at least 80% identical to SEQ ID NO:11; iii. a sequence of amino acids encoded by a polynucleotide that hybridizes under moderately stringent conditions to the complement of a polynucleotide consisting of SEQ ID NO:11; and b. a heavy chain variable domain selected from the group consisting of: i. a sequence of amino acids that is at least 80% identical to SEQ ID NO:10; ii. a sequence of amino acids encoded by a polynucleotide sequence that is at least 80% identical to SEQ ID NO:9; iii. a sequence of amino acids encoded by a polynucleotide that hybridizes under moderately stringent conditions to the complement of a polynucleotide consisting of SEQ ID NO:9; or c. a light chain variable domain of (a) and a heavy chain variable domain of (b), wherein the antibody specifically binds to a TSLP polypeptide as set forth in amino acids 29-159 of SEQ ID NO:2.

In various embodiments, the antibody or antibody variant is administered every 4 weeks.

In various embodiments, the antibody or antibody variant is administered at a dose of 70 mg, at a dose of 210 mg or at a dose of 280 mg every 2 weeks or every 4 weeks.

The disclosure also provides a method for treating asthma in a subject comprising administering a therapeutically effective amount of an anti-TSLP antibody or antibody variant in a dose of 210 mg at an interval of every 4 weeks, wherein both binding sites of the antibody have identical binding to TSLP, and the antibody comprises a. a light chain variable domain comprising: i. a light chain CDR1 sequence comprising the amino acid sequence set forth in SEQ ID NO:3; ii. a light chain CDR2 sequence comprising the amino acid sequence set forth in SEQ ID NO:4; iii. a light chain CDR3 sequence comprising the amino acid sequence set forth in SEQ ID NO:5; and b. a heavy chain variable domain comprising: i. a heavy chain CDR1 sequence comprising the amino acid sequence set forth in SEQ ID NO:6; ii. a heavy chain CDR2 sequence comprising the amino acid sequence set forth in SEQ ID NO:7, and iii. a heavy chain CDR3 sequence comprising the amino acid sequence set forth in SEQ ID NO:8, wherein the antibody specifically binds to a TSLP polypeptide as set forth in amino acids 29-159 of SEQ ID NO:2.

The disclosure further provides a method for treating asthma in a subject comprising administering a therapeutically effective amount of an anti-TSLP antibody or antibody variant in a dose of 210 mg at an interval of every 4 weeks, wherein both binding sites of the antibody have identical binding to TSLP, and the antibody comprises a. a light chain variable domain selected from the group consisting of: i. a sequence of amino acids at least 80% identical to SEQ ID NO:12; ii. a sequence of amino acids encoded by a polynucleotide sequence that is at least 80% identical to SEQ ID NO:11; iii. a sequence of amino acids encoded by a polynucleotide that hybridizes under moderately stringent conditions to the complement of a polynucleotide consisting of SEQ ID NO:11; and b. a heavy chain variable domain selected from the group consisting of: i. a sequence of amino acids that is at least 80% identical to SEQ ID NO:10; ii. a sequence of amino acids encoded by a polynucleotide sequence that is at least 80% identical to SEQ ID NO:9; iii. a sequence of amino acids encoded by a polynucleotide that hybridizes under moderately stringent conditions to the complement of a polynucleotide consisting of SEQ ID NO:9; or c. a light chain variable domain of (a) and a heavy chain variable domain of (b), wherein the antibody specifically binds to a TSLP polypeptide as set forth in amino acids 29-159 of SEQ ID NO:2.

In various embodiments, the anti-TSLP antibody variant has substantially similar pK characteristics as tezepelumab in humans.

In various embodiments, the antibody or antibody variant is administered for a period of at least 4 months, 6 months, 9 months, 1 year or more.

In various embodiments, the anti-TSLP antibody or antibody variant thereof is bivalent and selected from the group consisting of a human antibody, a humanized antibody, a chimeric antibody, a monoclonal antibody, a recombinant antibody, an antigen-binding antibody fragment, a single chain antibody, a monomeric antibody, a diabody, a triabody, a tetrabody, a Fab fragment, an IgG1 antibody, an IgG2 antibody, an IgG3 antibody, and an IgG4 antibody.

In one embodiment, the anti-TSLP antibody variant is selected from the group consisting of a diabody, a triabody, a tetrabody, a Fab fragment, a single domain antibody, an scFv, wherein the dose is adjusted such that the binding sites are equimolar to those dosed by bivalent antibodies.

In various embodiments, the antibody is an IgG2 antibody.

In one embodiment, the antibody or antibody variant is a human antibody.

In various embodiments, the antibody is tezepelumab. In various embodiments, the tezepelumab is an IgG2 antibody having the full length heavy and light chain amino acid sequences set out in SEQ ID NOs: 105 and 106, respectively.

In various embodiments, the antibody or antibody variant further comprises a pharmaceutically acceptable carrier or excipient.

In various embodiments, the asthma is severe asthma. It is further contemplated that the asthma is eosinophilic or non-eosinophilic asthma, optionally the asthma is low eosinophil asthma.

Data presented herein demonstrates an anti-TSLP antibody that substantially affects two important markers of inflammation of asthma: blood eosinophil counts and the fraction of exhaled nitric oxide. The data show that an anti-TSLP antibody reduces the level of both inflammatory markers, reduces the asthma exacerbation rate, improves lung function irrespective of asthma phenotype (eosinophilic (allergic and nonallergic) and noneosinophilic/low eosinophilic asthma), and blocks at least two important inflammatory pathways in asthma. The anti-TSLP antibody, therefore, is able to treat a patient having either asthma phenotype: eosinophilic (allergic and nonallergic) or noneosinophilic/low eosinophilic asthma. Accordingly, provided herein is a method of treating a patient having low eosinophil asthma comprising administering an anti-TSLP antibody as described herein. Also contemplated is a method for treating a subject having asthma characterized by a low Th2 profile comprising administering an anti-TSLP antibody. In various embodiments, the antibody is tezepelumab or another anti-TSLP antibody described in the art. Exemplary antibodies are described further in the Detailed Description.

In various embodiments, the subject is an adult. In various embodiments, the subject is a child or adolescent.

It is contemplated that administration of the anti-TSLP antibody or antibody variant decreases eosinophils in blood, sputum, broncheoalveolar fluid, or lungs of the subject.

It is further contemplated that administration of the anti-TSLP antibody or antibody variant shifts cell counts in the subject from a Th2 high population to a Th2 low population.

In various embodiments, administration of the anti-TSLP antibody or antibody variant improves one or more measures of asthma in a subject selected from the group consisting of forced expiratory volume (FEV), $FEV_1$ reversibility, forced vital capacity (FVC), FeNO, Asthma Control Questionnaire-6 score and AQLQ(S)+12 score.

In one embodiment, the administration improves one or more symptoms of asthma as measured by an asthma symptom diary.

Further provided is a method for treating asthma in a subject comprising administering a therapeutically effective amount of an anti-TSLP antibody or antibody variant in a dose of 70 to 280 mg at an interval of every 2 weeks, wherein both binding sites of the antibody have identical binding to TSLP, and the antibody comprises a. a light chain variable domain comprising: i. a light chain CDR1 sequence comprising the amino acid sequence set forth in SEQ ID NO:3; ii. a light chain CDR2 sequence comprising the amino acid sequence set forth in SEQ ID NO:4; iii. a light chain CDR3 sequence comprising the amino acid sequence set forth in SEQ ID NO:5; and b. a heavy chain variable domain comprising: i. a heavy chain CDR1 sequence comprising the amino acid sequence set forth in SEQ ID NO:6; ii. a heavy chain CDR2 sequence comprising the amino acid sequence set forth in SEQ ID NO:7, and iii. a heavy chain CDR3 sequence comprising the amino acid sequence set forth in SEQ ID NO:8, wherein the antibody specifically binds to a TSLP polypeptide as set forth in amino acids 29-159 of SEQ ID NO:2, wherein the antibody is an IgG2 antibody.

In various embodiments, the IgG2 the antibody is administered every 2 weeks or every 4 weeks.

In various embodiments, the IgG2 antibody is administered at a dose of 70 mg, 210 mg or 280 mg every 2 weeks or every 4 weeks.

Also provided is a method of reducing the frequency of asthma exacerbation in a subject comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises a. a light chain variable domain comprising: i. a light chain CDR1 sequence comprising the amino acid sequence set forth in SEQ ID NO:3; ii. a light chain CDR2 sequence comprising the amino acid sequence set forth in SEQ ID NO:4; iii. a light chain CDR3 sequence comprising the amino acid sequence set forth in SEQ ID NO:5; and b. a heavy chain variable domain comprising: i. a heavy chain CDR1 sequence comprising the amino acid sequence set forth in SEQ ID NO:6; ii. a heavy chain CDR2 sequence comprising the amino acid sequence set forth in SEQ ID NO:7, and iii. a heavy chain CDR3 sequence comprising the amino acid sequence set forth in SEQ ID NO:8, wherein the antigen binding protein specifically binds to a TSLP polypeptide as set forth in amino acids 29-159 of SEQ ID NO:2.

Further contemplated is a method of reducing the frequency of asthma exacerbation in a subject comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises a. a light chain variable domain selected from the group consisting of: i. a sequence of amino acids at least 80% identical to SEQ ID NO:12; ii. a sequence of amino acids encoded by a polynucleotide sequence that is at least 80% identical to SEQ ID NO:11; iii. a sequence of amino acids encoded by a polynucleotide that hybridizes under moderately stringent conditions to the complement of a polynucleotide consisting of SEQ ID NO:11; and b. a heavy chain variable domain selected from the group consisting of: i. a sequence of amino acids that is at least 80% identical to SEQ ID NO:10; ii. a sequence of amino acids encoded by a polynucleotide sequence that is at least 80% identical to SEQ ID NO:9; iii. a sequence of amino acids encoded by a polynucleotide that hybridizes under moderately stringent conditions to the complement of a polynucleotide consisting of SEQ ID NO:9; or c. a light chain variable domain of (a) and a heavy chain variable domain of (b).

It is contemplated that the dosing and antibody and antibody variant types referenced above apply to each method contemplated herein.

In various embodiments, the antibody or antibody variant further comprises a pharmaceutically acceptable carrier or excipient.

In various embodiments, the administration delays the time to an asthma exacerbation compared to a subject not receiving the anti-TSLP antibody.

In various embodiments, the administration reduces frequency of or levels of co-administered therapy in the subject. Optionally, the co-administered therapy is inhaled corticosteroids (ICS), long-acting β2 agonist (LABA), leukotriene receptor antagonists (LTRA), long-acting anti-muscarinics (LAMA), cromones, short-acting β2 agonist (SABA), and theophylline or oral corticosteroids.

In various embodiments, the administration eliminates the need for corticosteroid therapy.

In various embodiments, the administration is subcutaneous or intravenous.

Also provided herein is a method of treating chronic obstructive pulmonary disease (COPD) comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises a. a light chain variable domain comprising: i. a light chain CDR1 sequence comprising the amino acid sequence set forth in SEQ ID NO:3; ii. a light chain CDR2 sequence comprising the amino acid sequence set forth in SEQ ID NO:4; iii. a light chain CDR3 sequence comprising the amino acid sequence set forth in SEQ ID NO:5; and b. a heavy chain variable domain comprising: i. a heavy chain CDR1 sequence comprising the amino acid sequence set forth in SEQ ID NO:6; ii. a heavy chain CDR2 sequence comprising the amino acid sequence set forth in SEQ ID NO:7, and iii. a heavy chain CDR3 sequence comprising the amino acid sequence set forth in SEQ ID NO:8, wherein the antigen binding protein specifically binds to a TSLP polypeptide as set forth in amino acids 29-159 of SEQ ID NO:2.

Also provided is a method of treating chronic obstructive pulmonary disease (COPD) in a subject comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises a. a light chain variable domain selected from the group consisting of: i. a sequence of amino acids at least 80% identical to SEQ ID NO:12; ii. a sequence of amino acids encoded by a polynucleotide sequence that is at least 80% identical to SEQ ID NO:11; iii. a sequence of amino acids encoded by a polynucleotide that hybridizes under moderately stringent conditions to the complement of a polynucleotide consisting of SEQ ID NO:11; and b. a heavy chain variable domain selected from the group consisting of: i. a sequence of amino acids that is at least 80% identical to SEQ ID NO:10; ii. a sequence of amino acids encoded by a polynucleotide sequence that is at least 80% identical to SEQ ID NO:9; iii. a sequence of amino acids encoded by a polynucleotide that hybridizes under moderately stringent conditions to the complement of a polynucleotide consisting of SEQ ID NO:9; or c. a light chain variable domain of (a) and a heavy chain variable domain of (b).

Also provided herein is a method for reducing ACQ-6 score in a subject comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises a. a light chain variable domain comprising: i. a light chain CDR1 sequence comprising the amino acid sequence set forth in SEQ ID NO:3; ii. a light chain CDR2 sequence comprising the amino acid sequence set forth in SEQ ID NO:4; iii. a light chain CDR3 sequence comprising the amino acid sequence set forth in SEQ ID NO:5; and b. a heavy chain variable domain comprising: i. a heavy chain CDR1 sequence comprising the amino acid sequence set forth in SEQ ID NO:6; ii. a heavy chain CDR2 sequence comprising the amino acid sequence set forth in SEQ ID NO:7, and iii. a heavy chain CDR3 sequence comprising the amino acid sequence set forth in SEQ ID NO:8, wherein the antigen binding protein specifically binds to a TSLP polypeptide as set forth in amino acids 29-159 of SEQ ID NO:2.

Further provided is a method for reducing ACQ-6 score in a subject comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises a. a light chain variable domain selected from the group consisting of: i. a sequence of amino acids at least 80% identical to SEQ ID NO:12; ii. a sequence of amino acids encoded by a polynucleotide sequence that is at least 80% identical to SEQ ID NO:11; iii. a sequence of amino acids encoded by a polynucleotide that hybridizes under moderately stringent conditions to the complement of a polynucleotide consisting of SEQ ID NO:11; and b. a heavy chain variable domain selected from the group consisting of: i. a sequence of amino acids that is at least 80% identical to SEQ ID NO:10; ii. a sequence of amino acids encoded by a polynucleotide sequence that is at least 80% identical to SEQ ID NO:9; iii. a sequence of amino acids encoded by a polynucleotide that hybridizes under moderately stringent conditions to the complement of a polynucleotide consisting of SEQ ID NO:9; or c. a light chain variable domain of (a) and a heavy chain variable domain of (b).

Provided herein is a method for reducing ACQ-6 score in a subject having a low eosinophil profile comprising administering a therapeutically effective amount of an anti-TSLP antibody or antibody variant, wherein the antibody or antibody variant binding to TSLP inhibits TSLP activity. Also provided is a method for reducing ACQ-6 score in a subject having a Th2 low profile comprising administering a therapeutically effective amount of an anti-TSLP antibody or antibody variant, wherein the antibody or antibody variant binding to TSLP inhibits TSLP activity.

Also contemplated is a method for treating asthma in a subject, including severe asthma, eosinophilic or non-eosinophilic asthma and low eosinophil asthma comprising administering a therapeutically effective amount of an anti-TSLP antibody or antibody variant, wherein the antibody or antibody variant binding to TSLP inhibits TSLP activity.

In various embodiments, the subject has an eosinophil count less than 250 cells/4 at start of treatment.

Also provided is a method for treating asthma in a subject having a Th2 low profile comprising administering a therapeutically effective amount of an anti-TSLP antibody or antibody variant, wherein the antibody or antibody variant binding to TSLP inhibits TSLP activity.

In various embodiments, the subject has a Th2 profile of IgE less than or equal to 100 IU/ml or eosinophil count of less than 140 cells/µL at the time of diagnosis.

In various embodiments, the antibody is tezepelumab or another anti-TSLP antibody described in the art, e.g., in Table A. Exemplary antibodies are described further in the Detailed Description.

BRIEF DESCRIPTION OF THE DRAWINGS

FIG. 1A, asthma exacerbation rate; FIG. 1B, changes from baseline in the postbronchodilator FEV1; FIG. 1C, change from baseline in ACQ-6; FIG. 1D, change from baseline in AQLQ score.

FIGS. 2A-2B show the effects of antibody treatment in patients receiving glucocorticoids. FIG. 2A: Lines within the squares represent the median, the diamond symbol represents the mean, the boxes represent the 25$^{th}$ to 75$^{th}$ percentile and the whiskers represent the range (highest and lowest value). FIG. 2B: Histogram of baseline inhaled glucocorticoid dose (fluticasone equivalents).

FIG. 3 shows a Kaplan-Meier Curve for Time to First Asthma Exacerbation through Week 52 in the Intention-to-Treat population. *P-values are nominal and without multiplicity adjustment FIGS. 4A-4B show the change from baseline in peripheral blood eosinophils (cell/µl) (FIG. 4A), and total IgE (IU/ml) (FIG. 4B), over time in the Intention-to-Treat population.

FIG. 5 shows the change from baseline in the fraction of exhaled nitric oxide (FENO) in treated subjects.

FIGS. 6A-6B show annualized rate of asthma exacerbations, according to Baseline Biomarker Status at Week 52 (FIG. 6A), and change from baseline in the fraction of exhaled nitric oxide (FENO) (FIG. 6B). In FIG. 6A, nominal two-sided P values of less than 0.05 for the comparison with the placebo group are shown. A clinically meaningful cutoff of 24 ppb was used for the FeNO subpopulation analysis. A high status with respect to type 2 helper T (Th2) cells was defined as an IgE level of more than 100 IU per milliliter and a blood eosinophil count of 140 cells or more per microliter; a low Th2 status was defined as an IgE level of 100 IU or less per milliliter or a blood eosinophil count of less than 140 cells per microliter.

FIG. 7 (Table 1A) describes subject inclusion and exclusion criteria.

FIG. 8 (Table 1B) describes baseline demographics and clinical characteristics in the Intention-To-Treat population.

FIG. 9 (Table 2) shows annualized asthma exacerbation rate reduction, and change from baseline in FEV1, ACQ and AQLQ in the eosinophil sub-populations <250 cells/µl and ≥250 cells/µl.

FIG. 10 (Table 3) shows change from baseline in ACQ-6 (week 50) and AQLQ(S)+12 (week 48) in the Intention-to-Treat population.

FIG. 11 (Table 4) shows the annualized asthma exacerbation rate reduction and change from baseline in FEV1 (week 52), ACQ-6 (week 50), and AQLQ(S)+12 (week 48) in patient sub-populations: Th2 status, serum periostin.

FIG. 12 (Table 5) shows the annualized asthma exacerbation rate reduction and change from baseline in $FEV_1$ (week 52), ACQ-6 (week 50), and AQLQ(S)+12 (week 48) in patient sub-populations: FENO, allergic status, current post-BD reversibility.

FIG. 13 (Table 6) shows the change from baseline in post-BD $FEV_1$ and pre- and post-BD forced vital capacity at week 52 in the Intention-To-Treat population.

FIG. 14 (Table 7) shows the annualized rate of severe asthma exacerbations, time to first asthma exacerbation/severe asthma exacerbation, and proportion of patients with one or more asthma exacerbation at week 52 in the Intention-To-Treat population.

FIG. 15 (Table 8) is a post-hoc analysis of annualized asthma exacerbation rate reduction stratified by blood eosinophil count <400 cells/µl vs≥400 cells/µl through week 52.

FIG. 16 (Table 9) shows the annualized asthma exacerbation rate reduction stratified by Patients on a medium- or high-dose of inhaled glucocorticoid and by patients on maintenance oral glucocorticoids through week 52.

FIG. 17 (Table 10) shows annualized asthma exacerbation rate reduction stratified by number of prior asthma exacerbations and by smoking history* through week 52.

FIG. 18 (Table 11) shows the change from baseline in Medimmune ASMA score at week 52.

FIG. 19 (Table 12) shows all treatment-emergent serious adverse events in the as-treated population.

DETAILED DESCRIPTION

Figure 1A:
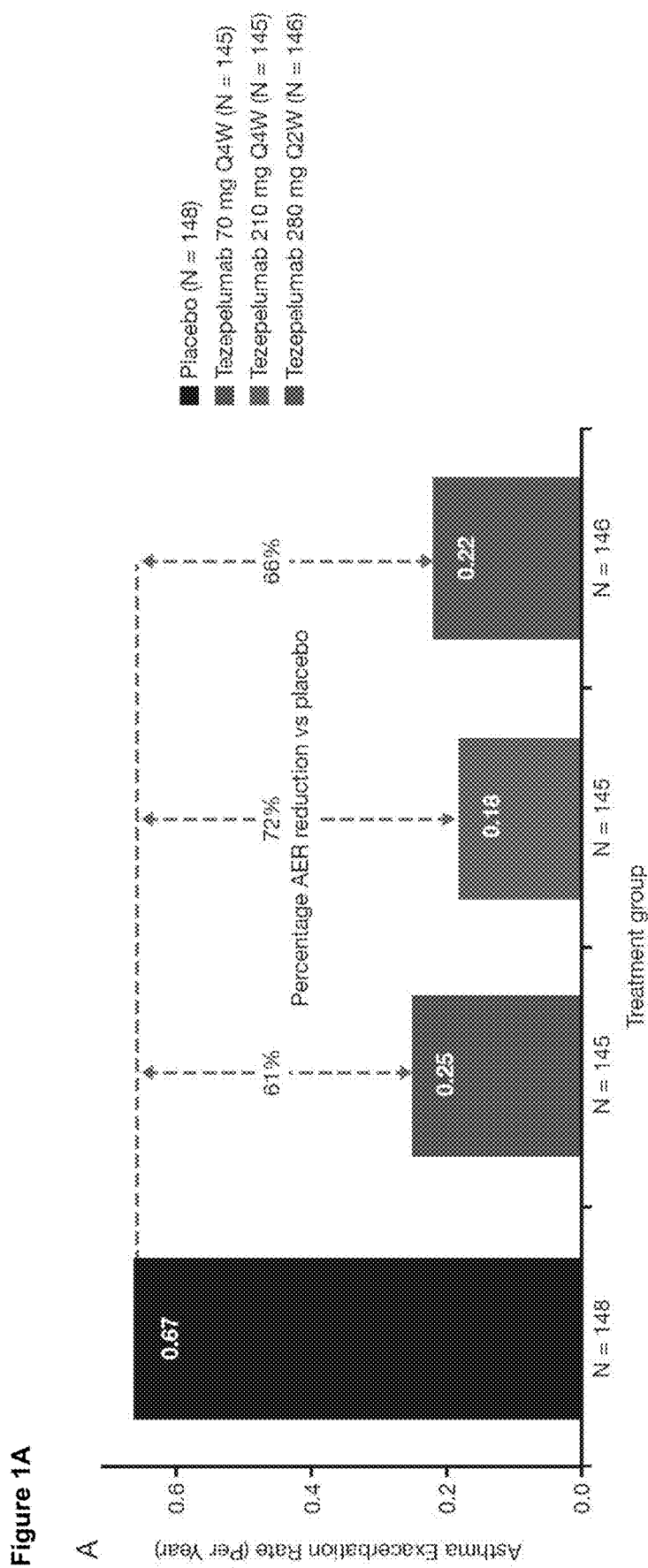
FIGS. 1A-1D show the effects of antibody treatment at the different doses in various measures of asthma symptoms.

Use of an anti-TSLP antibody addresses an unmet need in asthma patients in which other medications may not control moderate to severe asthma. For example anti-TSLP antibody tezepelumab might reduce exacerbations in both in eosinophil (EOS)-low and high in EOS-high patients. It is further contemplated that treatment with tezepelumab could eliminate daily disease activity and make more patients steroid-free or reduce the need for use of steroids in the treatment of asthma.

Definitions

Unless otherwise stated, the following terms used in this application, including the specification and claims, have the definitions given below.

As used in the specification and the appended claims, the indefinite articles "a" and "an" and the definite article "the" include plural as well as singular referents unless the context clearly dictates otherwise.

Unless otherwise defined, all technical and scientific terms used herein have the same meaning as commonly understood by one of ordinary skill in the art to which the present disclosure belongs. The following references provide one of skill with a general definition of many of the terms used in this disclosure include, but are not limited to: Singleton et al., DICTIONARY OF MICROBIOLOGY AND MOLECULAR BIOLOGY (2d Ed. 1994); THE CAMBRIDGE DICTIONARY OF SCIENCE AND TECHNOLOGY (Walker Ed., 1988); THE GLOSSARY OF GENETICS, 5th Ed., R. Rieger et al. (Eds.), Springer Verlag (1991); and Hale & Marham, THE HARPER COLLINS DICTIONARY OF BIOLOGY (1991).

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

The term "asthma" as used herein refers to allergic, non-allergic, eosinophilic, and non-eosinophillic asthma.

The term "allergic asthma" as used herein refers to asthma that is triggered by one or more inhaled allergens. Such patients have a positive IgE fluorescence enzyme immunoassay (FEIA) level to one or more allergens that trigger an asthmatic response.

Typically, most allergic asthma is associated with Th2-type inflammation.

The term "non-allergic asthma" refers to patients that have low eosinophil, low Th2, or low IgE at the time of diagnosis. A patient who has "non-allergic asthma" is typically negative in the IgE fluorescence enzyme immunoassay (FEIA) in response to a panel of allergens, including region-specific allergens. In addition to low IgE, those patients often have low or no eosinophil counts and low Th2 counts at the time of diagnosis.

The term "severe asthma" as used herein refers to asthma that requires high intensity treatment (e.g., GINA Step 4 and Step 5) to maintain good control, or where good control is not achieved despite high intensity treatment (GINA, Global Strategy for Asthma Management and Prevention. Global Initiative for Asthma (GINA) December 2012).

The term "eosinophilic asthma" as used herein refers to an asthma patient having a screening blood eosinophil count of ≥250 cells/μL. "Low eosinophilic" asthma refers to asthma patients having less than 250 cells/uL blood or serum.

The term "Th2-type inflammation" as used herein refers to a subject having a screening blood eosinophil count ≥140 cells/μL and a screening total serum IgE level of >100 IU/mL (Corren et al, N Engl J Med. 22; 365(12):1088-98, 2011). A "Th2 high" asthma population or profile refers to a subject having IgE>100 IU/mL and Blood Eosinophil Count 140 cells/μL. A "Th2 low" asthma population refers to a subject having IgE<100 IU/mL and Blood Eosinophil Count 140 cells/μL An "elevated FeNO" (Fractional exhaled nitric oxide) as used herein refers to a baseline FeNO measurement greater than or equal to the median from all randomized subjects in the study. Elevated FeNO refers to FeNO levels of 24 or above.

The term "elevated serum periostin level" as used herein refers to a patient having a baseline serum periostin level greater than or equal to the median from all randomized subjects in the study. Periostin has been shown to be involved in certain aspects of allergic inflammation, including eosinophil recruitment, airway remodeling, and development of a Th2 phenotype (Li et al., Respir Res. 16(1):57, 2015).

The term "current post-bronchodilator (BD) forced expiratory volume in 1 second ($FEV_1$) reversibility" as used herein refers to a post-BD change in $FEV_1$ of ≥12% and ≥200 mL The term "asthma exacerbation" as used herein refers to a worsening of asthma that leads to any of the following: Use of systemic corticosteroids for at least 3 days; a single depo-injectable dose of corticosteroids is considered equivalent to a 3-day course of systemic corticosteroids; for subjects receiving maintenance OCS, a temporary doubling of the maintenance dose for at least 3 days qualifies; an ED visit due to asthma that required systemic corticosteroids (as per above); an inpatient hospitalization due to asthma. Additional measures associated with asthma exacerbations are also being examined to determine effect. These include hospitalizations related to asthma exacerbations (i.e., severe asthma exacerbations), time to first asthma exacerbation, and the proportion of subjects with one or more asthma exacerbation/severe asthma exacerbation.

The term "worsening of asthma" refers to new or increased symptoms and/or signs (examination or lung function) that can be either concerning to the subject (subject-driven) or related to an Asthma Daily Diary alert (diary-driven) via the ePRO device. Asthma-worsening thresholds include: decrease in morning peak flow ≥30% on at least 2 of 3 successive days compared with baseline (last 7 days of run-in), and/or a ≥50% increase in rescue medication (minimum increase of 2 or more puffs, or one new or additional nebulized β2 agonist) on at least 2 of 3 successive days compared with the average use for the previous week, and/or nocturnal awakening due to asthma requiring rescue medication use for at least 2 of 3 successive nights, and/or an increase in total asthma symptom score (the sum of daytime [evening assessment] and nighttime [morning assessment]) of at least 2 units above the screening/run-in period average (last 10 days of screening/run-in), or the highest possible score (daily score of 6), on at least 2 of 3 successive days.

The term "cytokine" as used herein refers to one or more small (5-20 kD) proteins released by cells that have a specific effect on interactions and communications between cells or on the behavior of cells, such as immune cell proliferation and differentiation. Functions of cytokines in the immune system include, promoting influx of circulating leukocytes and lymphocytes into the site of immunological encounter; stimulating the development and proliferation of B cells, T cells, peripheral blood mononuclear cells (PBMCs) and other immune cells; and providing antimicrobial activity. Exemplary immune cytokines, include but are not limited to, IL-1, IL-2, IL-3, IL-4, IL-5, IL-6, IL-7, IL-9, IL-10, IL-12, IL-13, IL-15, IL17A, IL-17F, IL-18, IL-21, IL-22, interferon (including IFN alpha, beta, and gamma), tumor necrosis factor (including TNF alpha, beta), transforming growth factor (including TGF alpha, beta), granulocyte colony stimulating factor (GCSF), granulocyte macrophage colony stimulating factor (GMCSF) and thymic stromal lymphopoietin (TSLP).

A "T helper (Th) 1 cytokine" or "Th1-specific cytokine" refers to cytokines that are expressed (intracellularly and/or secreted) by Th1 T cells, and include IFN-g, TNF-α, and IL-12. A "Th2 cytokine" or "Th2-specific cytokine" refers to cytokines that are expressed (intracellularly and/or secreted) by Th2 T cells, including IL-4, IL-5, IL-13, and IL-10. A "Th17 cytokine" or "Th17-specific cytokine" refers to cytokines that are expressed (intracellularly and/or secreted) by Th17 T cells, including IL-17A, IL-17F, IL-22 and IL-21. Certain populations of Th17 cells express IFN-g and/or IL-2 in addition to the Th17 cytokines listed herein. A polyfunctional CTL cytokine includes IFN-g, TNF-a, IL-2 and IL-17.

The term "specifically binds" is "antigen specific", is "specific for", "selective binding agent", "specific binding agent", "antigen target" or is "immunoreactive" with an antigen refers to an antibody or polypeptide that binds an target antigen with greater affinity than other antigens of similar sequence. It is contemplated herein that the agent specifically binds target proteins useful in identifying immune cell types, for example, a surface antigen (e.g., T cell receptor, CD3), a cytokine (e.g., TSLP, IL-4, IL-5, IL-13, IL-17, IFN-g, TNF-a) and the like. In various embodiments, the antibody specifically binds the target antigen, but can cross-react with an ortholog of a closely related species, e.g. an antibody may being human protein and also bind a closely related primate protein.

The term "antibody" or "immunoglobulin" refers to a tetrameric glycoprotein that consists of two heavy chains and two light chains, each comprising a variable region and a constant region. "Heavy Chains" and "Light Chains" refer to substantially full length canonical immunoglobulin light and heavy chains (see e.g., Immunobiology, 5th Edition (Janeway and Travers et al., Eds., 2001). Antigen-binding portions may be produced by recombinant DNA techniques or by enzymatic or chemical cleavage of intact antibodies. The term "antibody" includes monoclonal antibodies, polyclonal antibodies, chimeric antibodies, human antibodies, and humanized antibodies.

Antibody variants include antibody fragments and antibody like proteins with changes to structure of canonical tetrameric antibodies. Typically antibody variants include V regions with a change to the constant regions, or, alternatively, adding V regions to constant regions, optionally in a non-canonical way. Examples include multispecific antibodies (e.g., bispecific antibodies with extra V regions), antibody fragments that can bind an antigen (e.g., Fab', F'(ab)2, Fv, single chain antibodies, diabodies), biparatopic and recombinant peptides comprising the forgoing as long as they exhibit the desired biological activity.

Antibody fragments include antigen-binding portions of the antibody including, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), an antigen-binding-domain immunoglobulin fusion protein, single domain antibodies (including camelized antibody), a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired biological activity.

"Valency" refers to the number of antigen binding sites on each antibody or antibody fragment that targets an epitope. A typical full length IgG molecule, or $F(ab)_2$ is "bivalent" in that it has two identical target binding sites. A "monovalent" antibody fragment such as a F(ab)' or scFc with a single antigen binding site. Trivalent or tetravalent antigen binding proteins can also be engineered to be multivalent.

"Monoclonal antibody" refers to an antibody obtained from a population of substantially homogeneous antibodies, i.e., the individual antibodies comprising the population are identical except for possible naturally occurring mutations that may be present in minor amounts.

The term "inhibits TSLP activity" includes inhibiting any one or more of the following: binding of TSLP to its receptor; proliferation, activation, or differentiation of cells expressing TSLPR in the presence of TSLP; inhibition of Th2 cytokine production in a polarization assay in the presence of TSLP; dendritic cell activation or maturation in the presence of TSLP; and mast cell cytokine release in the presence of TSLP. See, e.g., U.S. Pat. No. 7,982,016 B2, column 6 and example 8 and US 2012/0020988 A1, examples 7-10.

The term "sample" or "biological sample" refers to a specimen obtained from a subject for use in the present methods, and includes urine, whole blood, plasma, serum, saliva, sputum, tissue biopsies, cerebrospinal fluid, peripheral blood mononuclear cells with in vitro stimulation, peripheral blood mononuclear cells without in vitro stimulation, gut lymphoid tissues with in vitro stimulation, gut lymphoid tissues without in vitro stimulation, gut lavage, bronchioalveolar lavage, nasal lavage, and induced sputum.

The terms "treat", "treating" and "treatment" refer to eliminating, reducing, suppressing or ameliorating, either temporarily or permanently, either partially or completely, a clinical symptom, manifestation or progression of an event, disease or condition associated with an inflammatory disorder described herein. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method for determining the efficacy of treatment comprising administering to a patient therapeutic agent in an amount and for a time sufficient to induce a sustained improvement over baseline of an indicator that reflects the severity of the particular disorder.

The term "therapeutically effective amount" refers to an amount of therapeutic agent that is effective to ameliorate or lessen symptoms or signs of disease associated with a disease or disorder.

Asthma

Asthma is a chronic inflammatory disorder of the airways. Each year, asthma accounts for an estimated 1.1 million outpatient visits, 1.6 million emergency room visits, 444,000 hospitalizations (Defrances et al, 2008) Available at: http://www.cdc.gov/nchs/data/nhsr/nhsr005.pdf, and 3,500 deaths in the U.S. In susceptible individuals, asthmatic inflammation causes recurrent episodes of wheezing, breathlessness, chest tightness, and cough. The etiology of asthma is thought to be multi-factorial, influenced by both genetic environmental mechanisms,[1,2] with environmental allergens an important cause.[2,3] The majority of cases arise when a person becomes hypersensitive to allergens (atopy). Atopy is characterized by an increase in Th2 cells and Th2 cytokine expression and IgE production. Approximately 10 million patients in the United States are thought to have allergy-induced asthma. Despite the available therapeutic options, asthma continues to be a major health problem. Worldwide, asthma currently affects approximately 300 million people; by 2020, asthma is expected to affect 400 million people (Partridge, Eur Resp Rev. 16:67-72, 2007).

Allergen inhalation by atopic asthmatics induces some of the manifestations of asthma, including reversible airflow obstruction, airway hyperresponsiveness, and eosinophilic and basophilic airway inflammation. Allergen inhalation challenge has become the predominant model of asthma in many species (Bates et al., Am J Physiol Lung Cell Mol Physiol. 297(3):L401-10, 2009; Diamant et al., J Allergy Clin Immunol. 132(5):1045-1055, 2013.)

Different asthma subtypes that are refractory to steroid treatment have been identified. Eosinophils are important inflammatory cells in allergic asthma that is characteristically mediated by Th2-type CD4+ T cells. Neutrophilic airway inflammation is associated with corticosteroid treatment in severe asthma and can be mediated by Th1- or Th17-type T cells (Mishra et al., Dis. Model. Mech. 6:877-888, 2013).

Measures of diagnosis and assessment of asthma include the following:

Airway inflammation evaluated using a standardized single-breath Fraction of Exhaled Nitric Oxide (FeNO) (American Thoracic Society; ATS, Am J Respir Crit Care Med. 171(8):912-30, 2005) test. For example, subjects inhale to total lung capacity through the NIOX MING® Airway Inflammation Monitor and then exhale for 10 seconds at 50 mL/sec (assisted by visual and auditory cues).

Spirometry is performed according to ATS/European Respiratory Society (ERS) guidelines (Miller et al, Eur Respir J. 26(1):153-61, 2005). For example, multiple forced expiratory efforts (at least 3 but no more than 8) is performed at each spirometry session and the 2 best efforts that meet ATS/ERS acceptability and reproducibility criteria are recorded. The best efforts will be based on the highest $FEV_1$. The maximum $FEV_1$ of the 2 best efforts will be used for the analysis. Both the absolute measurement (for $FEV_1$ and FVC) and the percentage of predicted normal value will be recorded using appropriate reference values. The highest FVC will also be reported regardless of the effort in which it occurred (even if the effort did not result in the highest $FEV_1$).

Post-bronchodilator (Post-BD) spirometry testing is assessed after the subject has performed pre-BD spirometry. Maximal bronchodilation is induced using a SABA such as albuterol (90 µg metered dose) or salbutamol (100 µg metered dose) or equivalent with a spacer device for a maximum of 8 total puffs (Sorkness et al, J Appl Physiol. 104(2):394-403, 2008). The highest pre- and post-BD $FEV_1$ obtained after 4, 6, or 8 puffs is used to determine reversibility and for analysis. Reversibility algorithm is as follows:

% Reversibility=(post-BD FEV1−pre-BD FEV1)×100/pre-BD FEV1

Home peak flow testing for peak expiratory flow rate (PEFR) is performed twice daily, in the morning upon awakening and in the evening prior to bedtime using a peak flow meter from the morning of Visit 2 (Week −4) through Week 64. When possible, ambulatory lung function measurements should be taken at least 6 hours after the last dose of SABA rescue medication.

The Asthma Daily Diary includes the following daily assessments: asthma symptoms; inhalations of rescue medication; nighttime awakening due to asthma requiring rescue medication use, asthma-related activity limitations, asthma-related stress, and background medication compliance. The Asthma Daily Diary is completed each morning and evening. There will be triggers in the ePRO device to alert the subjects to signs of worsening of asthma.

The Asthma Control Questionnaire (ACQ) 6 is a patient-reported questionnaire assessing asthma symptoms (i.e., night-time waking, symptoms on waking, activity limitation, shortness of breath, wheezing) and daily rescue bronchodilator use and $FEV_1$ (Juniper et al, October 1999). The ACQ-6 is a shortened version of the ACQ that omits the $FEV_1$ measurement from the original ACQ score. Questions are weighted equally and scored from 0 (totally controlled) to 6 (severely uncontrolled). The mean ACQ score is the mean of the responses. Mean scores of ≤0.75 indicate well-controlled asthma, scores between 0.75 and ≤1.5 indicate partly-controlled asthma, and a score >1.5 indicates uncontrolled asthma (Juniper et al, Respir Med. 100(4):616-21, 2006). Individual changes of at least 0.5 are considered to be clinically meaningful (Juniper et al, Respir Med. 99(5):553-8, 2005).

The Asthma Quality of Life Questionnaire, Standardized (AQLQ[S])+12 (AQLQ(S)+12) is a 32-item questionnaire that measures the HRQoL experienced by asthma patients (Juniper et al, Chest. 115(5):1265-70, May 1999). The questionnaire comprises 4 separate domains (symptoms, activity limitations, emotional function, and environmental stimuli). Subjects are asked to recall their experiences during the previous 2 weeks and to score each of the 32 questions on a 7-point scale ranging from 7 (no impairment) to 1 (severe impairment). The overall score is calculated as the mean response to all questions. The 4 individual domain scores (symptoms, activity limitations, emotional function, and environmental stimuli) are the means of the responses to the questions in each of the domains. Individual improvement in both the overall score and individual domain scores of 0.5 has been identified as a minimally important change, with score changes of ≥1.5 identified as large meaningful changes (Juniper et al, J Clin Epidemiol. 47(1):81-7, 1994).

TSLP

Thymic stromal lymphopoietin (TSLP) is an epithelial cell-derived cytokine that is produced in response to pro-inflammatory stimuli and drives allergic inflammatory responses primarily through its activity on dendritic cells (Gilliet, J Exp Med. 197:1059-1067, 2003; Soumelis, Nat Immunol. 3:673-680, 2002; Reche, J Immunol. 167:336-343, 2001), mast cells (Allakhverdi, J Exp Med. 204:253-258, 2007) and CD34+ progenitor cells.[9] TSLP signals through a heterodimeric receptor consisting of the interleukin (IL)-7 receptor alpha (IL-7Ra) chain and a common γ chain-like receptor (TSLPR) (Pandey, Nat Immunol. 1:59-64, 2000; Park, J Exp Med. 192:659-669, 2000).

Human TSLP mRNA[10,11] and protein levels[11] are increased in the airways of asthmatic individuals compared to controls, and the magnitude of this expression correlates with disease severity.[10] Recent studies have demonstrated association of a single nucleotide polymorphism in the human TSLP locus with protection from asthma, atopic asthma and airway hyperresponsiveness, suggesting that differential regulation of TSLP gene expression might influence disease susceptibility.[1,12,13] These data suggest that targeting TSLP may inhibit multiple biological pathways involved in asthma.

Earlier non-clinical studies of TSLP suggested that after TSLP is released from airway epithelial cells or stromal cells, it activates mast cells, dendritic cells, and T cells to release Th2 cytokines (e.g., IL-4/13/5). Recently published human data demonstrated a good correlation between tissue TSLP gene and protein expression, a Th2 gene signature score, and tissue eosinophils in severe asthma. Therefore, an anti-TSLP target therapy may be effective in asthmatic patients with Th2-type inflammation (Shikotra et al, J Allergy Clin Immunol. 129(1):104-11, 2012).

Data from other studies suggest that TSLP may promote airway inflammation through Th2 independent pathways such as the crosstalk between airway smooth muscle and mast cells (Allakhverdi et al, J Allergy Clin Immunol. 123(4):958-60, 2009; Shikotra et al, supra). TSLP can also promote induction of T cells to differentiate into Th-17-cytokine producing cells with a resultant increase in neutrophilic inflammation commonly seen in more severe asthma (Tanaka et al, Clin Exp Allergy. 39(1):89-100, 2009). These data and other emerging evidence suggest that blocking TSLP may serve to suppress multiple biologic pathways including but not limited to those involving Th2 cytokines (IL-4/13/5).

Antibodies

It is contemplated that antibodies or antibody variants specific for TSLP are useful in the treatment of asthma, including severe asthma, eosinophlic asthma, no-eosinophilic/low-eosinophilic and other forms of asthma described herein.

Specific binding agents such as antibodies and antibody variants or fragments that bind to their target antigen, e.g., TSLP, are useful in the methods of the invention. In one embodiment, the specific binding agent is an antibody. The antibodies may be monoclonal (MAbs); recombinant; chimeric; humanized, such as complementarity-determining region (CDR)-grafted; human; antibody variants, including single chain; and/or bispecific; as well as fragments; variants; or derivatives thereof. Antibody fragments include those portions of the antibody that bind to an epitope on the polypeptide of interest. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Monoclonal antibodies may be modified for use as therapeutics or diagnostics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, Proc. Natl. Acad. Sci. 81:6851-55.

In another embodiment, a monoclonal antibody is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, Nature 321:522-25; Riechmann et al., 1998, Nature 332:323-27; Verhoeyen et al., 1988, Science 239:1534-36), by substituting at least a portion of a rodent complementarity-determining region for the corresponding regions of a human antibody.

Also encompassed by the invention are human antibodies and antibody variants (including antibody fragments) that bind TSLP. Using transgenic animals (e.g., mice) that are capable of producing a repertoire of human antibodies in the absence of endogenous immunoglobulin production such antibodies are produced by immunization with a polypeptide antigen (i.e., having at least 6 contiguous amino acids), optionally conjugated to a carrier. See, e.g., Jakobovits et al., 1993, Proc. Natl. Acad. Sci. 90:2551-55; Jakobovits et al., 1993, Nature 362:255-58; Bruggermann et al., 1993, Year in Immuno. 7:33. See also PCT App. Nos. PCT/US96/05928 and PCT/US93/06926. Additional methods are described in U.S. Pat. No. 5,545,807, PCT App. Nos. PCT/US9$^1$/$_2$45 and PCT/GB89/01207, and in European Patent Nos. 546073B1 and 546073A1. Human antibodies can also be produced by the expression of recombinant DNA in host cells or by expression in hybridoma cells as described herein.

Chimeric, CDR grafted, and humanized antibodies and/or antibody variants are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

Antibodies and antibody variants (including antibody fragments) useful in the present methods comprise an anti-TSLP antibody comprising a. a light chain variable domain comprising: i. a light chain CDR1 sequence comprising the amino acid sequence set forth in SEQ ID NO:3; ii. a light chain CDR2 sequence comprising the amino acid sequence set forth in SEQ ID NO:4; iii. a light chain CDR3 sequence comprising the amino acid sequence set forth in SEQ ID NO:5; and b. a heavy chain variable domain comprising: i. a heavy chain CDR1 sequence comprising the amino acid sequence set forth in SEQ ID NO:6; ii. a heavy chain CDR2 sequence comprising the amino acid sequence set forth in SEQ ID NO:7, and iii. a heavy chain CDR3 sequence comprising the amino acid sequence set forth in SEQ ID NO:8, wherein the antibody or antibody variant specifically binds to a TSLP polypeptide as set forth in amino acids 29-159 of SEQ ID NO:2.

Also contemplated is an antibody or antibody variant comprising a. a light chain variable domain selected from the group consisting of: i. a sequence of amino acids at least 80% identical to SEQ ID NO:12; ii. a sequence of amino acids encoded by a polynucleotide sequence that is at least 80% identical to SEQ ID NO:11; iii. a sequence of amino acids encoded by a polynucleotide that hybridizes under moderately stringent conditions to the complement of a polynucleotide consisting of SEQ ID NO:11; and b. a heavy chain variable domain selected from the group consisting of: i. a sequence of amino acids that is at least 80% identical to SEQ ID NO:10; ii. a sequence of amino acids encoded by a polynucleotide sequence that is at least 80% identical to SEQ ID NO:9; iii. a sequence of amino acids encoded by a polynucleotide that hybridizes under moderately stringent conditions to the complement of a polynucleotide consisting of SEQ ID NO:9; or c. a light chain variable domain of (a) and a heavy chain variable domain of (b), wherein the antibody or antibody variant specifically binds to a TSLP polypeptide as set forth in amino acids 29-159 of SEQ ID NO:2.

Tezepelumab is an exemplary anti-TSLP antibody having: a. i. a light chain CDR1 sequence comprising the amino acid sequence set forth in SEQ ID NO:3; ii. a light chain CDR2 sequence comprising the amino acid sequence set forth in SEQ ID NO:4; iii. a light chain CDR3 sequence comprising the amino acid sequence set forth in SEQ ID NO:5; and b. a heavy chain variable domain comprising: i. a heavy chain CDR1 sequence comprising the amino acid sequence set forth in SEQ ID NO:6; ii. a heavy chain CDR2 sequence comprising the amino acid sequence set forth in SEQ ID NO:7, and iii. a heavy chain CDR3 sequence comprising the amino acid sequence set forth in SEQ ID NO:8;

Tezepelumab also comprises a light chain variable domain having the amino acid sequence set out in SEQ ID NO:12; encoded by a polynucleotide sequence set out in SEQ ID NO:11; and a heavy chain variable domain having the amino acid sequence set out in SEQ ID NO:10, encoded by a polynucleotide sequence set out in SEQ ID NO:9.

Tezepelumab is an IgG2 antibody. The sequence of the full length heavy chain and light chain of tezepelumab, including the IgG2 chain, is set out in SEQ ID NOs: 105 and 106, respectively.

In various embodiments, the anti-TSLP antibody or antibody variant thereof is bivalent and selected from the group consisting of a human antibody, a humanized antibody, a chimeric antibody, a monoclonal antibody, a recombinant antibody, an antigen-binding antibody fragment, a single chain antibody, a monomeric antibody, a diabody, a triabody, a tetrabody, a Fab fragment, an IgG1 antibody, an IgG2 antibody, an IgG3 antibody, and an IgG4 antibody.

In various embodiments, the anti-TSLP antibody variant is selected from the group consisting of a diabody, a triabody, a tetrabody, a Fab fragment, single domain antibody, scFv, wherein the dose is adjusted such that the binding sites to be equimolar to the those dosed by bivalent antibodies.

It is contemplated that the antibody or antibody variant is an IgG2 antibody. Exemplary sequences for a human IgG2 constant region are available from the Uniprot database as Uniprot number P01859, incorporated herein by reference. Information, including sequence information for other antibody heavy and light chain constant regions is also publicly available through the Uniprot database as well as other databases well-known to those in the field of antibody engineering and production.

In certain embodiments, derivatives of antibodies include tetrameric glycosylated antibodies wherein the number and/or type of glycosylation site has been altered compared to the amino acid sequences of a parent polypeptide. In certain embodiments, variants comprise a greater or a lesser number of N-linked glycosylation sites than the native protein. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to human TSLP, or to increase or decrease the affinity of the antibodies to human TSLP described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

Methods of Administration

In one aspect, methods of the present disclosure include a step of administering a therapeutic anti-TSLP antibody or antibody variant described herein, optionally in a pharmaceutically acceptable carrier or excipient. In certain embodiments, the pharmaceutical composition is a sterile composition.

Contemplated herein are methods method for treating asthma in a subject, including severe asthma, eosinophilic or non-eosinophilic asthma and low eosinophil asthma. Surprisingly, it was found herein that treatment with an anti-TSLP antibody is effective at reducing asthma symptoms in a no eosinophil/low eosinophil population as it is in a high eosinophil population. Also contemplated is a method of reducing the frequency of asthma exacerbation in a subject.

Also contemplated herein are methods of treating asthma in a subject having a Th2 high asthma profile or a Th2 low asthma profile. It is contemplated that a TSLP antagonist that inhibits binding of the TSLP protein to its receptor complex will effectively treat a low eosinophil asthma population as the antibody described herein. Similarly, it is contemplated that a TSLP antagonist that inhibits binding of TSLP to its receptor complex will be effective in treating Th2 low asthma populations.

Provided herein is a method of treating a patient having low eosinophil asthma comprising administering an anti-TSLP antibody. Also contemplated is a method for treating a subject having asthma characterized by a low Th2 profile comprising administering an anti-TSLP antibody. In various embodiments, the antibody is tezepelumab or another anti-TSLP antibody described in the art. Exemplary anti-TSLP antibodies include antibodies described in WO 2017/042701, WO 2016/142426, WO 2010/017468, US20170066823, US20120020988 and U.S. Pat. No. 8,637,019, incorporated herein by reference, some of which are described below in Table A. In exemplary aspects, the anti-TSLP antibody is selected from an antibody of Table A.

TABLE A

| | |
|---|---|
| WO2017/042701 | An anti-TSLP antibody comprising a heavy chain (HC) CDR1 comprising the sequence of SEQ ID NO: 13, a HC CDR2 comprising the sequence of SEQ ID NO: 14, and a HC CDR3 comprising the sequence of SEQ ID NO: 15; |
| | An anti-TSLP antibody comprising a light chain (LC) CDR1 comprising the sequence of SEQ ID NO: 16, a LC CDR2 comprising the sequence of SEQ ID NO: 17, a LC CDR3 comprising the sequence of SEQ ID NO: 18; |
| | An anti-TSLP antibody comprising a heavy chain (HC) CDR1 comprising the sequence of SEQ ID NO: 19, a HC CDR2 comprising the sequence of SEQ ID NO: 20, a HC CDR3 comprising the sequence of SEQ ID NO: 15; |
| | An anti-TSLP antibody comprising a light chain (LC) CDR1 comprising the sequence of SEQ ID NO: 21, a LC CDR2 comprising the sequence of SEQ ID NO: 22, a LC CDR3 comprising the sequence of SEQ ID NO: 23; |
| | An anti-TSLP antibody comprising a HC variable region comprising the sequence of SEQ ID NO: 26 and/or a LC variable region comprising the sequence of SEQ ID NO: 27; |
| | An anti-TSLP antibody comprising a HC variable region comprising the sequence of SEQ ID NO: 28 and/or a LC variable region comprising the sequence of SEQ ID NO: 29; |
| | An anti-TSLP antibody that comprises a paratope comprising at least one of the following residues: Thr28, Asp31, Tyr32, Trp33, Asp56, Glu101, Ile102, Tyr103, Tyr104, Tyr105 of a heavy chain sequence of SEQ ID NO: 26 or Gly28, Ser29, Lys30, Tyr31, Tyr48, Asp50, Asn51, Glu52, Asn65, and Trp92 of a light chain sequence of SEQ ID NO: 27; |
| | An anti-TSLP antibody that specifically binds an epitope in human TSLP, wherein the epitope comprises at least one of the following residues: Lys38, Ala41, Leu44, Ser45, Thr46, Ser48, Lys49, Ile52, Thr53, Ser56, Gly57, Thr58, Lys59, Lys101, Gln145, and Arg149 of SEQ ID NO: 30; |
| WO2016/142426 | An anti-TSLP antibody comprising the amino acid sequence of SEQ ID NO: 31; |
| | An anti-TSLP antibody comprising a CDR1 comprising the sequence of SEQ ID NO: 32; a CDR2 comprising the sequence of SEQ ID NO: 33, and a CDR3 comprising the sequence of SEQ ID NO: 34; |
| | An anti-TSLP antibody comprising a CDR1 comprising the sequence of SEQ ID NO: 32; a CDR2 comprising the sequence of SEQ ID NO: 35, and a CDR3 comprising the sequence of SEQ ID NO: 34; |
| | An anti-TSLP antibody comprising a variant of the CDR1 of SEQ ID NO: 31 wherein the residue corresponding to residue 28 in SEQ ID NO: 31 is Pro, the residue corresponding to residue 30 in SEQ ID NO: 31 is Arg, the residue corresponding to residue 31 in SEQ ID NO: 31 is Asn, the residue corresponding to residue 32 in SEQ ID NO: 31 is Trp and the residue corresponding to residue 34 in SEQ ID NO: 31 is Asp; |
| | An anti-TSLP antibody comprising a variant of the CDR2 of SEQ ID NO: 31 wherein the residue corresponding to residue 50 in SEQ ID NO: 31 is Gly, the residue corresponding to residue 53 in SEQ ID NO: 31 is His and the residue corresponding to residue 55 in SEQ ID NO: 31 is Gln; |
| | An anti-TSLP antibody comprising a variant of the CDR3 of SEQ ID NO: 31 wherein the residue corresponding to residue 91 in SEQ ID NO: 31 is Ile, Leu, Val or Phe, the residue corresponding to residue 92 in SEQ ID NO: 31 is Gly or Ala, the residue corresponding to residue 93 in SEQ ID NO: 31 is Glu, Phe, Asp or Ser and the residue corresponding to residue 94 in SEQ ID NO: 31 is Asp. |
| WO2010/017468 | An anti-TSLP antibody (9B7) comprising a HC CDR3 comprising the sequence of SEQ ID NO: 38, wherein the other CDRs of the HC and LC comprise the sequences of SEQ ID NOs: 36, 37, and 39-41; |
| | An anti-TSLP antibody (6C5) comprising a HC CDR3 comprising the sequence of SEQ ID NO: 44, wherein the other CDRs of the HC and LC comprise the sequences of SEQ ID NOs: 42, 43, and 45-47; |
| | An anti-TSLP antibody (6A3) comprising a HC CDR3 comprising the sequence of SEQ ID NO: 50, wherein the other CDRs of the HC and LC comprise the sequences of SEQ ID NOs: 48, 49, and 51-53; |
| | An anti-TSLP antibody (1A11) comprising a HC CDR3 comprising the sequence of SEQ ID NO: 56, wherein the other CDRs of the HC and LC comprise the sequences of SEQ ID NOs: 54, 55, and 57-59; |
| | An anti-TSLP antibody comprising (i) heavy chain variable region of SEQ ID NO: 60 and/or the light chain variable region of SEQ ID NO: 61; |
| | An anti-TSLP antibody comprising (i) heavy chain variable region of SEQ ID NO: 62 and/or the light chain variable region of SEQ ID NO: 63; |
| | An anti-TSLP antibody comprising (i) heavy chain variable region of SEQ ID NO: 64 and/or the light chain variable region of SEQ ID NO: 65; |
| | An anti-TSLP antibody comprising (i) heavy chain variable region of SEQ |

TABLE A-continued

| | |
|---|---|
| | ID NO: 66 and/or the light chain variable region of SEQ ID NO: 67;<br>An anti-TSLP antibody comprising (i) heavy chain variable region of SEQ ID NO: 68 and/or the light chain variable region of SEQ ID NO: 69;<br>An anti-TSLP antibody comprising a HC CDR selected from the group consisting of SEQ ID NO: 38, SEQ ID NO: 44, SEQ ID NO: 50 and SEQ ID NO: 56, and analogs thereof;<br>An anti-TSLP antibody comprising a heavy chain comprising the following CDRs or analogs thereof CDRH1: RYNVH (SEQ ID NO: 36), CDRH2: MIWDGGSTDYNSALKS (SEQ ID NO: 37), CDRH3: NRYESG (SEQ ID NO: 38), and a light chain comprising the following CDRs or analogs thereof CDRL1: KSSQSLLNSGNRKNYLT (SEQ ID NO: 39), CDRL2: WASTRES (SEQ ID NO: 40), and CDRL3: QNDYTYPFTFGS (SEQ ID NO: 41); or<br>An anti-TSLP antibody comprising a heavy chain comprising the following CDRs or analogs thereof CRDH1: AYWMS (SEQ ID NO: 42), CDRH2: EINPDSSTINCTPSLKD (SEQ ID NO: 43), CDRH3: RLRPFWYFDVW (SEQ ID NO: 44), and a light chain comprising the following CDRs or analogs thereof CDRL1: RSSQSIVQSNGNTYLE (SEQ ID NO: 45), CDRL2: KVSNRFS (SEQ ID NQ: 46), and CDRL3: FQGSHVPRT (SEQ ID NO: 47);<br>An anti-TSLP antibody comprising a heavy chain comprising the following CDRs or analogs thereof CRDH1: TDYAWN (SEQ ID NO: 48), CDRH2: YIFYSGSTTYTPSLKS (SEQ ID NO: 49), CDRH3: GGYDVNYF (SEQ ID NO: 50), and a light chain comprising the following CDRs or analogs thereof CDPL1: LASQTIGAWLA (SEQ ID NO: 51), CDRL2: AATRLAD (SEQ ID NQ: 52), and CDPL3: QQFFSTPWT (SEQ ID NQ: 53);<br>An anti-TSLP antibody comprising a heavy chain comprising the following CDRs or analogs thereof CDRH1: GYTMN (SEQ ID NO: 54), CDRH2: LINPYNGVTSYNQKFK (SEQ ID NO: 55), CDRH3: GDGNYWYF (SEQ ID NO: 56), and a light chain comprising the following CDRs or analogs thereof CDRL1: SASSSVTYMHW (SEQ ID NO: 57), CDRL2: EISKLAS (SEQ ID NO: 58), and CDRL3: QEWNYPYTF (SEQ ID NO: 59);<br>An anti-TSLP antibody comprising a HC CDR1 comprising the sequence of SEQ ID NO: 70; a CDR2 comprising the sequence of SEQ ID NO: 71, and a CDR3 comprising the sequence of SEQ ID NO: 72;<br>An anti-TSLP antibody comprising a LC CDR1 comprising the sequence of SEQ ID NO: 73; a CDR2 comprising the sequence of SEQ ID NO: 74, and a CDR3 comprising the sequence of SEQ ID NO: 75; |
| US2012/0020988 | An anti-TSLP antibody comprising a heavy chain variable domain comprising a CDR1 region of SEQ ID NO: 76, a CDR2 region of SEQ ID NO: 77, and CDR3 region of SEQ ID NO: 78, and a light chain variable domain comprising a CDR1 region of SEQ ID NO: 79, a CDR2 region of SEQ ID NO: 80, and a CDR3 region of SEQ ID NO: 81.<br>An anti-TSLP antibody comprising a heavy chain variable domain comprising SEQ ID NO: 82 and a light chain variable domain comprising SEQ ID NO: 83;<br>An anti-TSLP antibody comprising a heavy chain variable domain comprising a CDR1 region of SEQ ID NO: 76 or 84, a CDR2 region of SEQ ID NO: 77 or 85, and CDR3 region of SEQ ID NO: 78, and a light chain variable domain comprising a CDR1 region of SEQ ID NO: 79 or 86, a CDR2 region of SEQ ID NO: 80, 87, or 88, and a CDR3 region of SEQ ID NO: 81.<br>An anti-TSLP antibody comprising a heavy chain variable domain comprising a CDR1 region of SEQ ID NO: 76, a CDR2 region of SEQ ID NO: 85, and CDR3 region of SEQ ID NO: 78, and a light chain variable domain comprising a CDR1 region of SEQ ID NO: 86, a CDR2 region of SEQ ID NO: 87 and a CDR3 region of SEQ ID NO: 81;<br>An anti-TSLP antibody comprising a heavy chain variable domain comprising a CDR1 region of SEQ ID NO: 76, a CDR2 region of SEQ ID NO: 85, and CDR3 region of SEQ ID NO: 78, and a light chain variable domain comprising a CDR1 region of SEQ ID NO: 86, a CDR2 region of SEQ ID NO: 88 and a CDR3 region of SEQ ID NO: 81;<br>An anti-TSLP antibody comprising a heavy chain variable domain comprising a CDR1 region of SEQ ID NO: 84, a CDR2 region of SEQ ID NO: 85, and CDR3 region of SEQ ID NO: 78, and a light chain variable domain comprising a CDR1 region of SEQ ID NO: 86, a CDR2 region of SEQ ID NO: 88 and a CDR3 region of SEQ ID NO: 81; or<br>An anti-TSLP antibody comprising a heavy chain variable domain comprising a CDR1 region of SEQ ID NO: 76, a CDR2 region of SEQ ID NO: 85, and CDR3 region of SEQ ID NO: 78, and a light chain variable domain comprising a CDR1 region of SEQ ID NO: 86, a CDR2 region of SEQ ID NO: 80 and a CDR3 region of SEQ ID NO: 81.<br>An anti-TSLP antibody comprising a heavy chain variable domain comprises SEQ ID NO: 89 and a light chain variable domain comprises SEQ ID NO: 90;<br>An anti-TSLP antibody comprising a heavy chain variable domain comprises SEQ ID NO: 89 and a light chain variable domain comprises SEQ ID NO: 91; |

TABLE A-continued

| | |
|---|---|
| | An anti-TSLP antibody comprising a heavy chain variable domain comprises SEQ ID NO: 92 and a light chain variable domain comprises SEQ ID NO: 93; <br> An anti-TSLP antibody comprising a heavy chain variable domain comprises SEQ ID NO: 89 and a light chain variable domain comprises SEQ ID NO: 94, |
| U.S. Pat. No. 8,637,019 | An anti-TSLP antibody comprising heavy chain variable region comprising: a CDR-H1 sequence comprising SEQ ID NO: 95, a CDR-H2 sequence comprising SEQ ID NO: 96, and a CDR-H3 sequence comprising SEQ ID NO: 97; and/or an antibody light chain variable region or a TSLP-binding fragment thereof, said light chain variable region comprising: a CDR-L1 sequence comprising SEQ ID NO: 98, a CDR-L2 sequence comprising SEQ ID NO: 99, and a CDR-L3 sequence comprising SEQ ID NO: 100. <br> An anti-TSLP antibody comprising a heavy chain variable region comprises the amino acid sequence of SEQ ID NO: 101 and the light chain variable region comprises the amino acid sequence of SEQ ID NO: 102. <br> An anti-TSLP antibody comprising SEQ ID NO: 103 and SEQ ID NO: 104. |

Also contemplated are methods for treating chronic obstructive pulmonary disease (COPD) in a subject comprising administering an anti-TSLP antibody or antibody variant.

It is contemplated that the subject to be treated is human. The subject may be an adult, an adolescent or a child.

Therapeutic antibody (or antibody variant) compositions may be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, weekly, every 2 weeks, every 3 weeks, monthly, or at a longer interval.

In various embodiments, the amounts of therapeutic agent, such as a bivalent antibody having two TSLP binding sites, in a given dosage may vary according to the size of the individual to whom the therapy is being administered as well as the characteristics of the disorder being treated.

In exemplary treatments, the anti-TSLP antibody or antibody variant is administered in a dose range of about 70 mg to about 280 mg per daily dose. For example, the dose may be given in about 70 mg, 210 mg or 280 mg. In various embodiments, the anti-TSLP antibody or antibody variant may be administered at a dose of 70, 80, 90, 100, 110, 120, 130, 140, 150, 160, 10, 180, 190, 200, 210, 220, 230, 240, 250, 260, 270 or 280 mg per dose. These concentrations may be administered as a single dosage form or as multiple doses. The above doses are given every two weeks or every four weeks. In various embodiments, the anti-TSLP antibody or antibody variant is administered at a single dose of 70 mg every two weeks or every four weeks. In various embodiments, the anti-TSLP antibody or antibody variant is administered at a single dose of 210 mg every two weeks or every four weeks. In various embodiments, the anti-TSLP antibody or antibody variant is administered at a single dose of 280 mg every two weeks or every four weeks.

For antibody variants, the amount of antibody variant should be such that the number of TSLP binding sites that are in the dose have an equimolar number of TSLP binding sites to canonical bivalent antibody described above.

It is contemplated that the anti-TSLP antibody or antibody variant is administered every 2 weeks or every 4 weeks for a period of at least 4 months, 6 months, 9 months, 1 year or more. In various embodiments, the administration is subcutaneous or intravenous.

Treatment with the anti-TSLP antibody or antibody variant is contemplated to decrease eosinophils in blood, sputum, broncheoalveolar fluid, or lungs of the subject. It is also contemplated that the administration shifts cell counts in the subject from a Th2 high population to a Th2 low population. It is further contemplated that administration of the anti-TSLP antibody improves one or more measures of asthma in a subject selected from the group consisting of forced expiratory volume (FEV), FEV1 reversibility, forced vital capacity (FVC), FeNO, Asthma Control Questionnaire-6 score and AQLQ(S)+12 score.

Improvement in asthma may be measured as one or more of the following: reduction in AER (annualized exacerbation rate), reduction in hospitalizations/severe exacerbations for asthma, change from baseline (increase) in time to first asthma exacerbation (following onset of treatment with anti-TSLP antibody), decrease relative to placebo in proportion of subjects with one or more asthma exacerbations or severe exacerbations over the course of treatment, e.g., 52 weeks, change from baseline (increase) in FEV1 and FVC (pre-broncholdilator and post-bronchodilator), change from baseline (decrease) in blood or sputum eosinophils (or lung eosinophils if biopsy or BAL fluid obtained), change from baseline (decrease) in FeNO, change from baseline (decrease) in IgE, improvement in asthma symptoms and control as measured by PROs including ACQ and variants, AQLQ and variants, SGRQ, and asthma symptom diaries, change (decrease) in use of rescue medications, decrease in use of systemic corticosteroids, decrease in Th2/Th1 cell ratio in blood. Most/all these measures should be in total population and subpopulations including hi and low eosinophils (Greater than or equal to 250 is high; less than 250 is low), allergic and non-allergic, Th2 hi and low, Periostin hi and low (compared to median value), and FeNO hi and low (greater than or equal to 24 or less than 24).

The treatment also improves one or more symptoms of asthma as measured by an asthma symptom diary. Symptoms include, but are not limited to, daytime and nighttime symptom frequency and severity, activity avoidance and limitation, asthma-related stress and fatigue as well as rescue asthma medication use), and other measures of asthma control as measured by the Asthma Control Questionnaire omitting $FEV_1$ (ACQ-6).

In various embodiments, treatment with the anti-TSLP antibody delays the time to an asthma exacerbation compared to a subject not receiving the anti-TSLP antibody.

Also contemplated in the present disclosure is the administration of multiple agents, such as an antibody composition in conjunction with a second agent as described herein, including but not limited to an anti-inflammatory agent or asthma therapy.

However, it is contemplated that, in various embodiments, the administration reduces frequency of or levels of co-administered therapy in the subject. Exemplary co-administered therapies include, but are not limited to, inhaled corticosteroids (ICS), long-acting β2 agonist (LABA), leukotriene receptor antagonists [LTRA], long-acting anti-muscarinics [LAMA], cromones, short-acting β2 agonist (SABA), and theophylline or oral corticosteroids. In various embodiments, the administration eliminates the need for corticosteroid therapy.

Formulations

In some embodiments, the disclosure contemplates use of pharmaceutical compositions comprising a therapeutically effective amount of an anti-TSLP antibody or antibody variant together with a pharmaceutically acceptable diluent, carrier, solubilizer, emulsifier, preservative, and/or adjuvant. In addition, the disclosure provides methods of treating a subject by administering such pharmaceutical composition.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolality, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, sucrose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18" Edition, (A. R. Genrmo, ed.), 1990, Mack Publishing Company.

A suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor.

The formulation components are present preferably in concentrations that are acceptable to the site of administration. In certain embodiments, buffers are used to maintain the composition at physiological pH or at a slightly lower pH, typically within a pH range of from about 5 to about 8. Including about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, and about 8.0.

In various embodiments, the anti-TSLP antibody or antibody variant is in a formulation containing sodium acetate, and one or more of proline, sucrose, polysorbate 20 or polysorbate 80. In various embodiments, the formulation comprises 1-50 mM sodium acetate, 3-9% (w/v) sucrose, 0.015% (w/v)±0.005% (w/v) polysorbate 20 or polysorbate 80, at pH between 4.9 and 6.0. Optionally, the antibody or antibody fragment is at a concentration of 70 mg/ml. The formulation may be stored at −20° to −70° C.

When parenteral administration is contemplated, the therapeutic compositions for use may be provided in the form of a pyrogen-free, parenterally acceptable aqueous solution comprising the desired anti-TSLP antibody in a pharmaceutically acceptable vehicle. A particularly suitable vehicle for parenteral injection is sterile distilled water in which the antibody is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the antibody.

EXAMPLES

The present anti-TSLP antibody is the first epithelium-targeting product with potential for disruptive efficacy in patients with both non-eosinophilic and eosinophilic asthma. EOS-high populations make up approximately 50-70% of severe asthma patients.

The present example describes a multicenter, placebo-controlled, parallel-group, double-blind phase 2 study conducted at 108 study sites across 12 countries. Eligible patients were current non-smokers (for months and with a history of <10 pack-years) who were aged 18-75 years and who had asthma that was not well-controlled despite treatment LABAs combined with a medium dose (250 to 500 µg per day of fluticasone administered by means of a dry-powder inhaler or equivalent) or high dose (>500 µg per day of fluticasone administered by means of a dry-powder inhaler or equivalent) of inhaled glucocorticoids (as per GINA 2012 guidelines defining severe asthma[24]) at least 6 months prior to enrollment. Patients were also required to have a history of at least two asthma exacerbations that led to systemic glucocorticoid treatment, or one severe exacerbation that led to hospitalization, in the 12 months before trial entry. Additional eligibility criteria included pre-bronchodilator (forced expiratory volume in 1 second ($FEV_1$) of at least 40% and no more than 80% of predicted, post-bronchodilator reversibility of at least 12% and at least 200 ml, and a score on the six-item Asthma Control Questionnaire (ACQ-6)25 score at least 1.5 during screening (range, 0 to 6, with lower scores indicating better disease control; minimal clinically important difference, 0.5).[26] Exclusion criteria included any clinically important pulmonary disease other than asthma. A full list of the inclusion and exclusion criteria is provided in Table 1A.

Patients were randomly assigned (in a 1:1:1:1 ratio), according to a central interactive voice-response or Web-response system, to receive one of three different doses of subcutaneous (SC) tezepelumab, a bivalent antibody having identical binding sites to TSLP, or placebo. Randomization was stratified by location (Japan or rest of world), blood eosinophil count (250 cells/μl or <250 cells/μl) as measured by a local laboratory, and dose level of inhaled glucocorticoids (medium or high, on the basis of GINA 2012 guidelines).[26] Patients receiving a maintenance regimen of oral glucocorticoids were assigned to the high-dose inhaled glucocorticoid stratum. Tezepelumab and placebo were prepared by site staff who were aware of the trial-group assignments and were not involved in trial assessments. The trial agents were similar in appearance and administered by staff who were unaware of the trial-group assignments. Background asthma control medications were maintained at a stable dose throughout the treatment period.

Procedures

Patients were assigned to receive SC injections of tezepelumab 70 mg every 4 weeks (Q4W, low dose), 210 mg Q4W (medium dose), or 280 mg every 2 weeks (Q2W, high dose), or placebo Q2W for the duration of the trial. To maintain blinding, patients who were assigned to randomized to the Q4W dosing regimens received placebo at the intermediate visits.

Baseline measurements of pre-bronchodilator and post-brochodilator spirometric assessments of fractional exhaled nitric oxide ($Fe_{NO}$)), blood eosinophil counts, ACQ-6 score, and the score on the asthma quality of life questionnaire (standardized) for persons 12 tears of age or older (AQLQ [S]+12 [hereafter referred to as AQLQ])27 were obtained throughout the 5-week screening period. The ACQ-6 score, AQLQ score, and Asthma symptom score (reflecting daytime severity, daytime frequency, and nighttime severity; range 0 [no symptoms] to 4 [worst possible symptoms]) were recorded using an electronic device. Safety was monitored at each study site from enrollment through follow-up at week 64.

Endpoints and Assessments

The primary efficacy endpoint was the annualized asthma exacerbation rate (AER) at week 52. An asthma exacerbation was defined as a worsening of asthma symptoms that led to any of the following: 1) use of systemic glucocorticoids (oral or injectable) or, in the case of stable maintenance regimen of oral glucocorticoids, a doubling of the dose for three or more days; 2) an emergency department visit due to asthma that led to systemic glucocorticoid treatment; or 3) an inpatient hospitalization due to asthma. Worsening of asthma was defined as new or increased symptoms or signs that were either worrisome to the patient or related to an asthma diary driven alert.

Secondary endpoints included change from baseline in prebronchdilator and postbronchodilator FEV1 (an increase in values indicates improved lung function; minimal clinically important difference, 100 to 200 ml), ACQ-6 score, AQLQ score, asthma symptom score, forced vital capacity (FVC), as well as the annualized rate of severe asthma exacerbations at week 52; the time to the first asthma exacerbation, the time to the first severe asthma exacerbation; the percentage of patients with at least one asthma exacerbation, and the percentage of patients with at least one severe asthma exacerbation.

Primary and secondary end points (changes from baseline in prebronchodilator FEV1, ACQ-6 score, AQLQ score, and asthma symptom score) were also assessed in pre-specified subpopulations according to blood eosinophil count (≥250 or <250 cells per microliter), Th2 status (high [IgE level >100 IU per milliliter and blood eosinophil count ≥140 cells per microliter] or low [IgE level ≤100 IU per milliliter or blood eosinophil count <140 cells per microliterp,[30] FENO level (on the basis of median baseline levels and the clinically meaningful cutoff of 24 ppb),[31] serum periostin level (high or low, on the basis of median baseline levels), current (demonstrated during the screening period) postbronchodilator FEV1 reversibility, and allergic status (defined by a positive or negative fluorescence enzyme immunoassay for IgE at baseline).

The primary end point was also stratified according to dose level of inhaled glucocorticoids (medium or high), use or nonuse of a maintenance regimen of oral glucocorticoids, and number of asthma exacerbations in the previous 12 months (pre-specified subgroup analyses). Post hoc analyses included stratification of the primary end point according to baseline blood eosinophil count (<400 or ≥400 cells per microliter) and patient smoking history.

Statistical Analysis

The efficacy analysis was based on the intent-to-treat (ITT) population, which consisted of patients who underwent randomization and received at least one dose of tezepelumab or placebo and analyzed according to the randomized trial group. The safety analyses were based on the as-treated population and included all the patients who received at least one dose of tezepelumab or placebo; patients were evaluated according to trial agent received.

For the primary efficacy endpoint, 138 patients per trial group were required for 80% power to detect a 40% lower annualized rate of asthma exacerbations in each tezepelumab dose group than in the placebo group, with a two sided alpha level of 0.1 and an expected 10% loss of information due to dropouts, under the assumption of an annualized asthma exacerbation rate of 0.7 events in the placebo group and a negative binomial dispersion parameter of 0.7.

The primary efficacy endpoint of annualized rate of asthma exacerbations was analyzed using a negative binomial model, with trial group, baseline blood eosinophil count (≥250 or <250 cells/μl) and baseline dose level of glucocorticoids (medium or high) included in the model. Continuous secondary endpoints were analyzed using a mixed-effects model for repeated measures analysis. Time-to-first event variables were analyzed using a Cox proportional hazard model. The categorical variables were analyzed using a Pearson's chi-squared test.

The primary endpoint was tested sequentially to control overall type-I error rate at 0.1. The hierarchy was tezepelumab high dose tezepelumab (280 mg Q2W) versus placebo, medium dose tezepelu,mab (210 mg Q4W) versus placebo, and low dose tesepelumab (70 mg Q4W) versus placebo. No adjustments for multiplicity for the secondary endpoints was applied. Nominal P values are presented. All analyses were done using SAS version 9.3.

Results

Patients

Analysis a, Primary Analysis after Database Lock, all Sites Included:

Overall, 918 subjects were screened and 584 patients underwent randomization: 145 were assigned to low dose tezepelumab (70 mg Q4W), 145 were assigned to medium dose tezepelumab (210 mg Q4W), 146 were assigned to high dose tezepelumab (280 mg Q2W) and 148 were assigned the placebo. Of the patients who received tezepelumab or placebo, and were included in the ITT population, 391 (89.7%) and 139 (93.9%) completed treatment, respectively. Baseline and clinical characteristics were similar across groups.

The dose range of inhaled glucocorticoids for patients at baseline is shown in FIGS. 2A and 2B. The median dose was 400 µg per day of fluticasone administered by means of a dry-powder inhaler or equivalent in the medium-dose inhaled glucocorticoid stratum, with 73 patients in the placebo group, 71 in the low-dose tezepelumab group, 70 in the medium-dose group, and 72 in the high-dose group, and 1000 µg per day of fluticasone administered by means of a dry-powder inhaler or equivalent in the high-dose inhaled glucocorticoid stratum, with 75, 74, 75, and 74 patients in the respective trial groups.

Primary Endpoint

Treatment with tezepelumab resulted in annualized rates of asthma exacerbations at week 52 of 0.25, 0.18, and 0.22 events in the low-dose, medium-dose, and high-dose groups, respectively, as compared with 0.67 events in the placebo group. Thus, exacerbation rates were lower in the tezepelumab groups than in the placebo group by 61% (90% confidence interval [CI], 39 to 75; P<0.001), 72% (90% CI, 54 to 83; P<0.001), and 66% (90% CI, 46 to 79; P<0.001), respectively (Table 2, and FIG. 1A). The types of asthma exacerbations that were used for the primary analysis are described in Table 1 B.

Secondary Endpoints

The annualized asthma exacerbation rate was lower in the tezepelumab groups than in the placebo group, irrespective of baseline eosinophil count or other assessed indicators of Th2 status (FIG. 2A; FIG. 6; Table 2; Table 4 and Tables 5, 7, 9 and 10). Among patients in the medium-dose inhaled glucocorticoid stratum, low-dose, medium-dose, and high-dose tezepelumab resulted in annualized asthma exacerbation rates at week 52 of 0.19, 0.14, and 0.20 events, respectively, as compared with 0.37 events with placebo. The rates in the tezepelumab groups were lower than the rate in the placebo group by 49% (95% CI, −14 to 77; P=0.10), 62% (95% CI, 8 to 84; P=0.03), and 47% (95% CI, 41-20 to 76; P=0.13), respectively. Among patients in the high-dose inhaled glucocorticoid stratum, low-dose, medium-dose, and high-dose tezepelumab resulted in annualized asthma exacerbation rates at week 52 of 0.32, 0.23, and 0.24 events, respectively, as compared with 0.96 events with placebo. The rates in the tezepelumab groups were lower than the rate in the placebo group by 67% (95% CI, 35 to 84; P=0.002), 76% (95% CI, 49 to 89; P<0.001), and 75% (95% CI, 47 to 88; P<0.001), respectively (Table 9). The annualized asthma exacerbation rate was lower in some, but not all, tezepelumab groups than in the placebo group when patients were stratified according to the number of asthma exacerbations in the previous 12 months and, in post hoc analyses, according to smoking history (Table 10).

Time to first asthma exacerbation was longer in the tezepelumab groups than in the placebo group. The risk of having any exacerbation was lower in the low dose, medium dose and high dose tezepelumab groups than in the placebo group by 35% (hazard ratio [HR] 0.65, 95% CI 0.40, 1.04; P=0.07), 53% (HR 0.47, 95% CI 0.28, 0.80; P=0.004), and 43% (HR 0.57, 95% CI 0.35 to 0.93; P=0.02), respectively (FIG. 3 and Table 7)

Figure 1B:
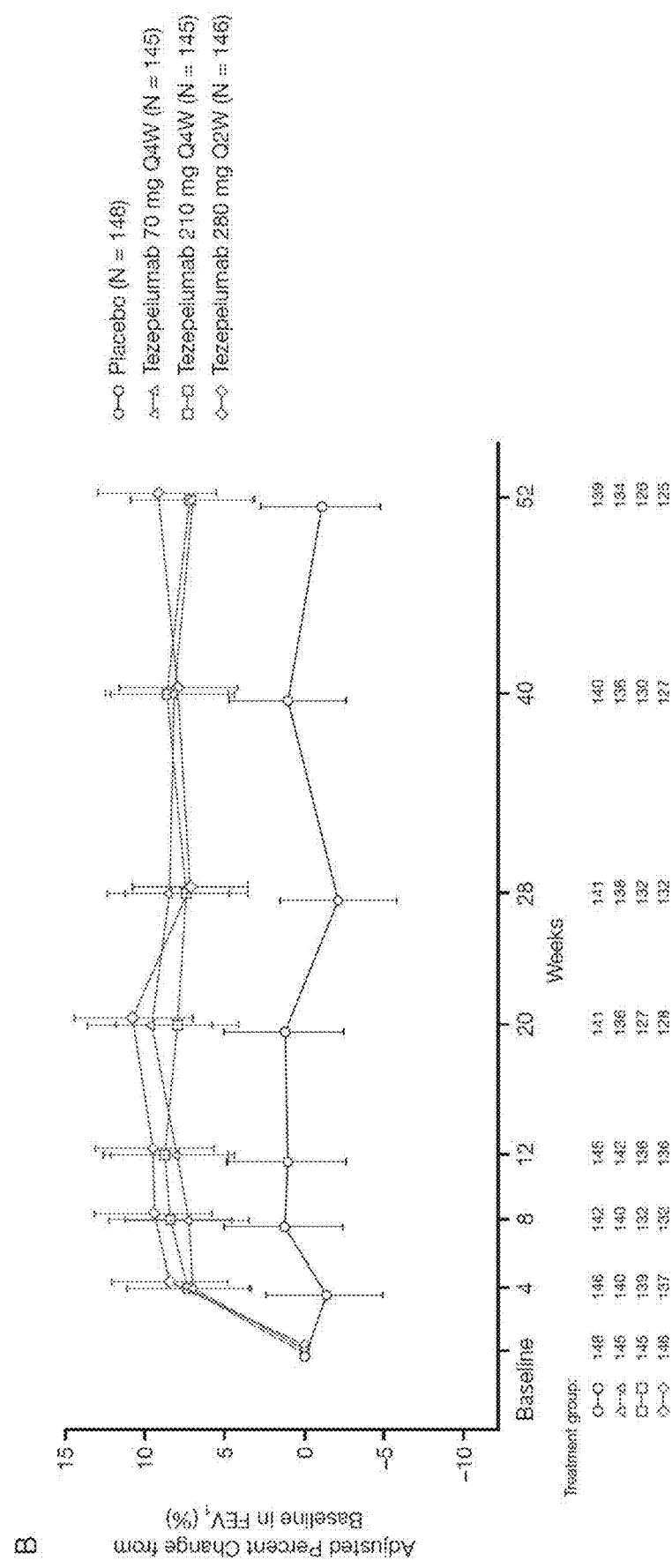

In the overall population, the change from baseline at week 52 in the pre-BD $FEV_1$ was greater in the low dose, medium dose and high dose tezepelumab groups than in the placebo group by 0.12 L (95% CI 0.02 to 0.21, P=0.01), 0.111 L (95% CI 0.02, to 0.21, P=0.02), and 0.15 L (95% CI 0.06, to 0.25, P=0.002), respectively (Table 2 and FIG. 1B). Similar differences were observed when the pre-BD FEV1 was measured as the percent of the predicted value (Table 2). The treatment effect was observed as early as week 4 (the first time point assessed) and was sustained for the duration of the trial (FIG. 1B, Table 2).

Figure 1C:
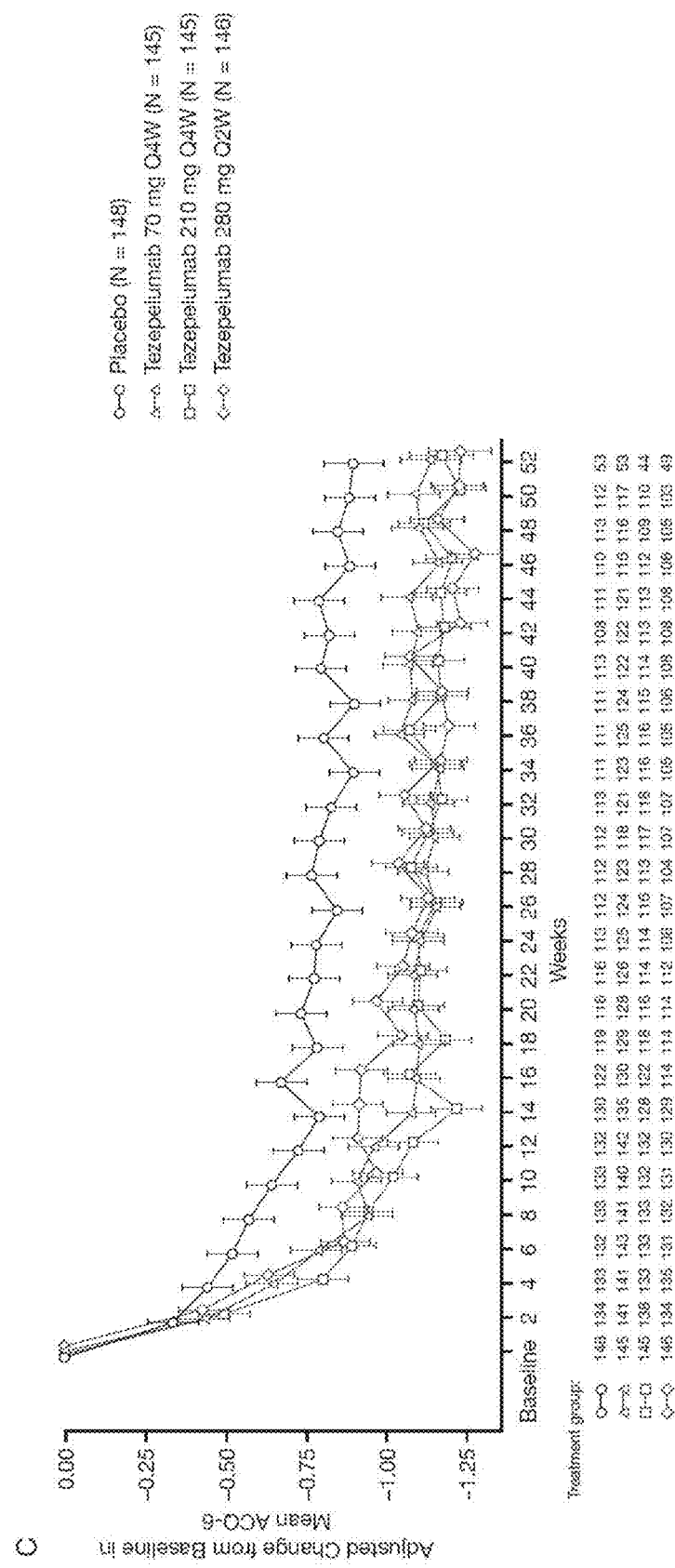
Figure 1D:
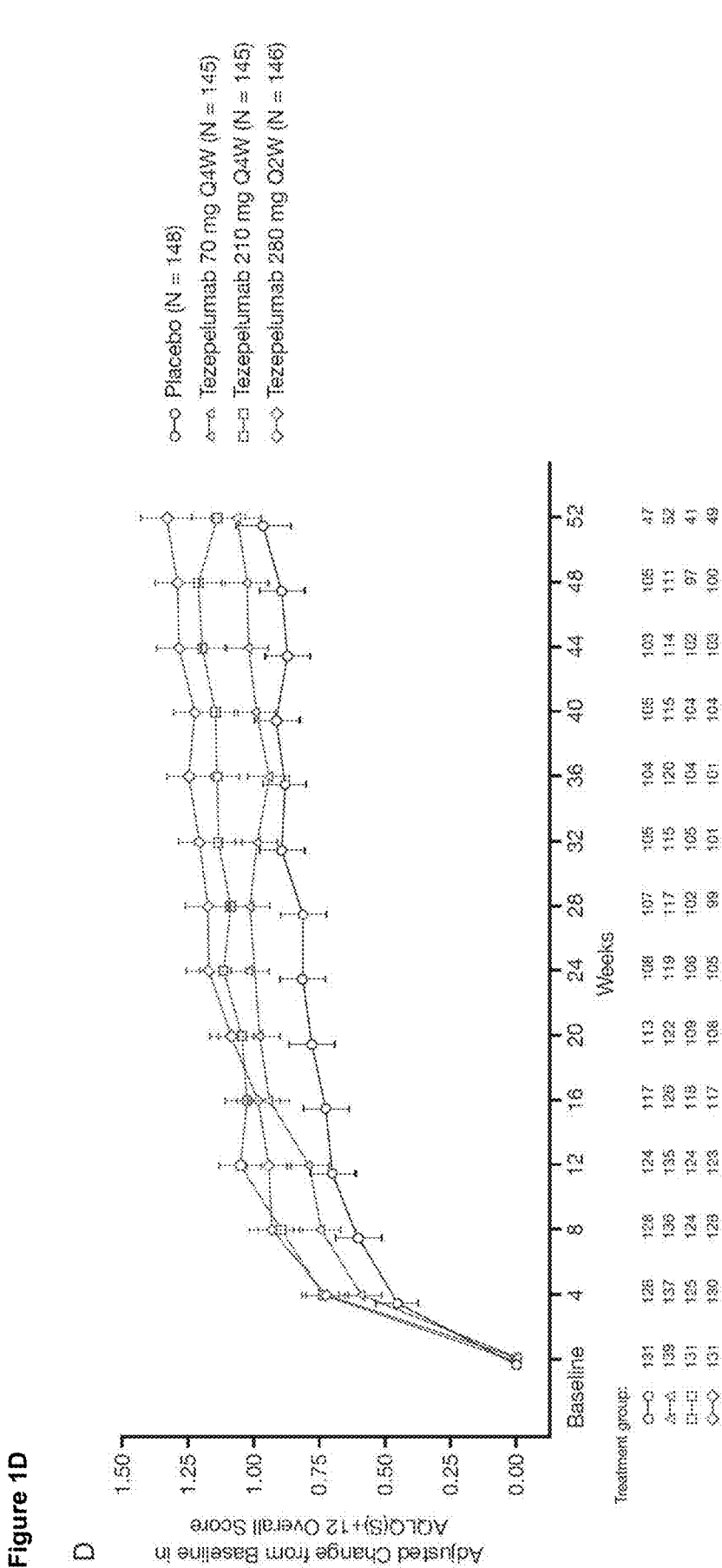

The effects of tezepelumab on additional secondary end points—including the percentage of patients with at least one asthma exacerbation, the percentage of patients with at least one severe asthma exacerbation, the annualized rate of severe asthma exacerbations, the time to the first severe asthma exacerbation and changes from baseline in the postbronchodilator FEV1, FVC, ACQ-6 score, AQLQ score, and asthma symptom score—are presented in Table 2, and FIGS. 1C and 1D and Tables 3, 5, 6 and 12. The effects of tezepelumab on secondary end points according to subgroup (prebronchodilator FEV1, ACQ-6 score, AQLQ score, and asthma symptom score) are shown in Tables 2, 4, 5 and 12.

Biomarkers

Substantial and persistent decreases in blood eosinophils and FeNO were observed in all tezepelumab treatment groups, beginning at week 4 (first time point assessed) after treatment initiation, and maintained over time (FIG. 4, FIG. 5, FIG. 6). Progressive decreases were also observed in total serum IgE in all tezepelumab groups (FIG. 4A).

Safety and Tolerability

The overall subject incidence of AEs was similar across treatment groups (Table 3). In total, 62.2% of the patients in the placebo group, 65.5% of the patients in the low dose tezepelumab group, 64.1% of the patients in the medium dose tezepelumab group, and 61.6% of patients in the high dose tezepelumab group reported at least one adverse event, and 12.2%, 11.7%, 9.0%, and 12.3%, reported at least one serious adverse event, respectively. When asthma-related adverse events were removed from the above analysis, the overall incidence of adverse events was similar across the trial groups. A full list of serious adverse events is provided in Table 12.

Three serious adverse events to be related to the trial agent; two (pneumonia and stroke) occurred in the same patient in the low dose tezepelumab group and one (the Guillain-Barre syndrome) in the medium dose tezepelumab group. The rates of discontinuation due to adverse events were 1.1% among patients receiving tezepelumab (five patients, including two in the medium dose group and three in the high dose group) and [0.7% in the placebo group (one patient). One patient in the low dose tezepelumab group died 8 weeks after the treatment period ended from a treatment-related serious adverse event (stroke in the same patient described above).

Injection-site reactions after 1-mL injections occurred in 3.4% of the patients in the placebo group, 2.8% of the patients in the low-dose tezepelumab group, 2.8% of the patients in the medium-dose group, and 1.4% of the patients in the high-dose group. The rates after 1.5-mL injections were 2.7%, 2.1%, 2.8%, and 3.4% in the respective groups. No investigational product-related anaphylactic reactions were reported. After baseline, positive antidrug antibodies were noted in 13 of 148 patients (8.8%) in the placebo group, 7 of 144 patients (4.9%) in the low-dose tezepelumab group, 0 of 144 patients in the medium-dose group, and 3 of 143 patients (2.1%) in the high-dose group. No neutralizing antibodies were detected.

Analysis B: Final Analysis after Database Lock, Includes all Sites:

For Analysis B, 145 patients were assigned to low dose tezepelumab (70 mg Q4W), 145 were assigned to medium dose tezepelumab (210 mg Q4W), 146 were assigned to high dose tezepelumab (280 mg Q2W) and 148 were assigned the placebo. Of the patients who received tezepelumab or placebo, and were included in the ITT population, 391 (89.7%) and 139 (93.9%) completed treatment, respectively. Baseline and clinical characteristics were similar across groups.

The dose range of inhaled glucocorticoids for patients at baseline for Analysis B is similar for Analysis A. The median dose was 400 µg per day of fluticasone administered by means of a dry-powder inhaler or equivalent in the medium-dose inhaled glucocorticoid stratum, with 73 patients in the placebo group, 71 in the low-dose tezepelumab group, 70 in the medium-dose group, and 72 in the high-dose group; and 1000 µg per day of fluticasone administered by means of a dry-powder inhaler or equivalent in the high-dose inhaled glucocorticoid stratum, with 75, 74, 75, and 74 patients in the respective trial groups.

Primary Endpoint

Treatment with tezepelumab resulted in annualized rates of asthma exacerbations at week 52 of 0.26, 0.19, and 0.22 events in the low-dose, medium-dose, and high-dose groups, respectively, as compared with 0.67 events in the placebo group. Thus, exacerbation rates were lower in the tezepelumab groups than in the placebo group by 61% (90% confidence interval [CI], 39 to 75; P<0.001), 71% (90% CI, 53 to 82; P<0.001), and 66% (90% CI, 47 to 79; P<0.001), respectively (Table 2, and FIG. 1A). The types of asthma exacerbations that were used for the primary analysis are described in Table 1B.

Secondary Endpoints

The annualized asthma exacerbation rate was lower in the tezepelumab groups than in the placebo group, irrespective of baseline eosinophil count or other assessed indicators of Th2 status (FIG. 2A; Table 2; Table 4 and Tables 5, 7, 9 and 10). Among patients in the medium-dose inhaled glucocorticoid stratum, low-dose, medium-dose, and high-dose tezepelumab resulted in annualized asthma exacerbation rates at week 52 of 0.19, 0.15, and 0.20 events, respectively, as compared with 0.38 events with placebo. The rates in the tezepelumab groups were lower than the rate in the placebo group by 51% (95% CI, −8 to 78; P=0.08), 60% (95% CI, 5 to 83; P=0.04), and 49% (95% CI, −13 to 77; P=0.10), respectively. Among patients in the high-dose inhaled glucocorticoid stratum, low-dose, medium-dose, and high-dose tezepelumab resulted in annualized asthma exacerbation rates at week 52 of 0.33, 0.23, and 0.24 events, respectively, as compared with 0.96 events with placebo. The rates in the tezepelumab groups were lower than the rate in the placebo group by 66% (95% CI, 33 to 83; P=0.002), 76% (95% CI, 49 to 89; P<0.001), and 75% (95% CI, 47 to 88; P<0.001), respectively (Table 9). The annualized asthma exacerbation rate was lower in some, but not all, tezepelumab groups than in the placebo group when patients were stratified according to the number of asthma exacerbations in the previous 12 months and, in post hoc analyses, according to smoking history (Table 10).

Time to first asthma exacerbation was longer in the tezepelumab groups than in the placebo group. The risk of having any exacerbation was lower in the low dose, medium dose and high dose tezepelumab groups than in the placebo group by 34% (hazard ratio [HR] 0.66, 95% CI 0.41, 1.05; P=0.08), 54% (HR 0.46, 95% CI 0.27, 0.78; P=0.003), and 45% (HR 0.55, 95% CI 0.34 to 0.90; P=0.02), respectively (FIG. 3 and Table 7)

In the overall population, the change from baseline at week 52 in the pre-BD FEV1 was greater in the low dose, medium dose and high dose tezepelumab groups than in the placebo group by 0.12 L (95% CI 0.02 to 0.21, P=0.01), 0.11 L (95% CI 0.02, to 0.20, P=0.02), and 0.15 L (95% CI 0.06, to 0.25, P=0.002), respectively (Table 2 and FIG. 1B). Similar differences were observed when the pre-BD FEV1 was measured as the percent of the predicted value (Table 2). The treatment effect was observed as early as week 4 (the first time point assessed) and was sustained for the duration of the trial (FIG. 1B, Table 2).

The effects of tezepelumab on additional secondary end points—including the percentage of patients with at least one asthma exacerbation, the percentage of patients with at least one severe asthma exacerbation, the annualized rate of severe asthma exacerbations, the time to the first severe asthma exacerbation and changes from baseline in the postbronchodilator FEV1, FVC, ACQ-6 score, AQLQ score, and asthma symptom score for Analysis B are consistent with those of Analysis A discussed above, and results in Table 2, and FIGS. 10 and 1D and Tables 3, 5, 6 and 12. The effects of tezepelumab on secondary end points according to subgroup (prebronchodilator FEV1, ACQ-6 score, AQLQ score, and asthma symptom score) are shown in Tables 2, 4, 5 and 12.

Biomarkers

Substantial and persistent decreases in blood eosinophils and FeNO were observed in all tezepelumab treatment groups, beginning at week 4 (first time point assessed) after treatment initiation, and maintained over time (FIG. 2 and FIG. 4). Progressive decreases were also observed in total serum IgE in all tezepelumab groups (FIG. 2B).

Safety and Tolerability

The overall subject incidence of AEs in Analysis B was consistent with Analysis A and was similar across treatment groups (Table 3). In total, 62.2% of the patients in the placebo group, 66.2% of the patients in the low dose tezepelumab group, 64.8% of the patients in the medium dose tezepelumab group, and 61.6% of patients in the high dose tezepelumab group reported at least one adverse event, and 12.2%, 11.7%, 9.0%, and 12.3%, reported at least one serious adverse event, respectively. When asthma-related adverse events were removed from the above analysis, the overall incidence of adverse events was similar across the trial groups. A full list of serious adverse events is provided in Table 12.

Three serious adverse events to be related to the trial agent; two (pneumonia and stroke) occurred in the same patient in the low dose tezepelumab group and one (Guillain-Barre syndrome) in the medium dose tezepelumab group. The rates of discontinuation due to adverse events were 1.1% among patients receiving tezepelumab (five patients, including two in the medium dose group and three in the high dose group) and 0.7% in the placebo group (one patient). One patient in the low dose tezepelumab group died 8 weeks after the treatment period ended from a treatment-related serious advserse event (stroke in the same patient described above).

For Analysis B, Injection-site reactions after 1-mL injections occurred in 3.4% of the patients in the placebo group, 2.8% of the patients in the low-dose tezepelumab group, 2.8% of the patients in the medium-dose group, and 1.4% of the patients in the high-dose group. The rates after 1.5-mL injections were 2.7%, 2.1%, 2.8%, and 3.4% in the respective groups. No investigational product-related anaphylactic reactions were reported. After baseline, positive antidrug antibodies were noted in 13 of 148 patients (8.8%) in the placebo group, 7 of 144 patients (4.9%) in the low-dose tezepelumab group, 1 of 140 patients (0.7%) in the medium-dose group, and 3 of 142 patients (2.1%) in the high-dose group. No neutralizing antibodies were detected.

In summary, the overall results of Analysis A and Analysis B were consistent.

Analysis C, after Data Lock, Single Site Results Omitted.

Based on the study sponsor's concerns about data integrity at one clinical site enrolled in the Phase 2 study, the data from Analysis B after data lock was re-analyzed with patients from this site omitted. For this second analysis, patients who received tezepelumab or placebo, and were included in the ITT population, 367 (89.1%) and 129 (93.5%) completed treatment, respectively. Baseline and clinical characteristics were similar across groups. Analysis C is consistent with the results of the previous analysis.

For Analysis C, 138 patients were assigned to low dose tezepelumab (70 mg Q4W), 137 were assigned to medium dose tezepelumab (210 mg Q4W), 137 were assigned to high dose tezepelumab (280 mg Q2W) and 138 were assigned the placebo. Of the patients who received tezepelumab or placebo, and were included in the ITT population (excluding patients from the omitted site), 367 (89.1%) and 129 (93.5%) completed treatment, respectively. Baseline and clinical characteristics were similar across groups The dose range of inhaled glucocorticoids for patients at baseline for Analysis B is similar for Analysis A and B, as shown in FIGS. 2A and 2B. The median dose was 400 μg per day of fluticasone administered by means of a dry-powder inhaler or equivalent in the medium-dose inhaled glucocorticoid stratum, with 73 patients in the placebo group, 67 in the low-dose tezepelumab group, 70 in the medium-dose group, and 71 in the high-dose group, and 1000 μg per day of fluticasone administered by means of a dry-powder inhaler or equivalent in the high-dose inhaled glucocorticoid stratum, with 65, 71, 67 and 66 patients in the respective trial groups.

Primary Endpoint

Treatment with tezepelumab resulted in annualized rates of asthma exacerbations at week 52 of 0.27, 0.20, and 0.23 events in the low-dose, medium-dose, and high-dose groups, respectively, as compared with 0.72 events in the placebo group. Thus, exacerbation rates were lower in the tezepelumab groups than in the placebo group by 62% (90% confidence interval [CI], 42 to 75; P<0.001), 71% (90% CI, 54 to 82; P<0.001), and 66% (90% CI, 47 to 79; P<0.001), respectively. The types of asthma exacerbations that were used for the primary analysis are described in Table 1B.

Secondary Endpoints

The annualized asthma exacerbation rate was lower in the tezepelumab groups than in the placebo group, irrespective of baseline eosinophil count or other assessed indicators of Th2 status. Among patients in the medium-dose inhaled glucocorticoid stratum, low-dose, medium-dose, and high-dose tezepelumab resulted in annualized asthma exacerbation rates at week 52 of 0.20, 0.15, and 0.20 events, respectively, as compared with 0.38 events with placebo. The rates in the tezepelumab groups were lower than the rate in the placebo group by 48% (95% CI, −15 to 76; P=0.11), 60% (95% CI, 5 to 83; P=0.04), and 48% (95% CI, −14 to 76; P=0.10), respectively. Among patients in the high-dose inhaled glucocorticoid stratum, low-dose, medium-dose, and high-dose tezepelumab resulted in annualized asthma exacerbation rates at week 52 of 0.35, 0.26, and 0.27 events, respectively, as compared with 1.12 events with placebo. The rates in the tezepelumab groups were lower than the rate in the placebo group by 70% (95% CI, 41 to 84; P=<0.001), 77% (95% CI, 52 to 89; P<0.001), and 76% (95% CI, 50 to 88; P<0.001), respectively. The annualized asthma exacerbation rate was lower in some, but not all, tezepelumab groups than in the placebo group when patients were stratified according to the number of asthma exacerbations in the previous 12 months and, in post hoc analyses, according to smoking history.

Time to first asthma exacerbation was longer in the tezepelumab groups than in the placebo group. The risk of having any exacerbation was lower in the low dose, medium dose and high dose tezepelumab groups than in the placebo group by 38% (hazard ratio [HR] 0.62, 95% CI 0.39, 0.99; P=0.04), 55% (HR 0.45, 95% CI 0.26, 0.75; P=0.002), and 46% (HR 0.54, 95% CI 0.33 to 0.88; P=0.01), respectively.

In the analyzed population, the change from baseline at week 52 in the pre-BD FEV1 was greater in the low dose, medium dose and high dose tezepelumab groups than in the placebo group by 0.12 L (95% CI 0.02 to 0.22, P=0.02), 0.13 L (95% CI 0.03, to 0.23, P=0.01), and 0.15 L (95% CI 0.05, to 0.25, P=0.002), respectively. Similar differences were observed when the pre-BD FEV1 was measured as the percent of the predicted value (Table 2). The treatment effect was observed as early as week 4 (the first time point assessed) and was sustained for the duration of the trial.

The effects of tezepelumab on additional secondary end points—including the percentage of patients with at least one asthma exacerbation, the percentage of patients with at least one severe asthma exacerbation, the annualized rate of severe asthma exacerbations, the time to the first severe asthma exacerbation and changes from baseline in the postbronchodilator FEV1, FVC, ACQ-6 score, AQLQ score, and asthma symptom score—for Analysis C are consistent with those of Analysis A and B discussed above. The effects of tezepelumab on secondary end points according to subgroup (prebronchodilator FEV1, ACQ-6 score, AQLQ score, and asthma symptom score) were also consistent with Analysis A and B above.

Biomarkers

Substantial and persistent decreases in blood eosinophils and FeNO were observed in all tezepelumab treatment groups, beginning at week 4 (first time point assessed) after treatment initiation, and maintained over time. Progressive decreases were also observed in total serum IgE in all tezepelumab groups.

Safety and Tolerability

The overall subject incidence of AEs in Analysis C was similar across treatment groups. In total, 65.9% of the patients in the placebo group, 67.4% of the patients in the low dose tezepelumab group, 65.7% of the patients in the medium dose tezepelumab group, and 65.0% of patients in the high dose tezepelumab group reported at least one adverse event, and 13.0%, 12.3%, 9.5%, and 13.1%, reported at least one serious adverse event, respectively. When asthma-related adverse events were removed from the above analysis, the overall incidence of adverse events was similar across the trial groups.

Three serious adverse events to be related to the trial agent; two (pneumonia and stroke) occurred in the same patient in the low dose tezepelumab group and one (the Guillain-Barre syndrome) in the medium dose tezepelumab group. The rates of discontinuation due to adverse events were 1.2% among patients receiving tezepelumab (five patients, including two in the medium dose group and three in the high dose group) and 0.7% in the placebo group (one patient). One patient in the low dose tezepelumab group died 8 weeks after the treatment period ended from a treatment-related serious adverse event (stroke in the same patient described above).

For Analysis C, injection-site reactions after 1-mL injections occurred in 3.6% of the patients in the placebo group, 2.9% of the patients in the low-dose tezepelumab group, 2.9% of the patients in the medium-dose group, and 1.5% of the patients in the high-dose group. The rates after 1.5-mL injections were 2.9%, 2.2%, 2.9%, and 3.6% in the respective groups. No investigational product-related anaphylactic reactions were reported. After baseline, positive antidrug antibodies were noted in 13 of 138 patients (9.4%) in the placebo group, 5 of 136 patients (3.7%) in the low-dose tezepelumab group, 1 of 131 patients (0.8%) in the medium-dose group, and 3 of 131 patients (2.3%) in the high-dose group. No neutralizing antibodies were detected.

In summary, the overall results of Analysis A, Analysis B and Analysis C were consistent.

Interestingly, a review of the effects of anti-TSLP treatment on the different high eosinophil and no eosinophil patients/low eosinophil patients showed that treatment with an anti-TSLP treatment was very effective in both high and low eosinophil patient populations, which would not have been expected in the low eosinophil population. Table 2 and FIG. 3 show that anti-TSLP treatment significantly reduced exacerbation rates in both eosinophil high and low populations.

Eosinophil cell levels in a subject are a marker for Th2 inflammation in a subject. In view of this association between eosinophils and Th2 levels, the study subjects were also divided into populations based on the relative Th2 levels at the start of treatment, e.g., Th2 high or low populations, and assayed for antibody efficacy. The results demonstrated that treatment with anti-TSLP was very effective in both Th2 high and Th2 low patient populations. Table 4 shows that anti-TSLP treatment significantly reduced exacerbation rates in both Th2 high and low populations, but to a greater extent in Th2 low patients.

Discussion

Treatment with tezepelumab resulted in significantly lower annualized rates of asthma exacerbations than the rate with placebo among patients whose asthma remained uncontrolled despite treatment with LABAs and medium- to high-doses of inhaled glucocorticoids. Some, but not all secondary outcomes were better with tezelpelumab than with placebo. Treatment effects were observed shortly after the initiation of treatment and were maintained throughout the trial. The incidence of adverse events was similar in the tezepelumab and placebo groups, with similar levels of discontinuations, regardless of asthma-related adverse events.

Tezepelumab reduced blood eosinophil counts, FeNO levels, and total serum IgE levels; changes in eosinophil counts and FeNO levels occurred rapidly from week 4 and concurrently with changes in clinical end points. These findings are consistent with the results from a previous allergen challenge study in patients with mild asthma, in which tezepelumab abrogated post-allergen challenge increases in sputum and blood eosinophils and FeNO.[24] These changes in biomarker levels demonstrate that TSLP is a key upstream regulator of Th2 activation and/or function, with effects on interleukin-4, interleukin-5, and interleukin-13 pathways, and indicate that inhibition of TSLP may have broader physiologic effects than individual Th2 cytokine inhibitors. Additionally, the epithelial-cell-derived cytokines interleukin-25 and interleukin-33 may work together with TSLP to initiate and amplify Th2 inflammation, although the interplay of these cytokines requires further investigation.[32, 33]

Tezepelumab was well-tolerated in all dose groups with no increase in reported infections compared with placebo.

The observed improvements in disease control following treatment with tezepelumab highlights the potential pathogenic role of TSLP across a range of asthma phenotypes. Non-allergic factors, including tobacco smoke, diesel particles and viruses, have been shown to trigger TSLP release and lead to activation of non-Th2 inflammatory responses in asthma.[34-37] Cell types which are activated by TSLP and may participate in these pathways, include mast cells, basophils, natural killer T cells, group 2 innate lymphoid cells and possibly neutrophils and interleukin-17 cells.[20,36-39]

The present data provides the first clinical evidence that inhibition of TSLP leads to a lower annualized rate of asthma exacerbations than no such inhibition, independent of baseline eosinophil count or other Th2 biomarkers and better results with respect to other clinical endpoints among patients with uncontrolled asthma who are receiving LABAs and medium-to-high doses of inhaled glucocorticoids. These findings highlight the potential advantages of targeting an upstream cytokine such as TSLP, which may affect disease activity more broadly than inhibition of a single downstream pathway.

Numerous modifications and variations of the invention as set forth in the above illustrative examples are expected to occur to those skilled in the art. Consequently only such limitations as appear in the appended claims should be placed on the invention.

REFERENCES

1. To T, Stanojevic S, Moores G, et al. BMC Public Health 2012; 12:204.
2. Chung K F, Wenzel S E, Brozek J L, et al. Eur Respir J 2014; 43:343-73.
3. Pavord I D, et al., NPJ Prim Care Respir Med 2017; 27:17.
4. Bateman E D, et al. Am J Respir Crit Care Med 2004; 170:836-44.
5. GINA Report. Global strategy for asthma management and prevention. August 2014. http://www.ginaasthma.org2014.
6. Woodruff P G, et al. Am J Respir Crit Care Med 2009; 180:388-95.
7. Wenzel S E. Am J Respir Cell Mol Biol 2016; 55:1-4.
8. Froidure A, et al., Eur Respir J 2016; 47:304-19.
9. Swedin L, et al. Pharmacol Ther 2017; 169:13-34.
10. Brightling C, Berry M, Amrani Y. J Allergy Clin Immunol 2008; 121:5-10; quiz 1-2.
11. Ortega H G, Liu M C, Pavord I D, et al. N Engl J Med 2014; 371:1198-207.
12. XOLAIR® (omalizumab): Highlights of Prescribing Information 2016. (at https://www.gene.com/download/pdf/xolair_prescribing.pdf.)
13. Bleecker E R, FitzGerald J M, Chanez P, et al. The Lancet 2016; 388:2115-27.
14. FitzGerald J M, Bleecker E R, Nair P, et al. The Lancet 2016; 388:2128-41.
15. Wenzel S, Castro M, Corren J, et al. Lancet 2016; 388:31-44.
16. Castro M, et al. Lancet Respir Med 2015; Epub, doi: 10.1016/S2213-2600(15)00042-9.

17. Brightling C E, Chanez P, Leigh R, et al. Lancet Respir Med 2015; 3:692-701.
18. Bel E H, Wenzel S E, Thompson P J, et al. N Engl J Med 2014; 371:1189-97.
19. Soumelis V, Reche P A, Kanzler H, et al. Nat Immunol 2002; 3:673-80.
20. Allakhverdi Z, Comeau M R, Jessup H K, et al J Exp Med 2007; 204:253-8.
21. Shikotra A, Choy D F, Ohri C M, et al. J Allergy Clin Immunol 2012; 129:104-11 e1-9.
22. Ying S, O'Connor B, Ratoff J, et al. J Immunol 2005; 174:8183-90.
23. Ying S, O'Connor B, Ratoff J, et al. J Immunol 2008; 181:2790-8.
24. Gauvreau G M, O'Byrne P M, Boulet L P, et al. N Engl J Med 2014; 370:2102-10.
25. Juniper E F, O'Byrne P M, Guyatt G H, Ferrie P J, King D R. Eur Respir J 1999; 14:902-7.
26. Global Strategy for Asthma Management and Prevention 2012.2012, at http://ginasthma.org/.)
27. Juniper E F, Buist A S, Cox F M, Ferrie P J, King D R. Chest 1999; 115:1265-70.
28. Corren J, Lemanske R F, Hanania N A, et al. N Engl J Med 2011; 365:1088-98.
29. Dweik R A, Boggs P B, Erzurum S C, et al. Am J Respir Crit Care Med 2011; 184:602-15.
30. Hanania N A, Wenzel S, Rosen K, et al. Am J Respir Crit Care Med 2013; 187:804-11.
31. Tabrizi M, Bornstein G G, Suria H. AAPS J 2010; 12:33-43.
32. Paul W E, Zhu J. Nat Rev Immunol 2010; 10:225-35.
33. Gavala M L, Bashir H, Gern J E. Curr Allergy Asthma Rep 2013; 13:298-307.
34. Nakamura Y, Miyata M, Ohba T, et al. J Allergy Clin Immunol 2008; 122:1208-14.
35. Bleck B, et al., Journal of clinical immunology 2008; 28:147-56.
36. Lee H C, Headley M B, Loo Y M, et al. J Allergy Clin Immunol 2012; 130:1187-96 e5.
37. Calven J, Yudina Y, Hallgren 0, et al. J Innate Immun 2012; 4:86-99.
38. Nagata Y, et al., Int Arch Allergy Immunol 2007; 144:305-14.
39. Kim B S, Siracusa M C, Saenz S A, et al. Sci Transl Med 2013; 5:170ra16.

What is claimed:

1. A method for treating asthma in a subject comprising administering a therapeutically effective amount of an anti-TSLP antibody or antibody variant in a dose of 70 mg to 280 mg at an interval of every 2 weeks or every 4 weeks, wherein both binding sites of the antibody have identical binding to TSLP, and the antibody comprises
   a. a light chain variable domain comprising:
   i. a light chain CDR1 sequence comprising the amino acid sequence set forth in SEQ ID NO:3;
   ii. a light chain CDR2 sequence comprising the amino acid sequence set forth in SEQ ID NO:4;
   iii. a light chain CDR3 sequence comprising the amino acid sequence set forth in SEQ ID NO:5; and
   b. a heavy chain variable domain comprising:
   i. a heavy chain CDR1 sequence comprising the amino acid sequence set forth in SEQ ID NO:6;
   ii. a heavy chain CDR2 sequence comprising the amino acid sequence set forth in SEQ ID NO:7, and
   iii. a heavy chain CDR3 sequence comprising the amino acid sequence set forth in SEQ ID NO:8, wherein the antibody specifically binds to a TSLP polypeptide as set forth in amino acids 29-159 of SEQ ID NO:2.

2. The method of claim 1 wherein the antibody or antibody variant is administered every 4 weeks.

3. The method of claim 1 wherein the antibody or antibody variant is administered at a dose of 70 mg.

4. The method of claim 1 wherein the antibody or antibody variant is administered at a dose of 210 mg.

5. The method of claim 1 wherein the antibody or antibody variant is administered at a dose of 280 mg.

6. The method of claim 1 wherein the antibody or antibody variant is administered for a period of at least 4 months, 6 months, 9 months, 1 year or more.

7. The method of claim 1, wherein said anti-TSLP antibody or antibody variant thereof is bivalent and selected from the group consisting of a human antibody, a humanized antibody, a chimeric antibody, a monoclonal antibody, a recombinant antibody, an antigen-binding antibody fragment, a single chain antibody, a monomeric antibody, a diabody, a triabody, a tetrabody, a Fab fragment, an IgG1 antibody, an IgG2 antibody, an IgG3 antibody, and an IgG4 antibody.

8. The method of claim 1, wherein the antibody is an IgG2 antibody.

9. The method of claim 1, wherein the antibody or antibody variant is a human antibody.

10. The method of claim 1 wherein, the antibody or antibody variant further comprises a pharmaceutically acceptable carrier or excipient.

11. The method of claim 1 wherein, wherein the asthma is severe asthma.

12. The method of claim 1, wherein the asthma is eosinophilic or non-eosinophilic asthma.

13. The method claim 1, wherein the asthma is low eosinophil asthma.

14. The method of claim 1, wherein the subject is an adult.

15. The method of claim 1, wherein the subject is a child or adolescent.

16. The method of claim 1, wherein the administration decreases eosinophils in blood, sputum, broncheoalveolar fluid, or lungs of the subject.

17. The method of claim 1, wherein the administration shifts cell counts in the subject from a Th2 high population to a Th2 low population.

18. The method of claim 1, wherein the administration improves one or more measures of asthma in a subject selected from the group consisting of forced expiratory volume (FEV), FEV₁ reversibility, forced vital capacity (FCV), FeNO, Asthma Control Questionnaire-6 score and AQLQ(S)+12 score.

19. The method of claim 1, wherein the administration improves one or more symptoms of asthma as measured by an asthma symptom diary.

20. The method of claim 1 wherein the antibody is tezepelumab.

21. The method of claim 20 wherein the antibody is an IgG2 antibody, and has the full length heavy and light chain sequences set out in SEQ ID NOs: 105 and 106, respectively.

22. The method of claim 1 wherein the administration is subcutaneous or intravenous.

23. A method for treating asthma in a subject comprising administering a therapeutically effective amount of an anti-TSLP antibody or antibody variant in a dose of 70 mg to 280 mg at an interval of every two weeks, wherein both binding sites of the antibody have identical binding to TSLP, and the antibody comprises
   a. a light chain variable domain selected from the group consisting of:
      i. a sequence of amino acids at least 80% identical to SEQ ID NO:12;
      ii. a sequence of amino acids encoded by a polynucleotide sequence that is at least 80% identical to SEQ ID NO:11;
      iii. a sequence of amino acids encoded by a polynucleotide that hybridizes under moderately stringent conditions to the complement of a polynucleotide consisting of SEQ ID NO:11; and
   b. a heavy chain variable domain selected from the group consisting of:
      i. a sequence of amino acids that is at least 80% identical to SEQ ID NO:10;
      ii. a sequence of amino acids encoded by a polynucleotide sequence that is at least 80% identical to SEQ ID NO:9;
      iii. a sequence of amino acids encoded by a polynucleotide that hybridizes under moderately stringent conditions to the complement of a polynucleotide consisting of SEQ ID NO:9; or c. a light chain variable domain of (a) and a heavy chain variable domain of (b), wherein the antibody specifically binds to a TSLP polypeptide as set forth in amino acids 29-159 of SEQ ID NO:2.

24. A method for treating asthma in a subject comprising administering a therapeutically effective amount of an anti-TSLP antibody or antibody variant in a dose of 210 mg at an interval of every 4 weeks, wherein both binding sites of the antibody have identical binding to TSLP, and the antibody comprises
   a. a light chain variable domain comprising:
      i. a light chain CDR1 sequence comprising the amino acid sequence set forth in SEQ ID NO:3;
      ii. a light chain CDR2 sequence comprising the amino acid sequence set forth in SEQ ID NO:4;
      iii. a light chain CDR3 sequence comprising the amino acid sequence set forth in SEQ ID NO:5; and
   b. a heavy chain variable domain comprising:
      i. a heavy chain CDR1 sequence comprising the amino acid sequence set forth in SEQ ID NO:6;
      ii. a heavy chain CDR2 sequence comprising the amino acid sequence set forth in SEQ ID NO:7, and
      iii. a heavy chain CDR3 sequence comprising the amino acid sequence set forth in SEQ ID NO:8, wherein the antibody specifically binds to a TSLP polypeptide as set forth in amino acids 29-159 of SEQ ID NO:2.

25. A method for treating asthma in a subject comprising administering a therapeutically effective amount of an anti-TSLP antibody or antibody variant in a dose of 210 mg at an interval of every 4 weeks, wherein both binding sites of the antibody have identical binding to TSLP, and the antibody comprises
   a. a light chain variable domain selected from the group consisting of:
      i. a sequence of amino acids at least 80% identical to SEQ ID NO:12;
      ii. a sequence of amino acids encoded by a polynucleotide sequence that is at least 80% identical to SEQ ID NO:11;
      iii. a sequence of amino acids encoded by a polynucleotide that hybridizes under moderately stringent conditions to the complement of a polynucleotide consisting of SEQ ID NO:11; and
   b. a heavy chain variable domain selected from the group consisting of:
      i. a sequence of amino acids that is at least 80% identical to SEQ ID NO:10;
      ii. a sequence of amino acids encoded by a polynucleotide sequence that is at least 80% identical to SEQ ID NO:9;
      iii. a sequence of amino acids encoded by a polynucleotide that hybridizes under moderately stringent conditions to the complement of a polynucleotide consisting of SEQ ID NO:9; or c. a light chain variable domain of (a) and a heavy chain variable domain of (b), wherein the antibody specifically binds to a TSLP polypeptide as set forth in amino acids 29-159 of SEQ ID NO:2.

26. The method of claim 25, wherein said anti-TSLP antibody variant is selected from the group consisting of a diabody, a triabody, a tetrabody, a Fab fragment, single domain antibody, scFv, wherein the dose is adjusted such that the binding sites to be equimolar to the those dosed by bivalent antibodies.

27. A method for treating asthma in a subject comprising administering a therapeutically effective amount of an anti-TSLP antibody or antibody variant in a dose of 70 to 280 mg at an interval of every 2 weeks or every 4 weeks, wherein both binding sites of the antibody have identical binding to TSLP, and the antibody comprises
   a. a light chain variable domain comprising:
      i. a light chain CDR1 sequence comprising the amino acid sequence set forth in SEQ ID NO:3;
      ii. a light chain CDR2 sequence comprising the amino acid sequence set forth in SEQ ID NO:4;
      iii. a light chain CDR3 sequence comprising the amino acid sequence set forth in SEQ ID NO:5; and
   b. a heavy chain variable domain comprising:
      i. a heavy chain CDR1 sequence comprising the amino acid sequence set forth in SEQ ID NO:6;
      ii. a heavy chain CDR2 sequence comprising the amino acid sequence set forth in SEQ ID NO:7, and
      iii. a heavy chain CDR3 sequence comprising the amino acid sequence set forth in SEQ ID NO:8, wherein the antibody specifically binds to a TSLP polypeptide as set forth in amino acids 29-159 of SEQ ID NO:2, wherein the antibody is an IgG2 antibody.

28. The method of claim 27 wherein the antibody is administered every 4 weeks.

29. The method of claim 27 wherein the antibody is administered at a dose of 70 mg, 210 mg or 280 mg.

30. A method of reducing the frequency of asthma exacerbation in a subject comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises
   a. a light chain variable domain comprising:
      i. a light chain CDR1 sequence comprising the amino acid sequence set forth in SEQ ID NO:3;
      ii. a light chain CDR2 sequence comprising the amino acid sequence set forth in SEQ ID NO:4;
      iii. a light chain CDR3 sequence comprising the amino acid sequence set forth in SEQ ID NO:5; and
   b. a heavy chain variable domain comprising:
      i. a heavy chain CDR1 sequence comprising the amino acid sequence set forth in SEQ ID NO:6;
      ii. a heavy chain CDR2 sequence comprising the amino acid sequence set forth in SEQ ID NO:7, and
      iii. a heavy chain CDR3 sequence comprising the amino acid sequence set forth in SEQ ID NO:8, wherein the antigen binding protein specifically binds to a TSLP polypeptide as set forth in amino acids 29-159 of SEQ ID NO:2.

31. The method of claim 30 wherein the antibody or antibody variant is administered every 4 weeks.

32. The method of claim 30 wherein the antibody or antibody variant is administered at a dose of 70 mg, 210 mg or 280 mg.

33. The method of claim 30 wherein the administration delays the time to an asthma exacerbation compared to a subject not receiving the anti-TSLP antibody.

34. The method claim 30 wherein the administration reduces frequency of or levels of co-administered therapy in the subject.

35. The method of claim 34 wherein the co-administered therapy is inhaled corticosteroids (ICS), long-acting β2 agonist (LABA), leukotriene receptor antagonists (LTRA), long-acting anti-muscarinics (LAMA), cromones, short-acting β2 agonist (SABA), and theophylline or oral corticosteroids.

36. The method of claim 34, wherein the administration eliminates the need for corticosteroid therapy.

37. The method of claim 30 wherein the anti-TSLP antibody is tezepelumab.

38. A method of reducing the frequency of asthma exacerbation in a subject comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises
   a. a light chain variable domain selected from the group consisting of:
      i. a sequence of amino acids at least 80% identical to SEQ ID NO:12;
      ii. a sequence of amino acids encoded by a polynucleotide sequence that is at least 80% identical to SEQ ID NO:11;
      iii. a sequence of amino acids encoded by a polynucleotide that hybridizes under moderately stringent conditions to the complement of a polynucleotide consisting of SEQ ID NO:11; and
   b. a heavy chain variable domain selected from the group consisting of:
      i. a sequence of amino acids that is at least 80% identical to SEQ ID NO:10;
      ii. a sequence of amino acids encoded by a polynucleotide sequence that is at least 80% identical to SEQ ID NO:9;
      iii. a sequence of amino acids encoded by a polynucleotide that hybridizes under moderately stringent conditions to the complement of a polynucleotide consisting of SEQ ID NO:9; or c. a light chain variable domain of (a) and a heavy chain variable domain of (b).

39. A method for reducing ACQ-6 score in a subject comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises
   a. a light chain variable domain comprising:
      i. a light chain CDR1 sequence comprising the amino acid sequence set forth in SEQ ID NO:3;
      ii. a light chain CDR2 sequence comprising the amino acid sequence set forth in SEQ ID NO:4;
      iii. a light chain CDR3 sequence comprising the amino acid sequence set forth in SEQ ID NO:5; and
   b. a heavy chain variable domain comprising:
      i. a heavy chain CDR1 sequence comprising the amino acid sequence set forth in SEQ ID NO:6;
      ii. a heavy chain CDR2 sequence comprising the amino acid sequence set forth in SEQ ID NO:7, and
      iii. a heavy chain CDR3 sequence comprising the amino acid sequence set forth in SEQ ID NO:8, wherein the antigen binding protein specifically binds to a TSLP polypeptide as set forth in amino acids 29-159 of SEQ ID NO:2.

40. A method for reducing ACQ-6 score in a subject comprising administering a therapeutically effective amount of an anti-TSLP antibody or antibody variant in a dose of 70 mg to 280 mg at an interval of every 2 weeks, wherein both binding sites of the antibody have identical binding to TSLP, and the antibody comprises
   a. a light chain variable domain selected from the group consisting of:
      i. a sequence of amino acids at least 80% identical to SEQ ID NO:12;
      ii. a sequence of amino acids encoded by a polynucleotide sequence that is at least 80% identical to SEQ ID NO:11;
      iii. a sequence of amino acids encoded by a polynucleotide that hybridizes under moderately stringent conditions to the complement of a polynucleotide consisting of SEQ ID NO:11; and
   b. a heavy chain variable domain selected from the group consisting of:
      i. a sequence of amino acids that is at least 80% identical to SEQ ID NO:10;
      ii. a sequence of amino acids encoded by a polynucleotide sequence that is at least 80% identical to SEQ ID NO:9;
      iii. a sequence of amino acids encoded by a polynucleotide that hybridizes under moderately stringent conditions to the complement of a polynucleotide consisting of SEQ ID NO:9; or c. a light chain variable domain of (a) and a heavy chain variable domain of (b).

41. The method of claim 40 wherein the administration is subcutaneous or intravenous.

42. A method for treating asthma in a subject having a non-eosinophilic profile or a low eosinophil profile comprising administering a therapeutically effective amount of an anti-TSLP antibody or antibody variant, wherein the antibody or antibody variant binding to TSLP inhibits TSLP activity.

43. The method of claim 42 wherein the anti-TSLP antibody or anti-TSLP antibody variant is selected from an antibody described in Table A:

TABLE A

| | |
|---|---|
| WO2017/042701 | An anti-TSLP antibody comprising a heavy chain (HC) CDR1 comprising the sequence of SEQ ID NO: 13, a HC CDR2 comprising the sequence of SEQ ID NO: 14, and a HC CDR3 comprising the sequence of SEQ ID NO: 15; An anti-TSLP antibody comprising a light chain (LC) CDR1 comprising the sequence of SEQ ID NO: 16, a LC CDR2 comprising the sequence of SEQ ID NO: 17, a LC CDR3 comprising the sequence of SEQ ID NO: 18; An anti-TSLP antibody comprising a heavy chain (HC) CDR1 comprising the sequence of SEQ ID NO: 19, a HC CDR2 comprising the sequence of SEQ ID NO: 20, a HC CDR3 comprising the sequence of SEQ ID NO: 15; An anti-TSLP antibody comprising a light chain (LC) CDR1 comprising the sequence of SEQ ID NO: 21, a LC CDR2 comprising the sequence of SEQ ID NO: 22, a LC CDR3 comprising the sequence of SEQ ID NO: 23; An anti-TSLP antibody comprising a HC variable region comprising the sequence of SEQ ID NO: 26 and/or a LC variable region comprising the sequence of SEQ ID NO: 27; An anti-TSLP antibody comprising a HC variable region comprising the sequence of SEQ ID NO: 28 and/or a LC variable region comprising the sequence of SEQ ID NO: 29; An anti-TSLP antibody that comprises a paratope comprising at least one of the following residues: Thr28, Asp31, Tyr32, Trp33, Asp56, Glu101, Ile102, Tyr103, Tyr104, Tyr105 of a heavy chain sequence of SEQ ID NO: 26 or Gly28, Ser29, Lys30, Tyr31, Tyr48, Asp50, Asn51, Glu52, Asn65, and Trp92 of a light chain sequence of SEQ ID NO: 27; An anti-TSLP antibody that specifically binds an epitope in human TSLP, wherein the epitope comprises at least one of the following residues: Lys38, Ala41, Leu44, Ser45, Thr46, Ser48, Lys49, Ile52, Thr53, Ser56, Gly57, Thr58, Lys59, Lys101, Gln145, and Arg149 of SEQ ID NO: 30; |
| WO2016/142426 | An anti-TSLP antibody comprising the amino acid sequence of SEQ ID NO: 31; An anti-TSLP antibody comprising a CDR1 comprising the sequence of SEQ ID NO: 32; a CDR2 comprising the sequence of SEQ ID NO: 33, and a CDR3 comprising the sequence of SEQ ID NO: 34; An anti-TSLP antibody comprising a CDR1 comprising the sequence of SEQ ID NO: 32; a CDR2 comprising the sequence of SEQ ID NO: 35, and a CDR3 comprising the sequence of SEQ ID NO: 34; An anti-TSLP antibody comprising a variant of the CDR1 of SEQ ID NO: 31 wherein the residue corresponding to residue 28 in SEQ ID NO: 31 is Pro, the residue corresponding to residue 30 in SEQ ID NO: 31 is Arg, the residue corresponding to residue 31 in SEQ ID NO: 31 is Asn, the residue corresponding to residue 32 in SEQ ID NO: 31 is Trp and the residue corresponding to residue 34 in SEQ ID NO: 31 is Asp; An anti-TSLP antibody comprising a variant of the CDR2 of SEQ ID NO: 31 wherein the residue corresponding to residue 50 in SEQ ID NO: 31 is Gly, the residue corresponding to residue 53 in SEQ ID NO: 31 is His and the residue corresponding to residue 55 in SEQ ID NO: 31 is Gln; An anti-TSLP antibody comprising a variant of the CDR3 of SEQ ID NO: 31 wherein the residue corresponding to residue 91 in SEQ ID NO: 31 is Ile, Leu, Val or Phe, the residue corresponding to residue 92 in SEQ ID NO: 31 is Gly or Ala, the residue corresponding to residue 93 in SEQ ID NO: 31 is Glu, Phe, Asp or Ser and the residue corresponding to residue 94 in SEQ ID NO: 31 is Asp. |
| WO2010/017468 | An anti-TSLP antibody (9B7) comprising a HC CDR3 comprising the sequence of SEQ ID NO: 38, wherein the other CDRs of the HC and LC comprise the sequences of SEQ ID NOs: 36, 37, and 39-41; An anti-TSLP antibody (6C5) comprising a HC CDR3 comprising the sequence of SEQ ID NO: 44, wherein the other CDRs of the HC and LC comprise the sequences of SEQ ID NOs: 42, 43, and 45-47; An anti-TSLP antibody (6A3) comprising a HC CDR3 comprising the sequence of SEQ ID NO: 50, wherein the other CDRs of the HC and LC comprise the sequences of SEQ ID NOs: 48, 49, and 51-53; An anti-TSLP antibody (1A11) comprising a HC CDR3 comprising the sequence of SEQ ID NO: 56, wherein the other CDRs of the HC and LC comprise the sequences of SEQ ID NOs: 54, 55, and 57-59; An anti-TSLP antibody comprising (i) heavy chain variable region of SEQ ID NO: 60 and/or the light chain variable region of SEQ ID NO: 61; An anti-TSLP antibody comprising (i) heavy chain variable region of SEQ ID NO: 62 and/or the light chain variable region of SEQ ID NO: 63; |

TABLE A-continued

| | |
|---|---|
| | An anti-TSLP antibody comprising (i) heavy chain variable region of SEQ ID NO: 64 and/or the light chain variable region of SEQ ID NO: 65; |
| | An anti-TSLP antibody comprising (i) heavy chain variable region of SEQ ID NO: 66 and/or the light chain variable region of SEQ ID NO: 67; |
| | An anti-TSLP antibody comprising (i) heavy chain variable region of SEQ ID NO: 68 and/or the light chain variable region of SEQ ID NO: 69; |
| | An anti-TSLP antibody comprising a HC CDR selected from the group consisting of SEQ ID NO: 38, SEQ ID NO: 44, SEQ ID NO: 50 and SEQ ID NO: 56, and analogs thereof; |
| | An anti-TSLP antibody comprising a heavy chain comprising the following CDRs or analogs thereof CDRH1: RYNVH (SEQ ID NO: 36), CDRH2: MIWDGGSTDYNSALKS (SEQ ID NO: 37), CDRH3: NRYESG (SEQ ID NO: 38), and a light chain comprising the following CDRs or analogs thereof CDRL1: KSSQSLLNSGNRKNYLT (SEQ ID NO: 39), CDRL2: WASTRES (SEQ ID NO: 40), and CDRL3: QNDYTYPFTFGS (SEQ ID NO: 41); or |
| | An anti-TSLP antibody comprising a heavy chain comprising the following CDRs or analogs thereof CRDH1: AYWMS (SEQ ID NO: 42), CDRH2: EINPDSSTINCTPSLKD (SEQ ID NO: 43), CDRH3: RLRPFWYFDVW (SEQ ID NO: 44), and a light chain comprising the following CDRs or analogs thereof CDRL1: RSSQSIVQSNGNTYLE (SEQ ID NO: 45), CDRL2: KVSNRFS (SEQ ID NO: 46), and CDRL3: FQGSHVPRT (SEQ ID NO: 47); |
| | An anti-TSLP antibody comprising a heavy chain comprising the following CDRs or analogs thereof CRDH1: TDYAWN (SEQ ID NO: 48), CDRH2: YIFYSGSTTYTPSLKS (SEQ ID NO: 49), CDRH3: GGYDVNYF (SEQ ID NO: 50), and a light chain comprising the following CDRs or analogs thereof CDRL1: LASQTIGAWLA (SEQ ID NO: 51), CDRL2: AATRLAD (SEQ ID NO: 52), and CDRL3: QQFFSTPWT (SEQ ID NO: 53); |
| | An anti-TSLP antibody comprising a heavy chain comprising the following CDRs or analogs thereof CDRH1: GYTMN (SEQ ID NO: 54), CDRH2: LINPYNGVTSYNQKFK (SEQ ID NO: 55), CDRH3: GDGNYWYF (SEQ ID NO: 56), and a light chain comprising the following CDRs or analogs thereof CDRL1: SASSSVTYMHW (SEQ ID NO: 57), CDRL2: EISKLAS (SEQ ID NO: 58), and CDRL3: QEWNYPYTF (SEQ ID NO: 59); |
| | An anti-TSLP antibody comprising a HC CDR1 comprising the sequence of SEQ ID NO: 70; a CDR2 comprising the sequence of SEQ ID NO: 71, and a CDR3 comprising the sequence of SEQ ID NO: 72; |
| | An anti-TSLP antibody comprising a LC CDR1 comprising the sequence of SEQ ID NO: 73; a CDR2 comprising the sequence of SEQ ID NO: 74, and a CDRS comprising the sequence of SEQ ID NO: 75; |
| US2012/0020988 | An anti-TSLP antibody comprising a heavy chain variable domain comprising a CDR1 region of SEQ ID NO: 76, a CDR2 region of SEQ ID NO: 77, and CDR3 region of SEQ ID NO: 78, and a light chain variable domain comprising a CDR1 region of SEQ ID NO: 79, a CDR2 region of SEQ ID NO: 80, and a CDR3 region of SEQ ID NO: 81. |
| | An anti-TSLP antibody comprising a heavy chain variable domain comprising SEQ ID NO: 82 and a light chain variable domain comprising SEQ ID NO: 83; |
| | An anti-TSLP antibody comprising a heavy chain variable domain comprising a CDR1 region of SEQ ID NO: 76 or 84, a CDR2 region of SEQ ID NO: 77 or 85, and CDR3 region of SEQ ID NO: 78, and a light chain variable domain comprising a CDR1 region of SEQ ID NO: 79 or 86, a CDR2 region of SEQ ID NO: 80, 87, or 88, and a CDR3 region of SEQ ID NO: 81. |
| | An anti-TSLP antibody comprising a heavy chain variable domain comprising a CDR1 region of SEQ ID NO: 76, a CDR2 region of SEQ ID NO: 85, and CDR3 region of SEQ ID NO: 78, and a light chain variable domain comprising a CDR1 region of SEQ ID NO: 86, a CDR2 region of SEQ ID NO: 87 and a CDR3 region of SEQ ID NO: 81; |
| | An anti-TSLP antibody comprising a heavy chain variable domain comprising a CDR1 region of SEQ ID NO: 76, a CDR2 region of SEQ ID NO: 85, and CDR3 region of SEQ ID NO: 78, and a light chain variable domain comprising a CDR1 region of SEQ ID NO: 86, a CDR2 region of SEQ ID NO: 88 and a CDR3 region of SEQ ID NO: 81; |
| | An anti-TSLP antibody comprising a heavy chain variable domain comprising a CDR1 region of SEQ ID NO: 84, a CDR2 region of SEQ ID NO: 85, and CDR3 region of SEQ ID NO: 78, and a light chain variable domain comprising a CDR1 region of SEQ ID NO: |

TABLE A-continued

| | |
|---|---|
| | 86, a CDR2 region of SEQ ID NO: 88 and a CDR3 region of SEQ ID NO: 81; or<br>An anti-TSLP antibody comprising a heavy chain variable domain comprising a CDR1 region of SEQ ID NO: 76, a CDR2 region of SEQ ID NO: 85, and CDR3 region of SEQ ID NO: 78, and a light chain variable domain comprising a CDR1 region of SEQ ID NO: 86, a CDR2 region of SEQ ID NO: 80 and a CDR3 region of SEQ ID NO: 81.<br>An anti-TSLP antibody comprising a heavy chain variable domain comprises SEQ ID NO: 89 and a light chain variable domain comprises SEQ ID NO: 90;<br>An anti-TSLP antibody comprising a heavy chain variable domain comprises SEQ ID NO: 89 and a light chain variable domain comprises SEQ ID NO: 91;<br>An anti-TSLP antibody comprising a heavy chain variable domain comprises SEQ ID NO: 92 and a light chain variable domain comprises SEQ ID NO: 93;<br>An anti-TSLP antibody comprising a heavy chain variable domain comprises SEQ ID NO: 89 and a light chain variable domain comprises SEQ ID NO: 94, |
| U.S. Pat. No. 8,637,019 | An anti-TSLP antibody comprising heavy chain variable region comprising: a CDR-H1 sequence comprising SEQ ID NO: 95, a CDR-H2 sequence comprising SEQ ID NO: 96, and a CDR-H3 sequence comprising SEQ ID NO: 97; and/or an antibody light chain variable region or a TSLP-binding fragment thereof, said light chain variable region comprising: a CDR-L1 sequence comprising SEQ ID NO: 98, a CDR-L2 sequence comprising SEQ ID NO: 99, and a CDR-L3 sequence comprising SEQ ID NO: 100.<br>An anti-TSLP antibody comprising a heavy chain variable region comprises the amino acid sequence of SEQ ID NO: 101 and the light chain variable region comprises the amino acid sequence of SEQ ID NO: 102.<br>An anti-TSLP antibody comprising SEQ ID NO: 103 and SEQ ID NO: 104. |

44. The method of claim 42 wherein the subject has an eosinophil count less than 250 cells/μL at start of treatment.

45. The method of claim 42 wherein the administration is subcutaneous or intravenous.

46. A method for treating asthma in a subject having a Th2 low profile comprising administering a therapeutically effective amount of an anti-TSLP antibody or antibody variant, wherein the antibody or antibody variant binding to TSLP inhibits TSLP activity.

47. The method of claim 46 wherein the subject has a Th2 profile of IgE less than or equal to 100 IU/ml or eosinophil count of less than 140 cells/μL at the time of diagnosis.

48. A method for reducing ACQ-6 score in a subject having a low eosinophil profile comprising administering a therapeutically effective amount of an anti-TSLP antibody or antibody variant, wherein the antibody or antibody variant binding to TSLP inhibits TSLP activity.

* * * * *